(12) United States Patent
Snow et al.

(10) Patent No.: US 10,590,176 B2
(45) Date of Patent: Mar. 17, 2020

(54) ENGINEERED PROGRAMMABLE MOLECULAR SCAFFOLDS FROM POROUS PROTEIN CRYSTALS

(71) Applicant: Colorado State University Research Foundation, Fort Collins, CO (US)

(72) Inventors: Christopher D. Snow, Fort Collins, CO (US); Thaddaus R. Huber, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 262 days.

(21) Appl. No.: 15/627,788

(22) Filed: Jun. 20, 2017

(65) Prior Publication Data

US 2017/0362282 A1 Dec. 21, 2017

Related U.S. Application Data

(60) Provisional application No. 62/352,428, filed on Jun. 20, 2016.

(51) Int. Cl.
| | |
|---|---|
| *G01N 23/207* | (2018.01) |
| *C07K 14/205* | (2006.01) |
| *C07K 14/435* | (2006.01) |
| *C07K 14/235* | (2006.01) |
| *C12N 9/02* | (2006.01) |
| *C12N 9/12* | (2006.01) |
| *C07K 14/005* | (2006.01) |
| *C07K 14/195* | (2006.01) |
| *C30B 29/58* | (2006.01) |

(52) U.S. Cl.
CPC .......... *C07K 14/205* (2013.01); *C07K 14/005* (2013.01); *C07K 14/195* (2013.01); *C07K 14/235* (2013.01); *C07K 14/435* (2013.01); *C12N 9/0004* (2013.01); *C12N 9/12* (2013.01); *C30B 29/58* (2013.01); *G01N 23/207* (2013.01); *C12N 2795/10222* (2013.01); *G01N 2223/612* (2013.01)

(58) Field of Classification Search
CPC .. C07K 14/205; C07K 14/005; C07K 14/195; C07K 14/235; C07K 14/435; C12N 9/0004; C12N 9/12; C12N 2795/10222; C30B 29/00; G01N 23/207; G01N 2223/612
See application file for complete search history.

(56) References Cited

PUBLICATIONS

McMillan et al., "Ordered nanoparticle arrays in formed on engineered chaperonin protein templates," 2002, vol. 1 Nature Materials, pp. 247-252. (Year: 2002).*
Shah et al., "Selective crystallization of proteins using engineered nanonucleants," 2012, Crystal Growth & Design, vol. 12, pp. 1362-1369 (Year: 2012).*
Liang et al., "Cross-linked lysozyme crystal templated synthesis of Au nanoparticles as high-performance recyclable catalysts," 2013, Nanotechnology, vol. 24, pp. 1-8. (Year: 2013).*

(Continued)

*Primary Examiner* — Kiho Kim
(74) *Attorney, Agent, or Firm* — Polsinelli PC

(57) ABSTRACT

The present disclosure provides compositions and methods for preparing engineered porous protein crystals comprising at least one guest molecule.

46 Claims, 23 Drawing Sheets
(16 of 23 Drawing Sheet(s) Filed in Color)
Specification includes a Sequence Listing.

(56) References Cited

PUBLICATIONS

Abe et al., "Porous protein crystals as reaction vessels for controlling magnetic properties of nanoparticles," 2012, Bioinorganic materials Communication, vol. 8, No. 9, pp. 1314-1319. (Year: 2012).*

Kowalski et al., "Gold nanoparticle capture within protein crystal scaffolds," 2016, Royal Society of Chemistry, vol. 8, pp. 12693-12696. (Year: 2016).*

He et al., "Antibacterial effect and proteomic analysis of graphene-based silver nanoparticles on a pathogenic bacterium *Psedomonas aeruginosa*," 2014, Biometals, vol. 27, pp. 673-682. (Year: 2014).*

Liu et al., "Opening protein pores with chaotropes enhances Fe Reduction and chelation of Fe from the ferritin biomineral," 2003, PNAS, vol. 100, No. 7, pp. 3653-3658. (Year: 2003).*

Tabe et al., "Preparation of a cross-linked porous protein crystal containing Ru Carbonyl Complexes as a CO-releasing extracellular scaffold," 2015, Inorganic Chemistry, vol. 54, pp. 215-220. (Year: 2015).*

\* cited by examiner

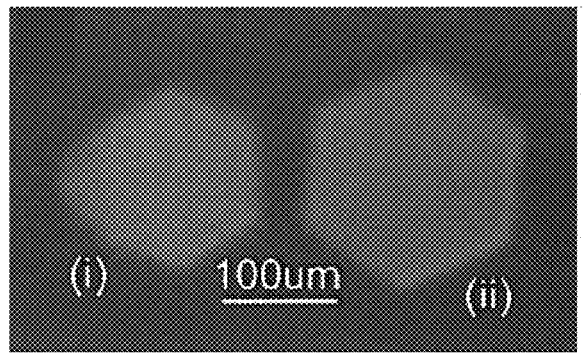
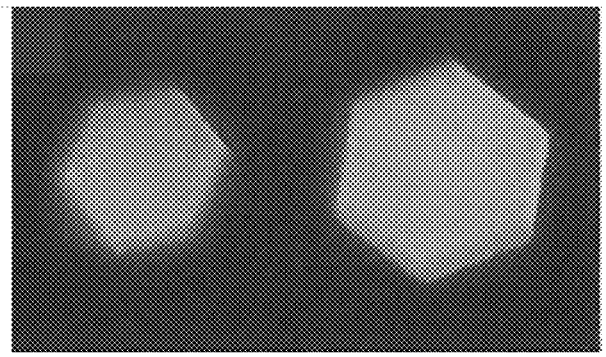
FIG. 7A  FIG. 7B
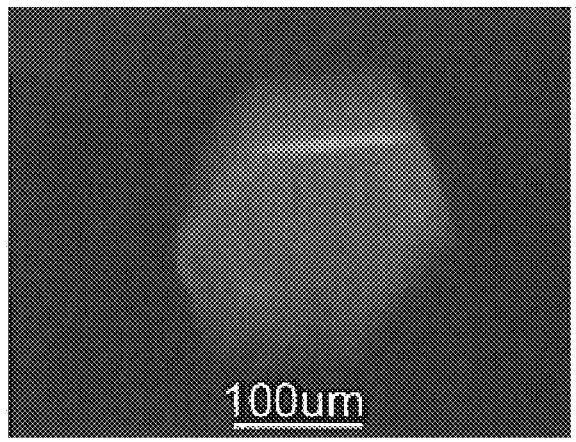
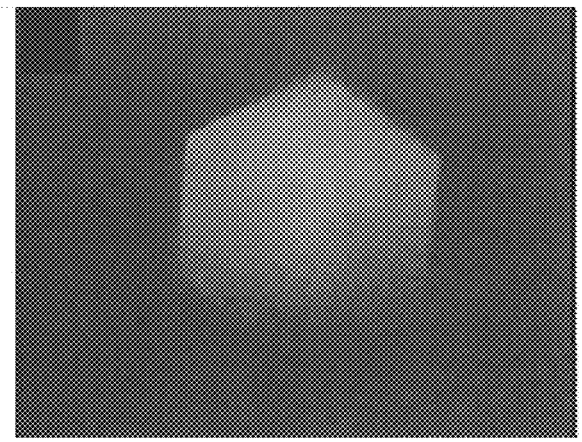
FIG. 8A  FIG. 8B

… (1)

ENGINEERED PROGRAMMABLE MOLECULAR SCAFFOLDS FROM POROUS PROTEIN CRYSTALS

CROSS REFERENCE TO RELATED APPLICATIONS

This application claims the benefit of U.S. Provisional Application No. 62/352,428, filed Jun. 20, 2016, which is hereby incorporated by reference in its entirety.

GOVERNMENTAL RIGHTS

This invention was made with government support under CMMI-1434786, DMR-1506219, and CHEM-1645015, awarded by National Science Foundation. The government has certain rights in the invention.

FIELD OF THE INVENTION

The present disclosure relates to compositions and methods for preparing engineered porous protein crystals comprising at least one guest molecule.

BACKGROUND OF THE INVENTION

Solvent channels and voids within protein crystals are widely used in classical protein crystallography for diffusion of biological ligands or heavy metals (to solve the phase problem). Heavy atom cluster soaks are particularly useful to solve the phase problem because they add many electrons. However, it is currently difficult to control the placement of biological or synthetic molecules in the solvent channels or voids within a protein crystal. This is exceedingly challenging due in part to the difficult and lengthy experiments necessary to elucidate the dynamic structure of proteins.

What is needed, therefore, are methods for controlling placement of molecules within the solvent channel or void spaces within a protein crystal.

SUMMARY OF THE INVENTION

One aspect of the present disclosure is directed to a composition comprising an engineered porous protein crystal and at least one guest molecule. The engineered porous protein crystal may have a pore size equal to or greater than 3 nm. The at least one guest molecule may comprise a metal nanoparticle, a biomacromolecule, or a combination thereof. In some aspects, the composition may comprise an engineered porous protein crystal may have a pore size is equal to or greater than 10 nm. In further aspects, the composition may comprise an engineered porous protein crystal may have a pore size is equal to or greater than 13 nm.

In some aspects, the engineered porous protein crystal may have covalent bonds between constituent molecules. In further aspects, the covalent bonds may be formed between two sulfhydryl containing amino acids. In other aspects, the covalent bonds may be the result of applying reactive aldehyde crosslinking agent. In still other aspects, the covalent bonds may be formed between a carboxylate containing amino acid and an amine containing amino acid using at least one cabodiimide crosslinking agent.

In some aspects, the engineered porous protein crystal may comprise at least one binding site within a pore. In some aspects, the binding site within the pore may be selected from the group consisting of an amino acid, a peptide sequences, and combinations thereof. In further aspects, the guest molecule may have a binding affinity to the binding site. The guest molecule may bind to the binding site within the engineered porous protein crystal.

In some aspects, the at least one guest molecule may be a nanoparticle. In further aspects, the nanoparticle may comprise at least one atom selected from the group consisting of Au, Ag, Cu, Pt, Pd, Ru, Fe, Cd, Se, Si, and Ni.

In some aspects, the at least one guest molecule may be a biomacromolecule. In further aspects, the biomacromolecule may be selected from the group consisting of a DNA sequence, an RNA sequence, a protein, and an enzyme.

In some aspects, the at least one guest molecule may further comprise a linker. In further aspects, the linker may comprise a chemical entity that binds a metal ion.

In further aspects, the porous protein crystal and the at least one guest molecule may be engineered to each have at least one metal-affinity motif. In further aspects, the at least one metal-affinity motif may consist of a peptide sequence comprising at least one histidine residue.

In some aspects, the porous protein crystal may be selected from a YCEI protein from *Campylobacter jejuni*, a pyridine nucleotide-disulfide family oxidoreductase from *Enterococcus faecalis*, a major tropism determinant P1 in complex with pertactin extracellular domain from *Bordetella bronchiseptica* and *Bordetella* virus bpp1, a putative cell adhesion protein (BACOVA_04980) from *Bacteroides ovatus*, Pyk2 (proline-rich tyrosine kinase 2) in complex with paxillin from *Gallus gallus*, and the NHR2 domain of the fusion protein AML1-ETO from *Homo sapiens*.

Another aspect of the present disclosure is directed to a method of preparing a porous protein crystal guest molecule conjugate. The method may comprise: obtaining a porous protein crystal, wherein the porous protein crystal has been reacted with a crosslinking agent to produce a crosslinked porous protein crystal and the crosslinking agent bonds adjacent monomers of the porous protein crystal; and incubating the crosslinked porous protein crystal with at least one guest molecule to produce a porous protein crystal guest molecule conjugate.

In some aspects, the method may further comprise incubating the porous protein crystal guest molecule conjugate with at least one metal ion to produce a stable porous protein crystal guest molecule conjugate. In further aspects, the at least one metal ion may be selected from the group consisting of Ni, Cu, Zn, Fe, and Co. In other aspects, the incubation of the porous protein crystal guest molecule conjugate with at least one metal ion may be from about 10 minutes to about 1 day. In further aspects, the incubation may be about 1 hour.

In some aspects, the engineered porous protein crystal may comprise at least one binding site within a pore. In some aspects, the binding site within the pore may be selected from the group consisting of an amino acid, a peptide sequences, and combinations thereof. In further aspects, the guest molecule may have a binding affinity to the binding site. The guest molecule may bind to the binding site within the engineered porous protein crystal.

In some aspects, the porous protein crystal and the at least one guest molecule used in the methods disclosed herein may be engineered to each have at least one metal-affinity motif. In further aspects, the at least one metal-affinity motif may consist of a peptide sequence comprising at least one histidine residue.

In some aspects, the crosslinking agent used in the methods disclosed herein may be selected from the group consisting of 1-Ethyl-3-[3-dimethylaminopropyl] carbodiimide hydrochloride (EDC); formaldehyde; formaldehyde, and urea, formaldehyde and guanidinium hydrochloride; glyoxal; glyoxal, and p-dimethylaminobenzaldehyde (DMAB); glutaraldehyde; glutaraldehyde and p-dimethylaminobenzaldehyde (DMAB); 1-Ethyl-3-[3-dimethylaminopropyl] carbodiimide hydrochloride (EDC); 1-Ethyl-3-[3-dimethylaminopropyl] carbodiimide hydrochloride (EDC) and imidazole; 1-Ethyl-3-[3-dimethylaminopropyl] carbodiimide hydrochloride (EDC) and N-hydroxysulfosuccinimide (Sulfo-NHS); or 1-Ethyl-3-[3-dimethylaminopropyl] carbodiimide hydrochloride (EDC) and malonic acid. In some aspects, the porous protein crystal may be reacted with a crosslinking agent from about 5 minutes to about 24 hours.

In some aspects, the at least one guest molecule used in the methods disclosed herein may comprise a metal nanoparticle. In further aspects, the metal nanoparticle may comprise at least one atom selected from the group consisting of Au, Ag, Cu, Pt, Pd, Ru, Fe, Cd, Zn, and Ni.

In some aspects, the at least one guest molecule used in the methods disclosed herein may be a biomacromolecule. In further aspects, the biomacromolecule may be selected from the group consisting of a DNA sequence, an RNA sequence, a protein, and an enzyme.

In some aspects, the at least one guest molecule used in the methods disclosed herein may comprise a linker. In further aspects, the linker may be a chemical entity that binds a metal ion.

In some aspects, the incubation of the guest molecule with the crosslinked porous protein crystal may be from about 1 minute to about 48 hours.

An additional aspect of the present disclosure is directed to a method of determining the structure of the guest molecule. The method may comprise: obtaining a porous protein crystal guest molecule conjugate, wherein the porous protein crystal guest molecule conjugate comprises a guest molecule and a porous protein crystal, wherein the porous protein crystal has been reacted with a crosslinking agent to produce a crosslinked porous protein crystal and the crosslinking agent crosslinks adjacent monomers of the porous protein crystal; and imaging the porous protein crystal guest molecule conjugate to determine the molecular structure of the at least one guest molecule. In some aspects, X-ray diffraction may be used to image the porous protein crystal guest molecule conjugate. In other aspects, the method may further comprise determining the molecular structure of the at least one guest molecule.

Still another aspect of the present disclosure is directed to a kit for determining the molecular structure of at least one guest molecule conjugated to an engineered porous protein crystal.

Other aspects and iterations of the disclosure are described in more detail below.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A) CJ crystals offer a hexagonal array of large axial pores. (FIG. 1B) The 13 nm diameter of these pores is much larger than the guest nanoparticles. (FIG. 1C and FIG. 1D) The host crystal can capture the guest nanoparticles via shared metal affinity.

FIG. 7A and FIG. 7B depict images of (i) CJ and (ii) CJΔH6 crystals. (FIG. 7A) At t=30 minutes in 1 mg/mL $Au_{25}$(GSH)$_{17}$NTA. (FIG. 7B) At t=1 hour in 0.1 M EDTA at pH 7.0. Both images were imaged with a 405 nm laser.

FIG. 8A and FIG. 8B depict images of a CJ crystal after the fifth repetition of loading (FIG. 8A) at t=30 minutes in 1 mg/mL $Au_{25}$(GSH)$_{17}$NTA and unloaded (FIG. 8B) at t=1 hour in 0.1 M EDTA at pH 7.0. Both images were imaged with a 405 nm laser.

(FIG. 9A) for simply diffusion, the concentration gradient just inside the host material decrease with time. (FIG. 9B) A CJ protein crystal was imaged by confocal laser microscopy while loading in 1 mg/mL $Au_{25}$(GSH)$_{17}$(NTA) for 2 hours. The gold nanoparticle concentration within the crystal was determined by comparing the fluorescence intensities of z-stack images to the fluorescence intensity standard curve used in FIG. 3. At 30 minutes, the concentration within the center of the crystal has reached that of the surrounding solution.

However, the concentration gradient just inside the crystal continues to increase with time. This indicates strong adsorption within the crystal pores; standard boundary conditions are inconsistent with the observed increases in surface concentration and increasing concentration gradient.

Figure 10A:
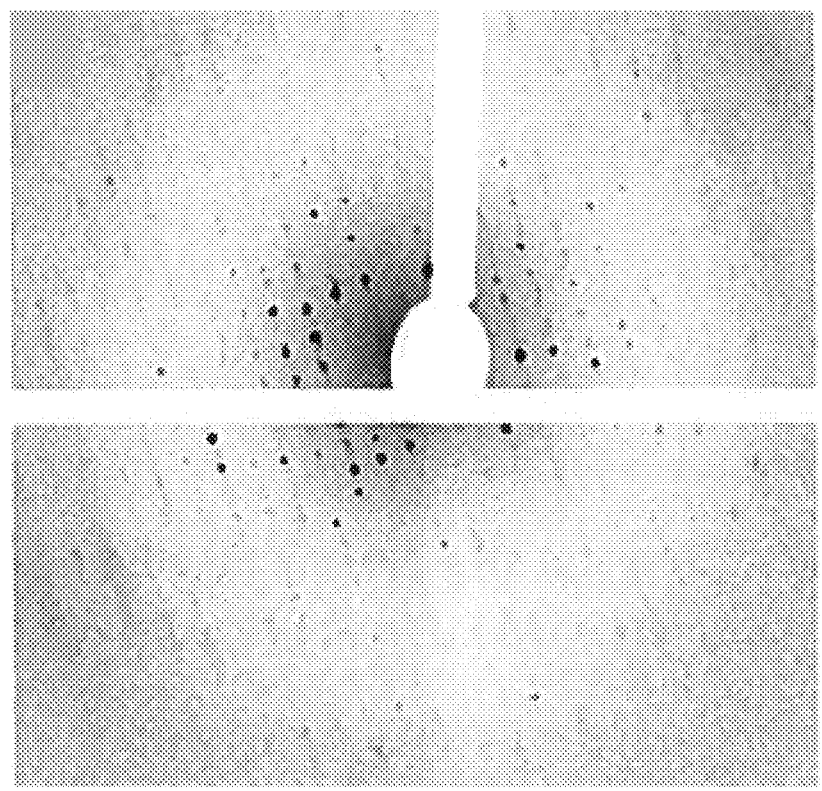
Figure 10B:
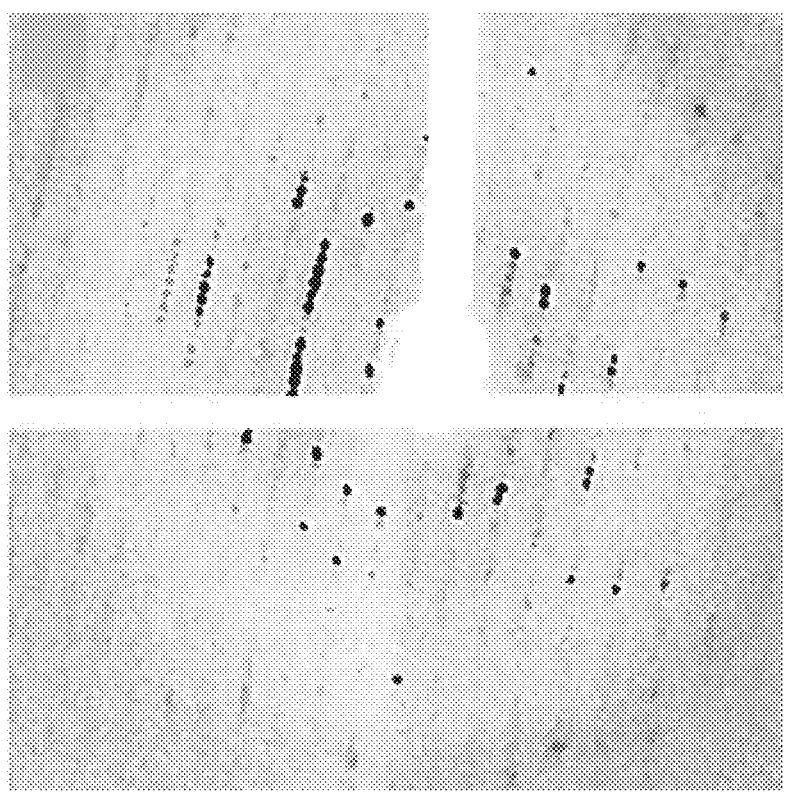

FIG. 10A and FIG. 10B depict X-ray diffraction images of a CJ crystal after incubation in (FIG. 10A) 1 mg/mL $Au_{25}(GSH)_{17}NTA$ for 30 minutes, followed by (FIG. 10B) 0.1 M EDTA at pH 7.0 for 30 minutes.

Figure 11:
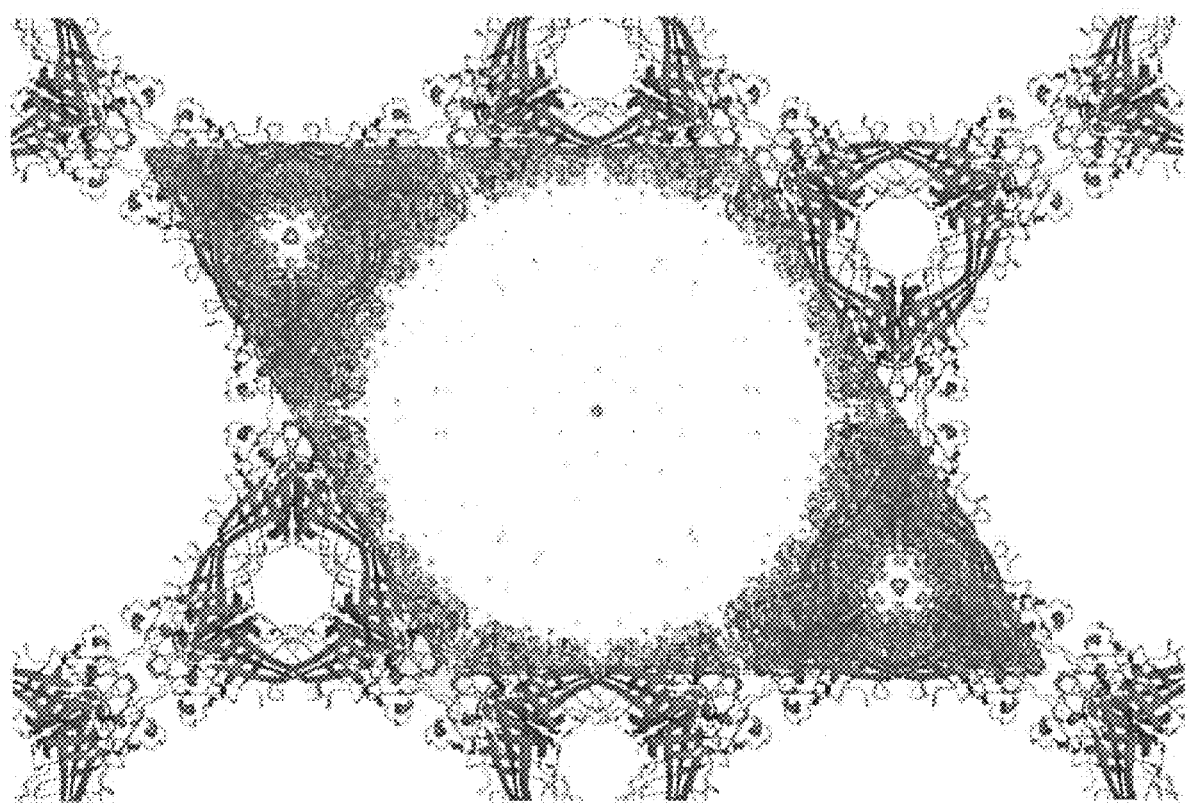

FIG. 11 depicts a $2F_o-F_c$ map contoured to 1 σ (blue) and $F_o-F_c$ difference map contoured to 3 σ (green) reveals no obvious preferred $Au_{25}(GSH)_{17}NTA$ binding sites in the crystal solvent pore after a 2 hour incubation.

Figure 12:
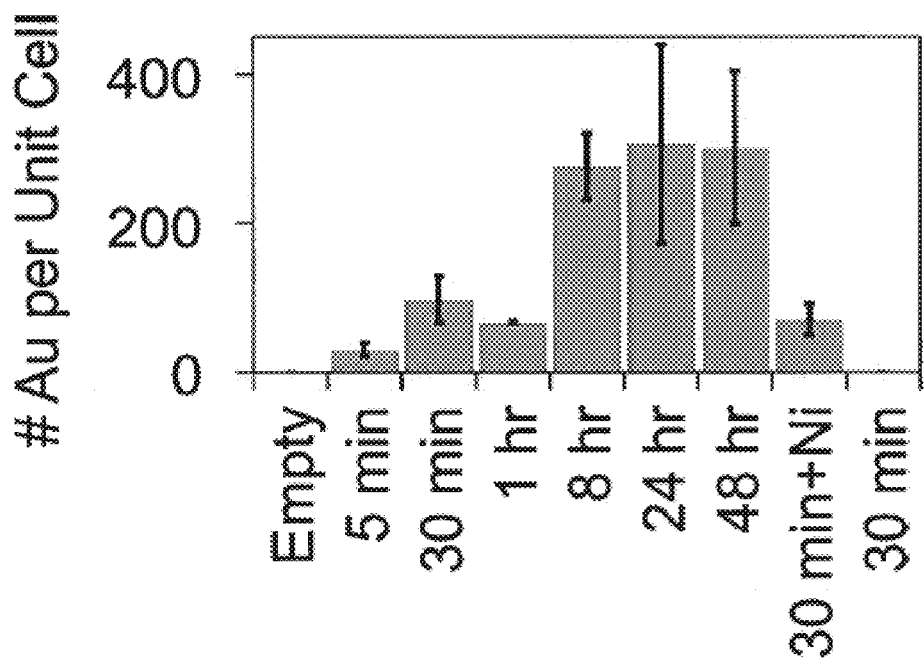

FIG. 12 depicts a graph showing the number of Au atoms per unit cell of crystals as determined by elemental analysis. In the first seven samples, crystals were loaded with gold nanoparticles for 5 minutes to 48 hours. The eighth sample shows the gold nanoparticles retained by the crystal after loading for 30 minutes and releasing in the presence of Ni(II) for 1 hour. The final sample shows the full removal of gold nanoparticles after loaded for 30 minutes and washing in the presence of EDTA for 1 hour.

Figure 13:
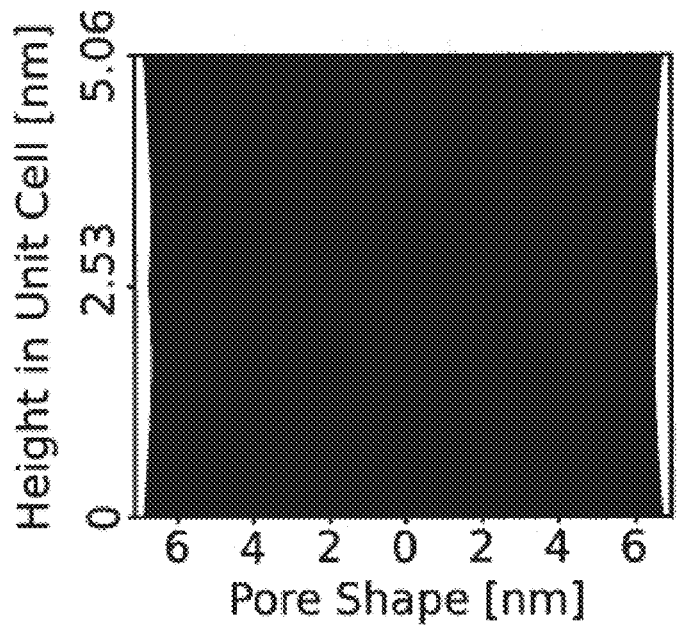

FIG. 13 depicts a graph showing the pore diameter varies only slightly along the z-axis (13.1 to 13.6 nm). From any point along the pore center line, the minimum distance to a heavy atom in the protein crystal (including z-axis periodicity) is 6.57 nm.

Figure 14:
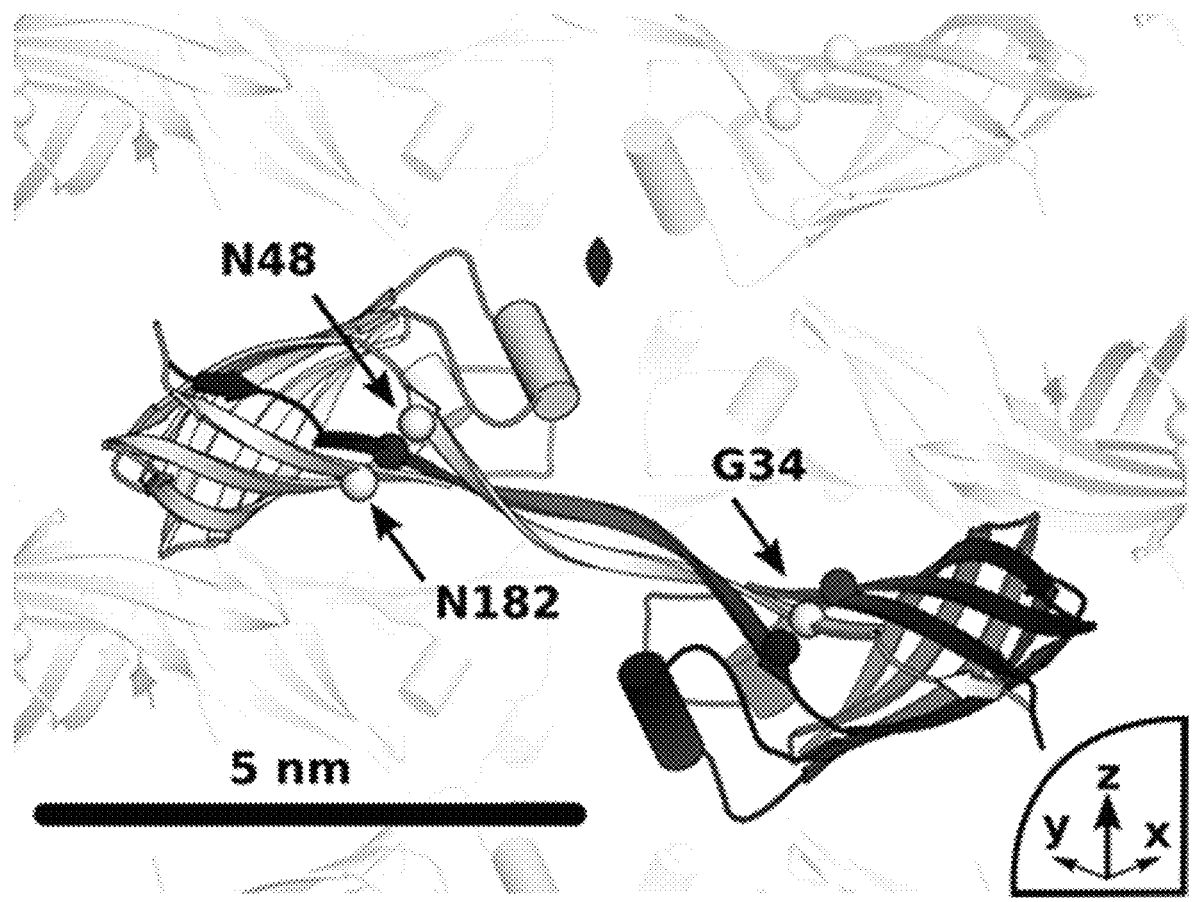

FIG. 14 depicts candidate thiol mutation sites (spheres) selected for maximal inter-site distance and accessibility to the large axial pore (~13 nm). A surface cleft presented three candidate mutation sites, G34C, N48C, N182C.

Figure 15:
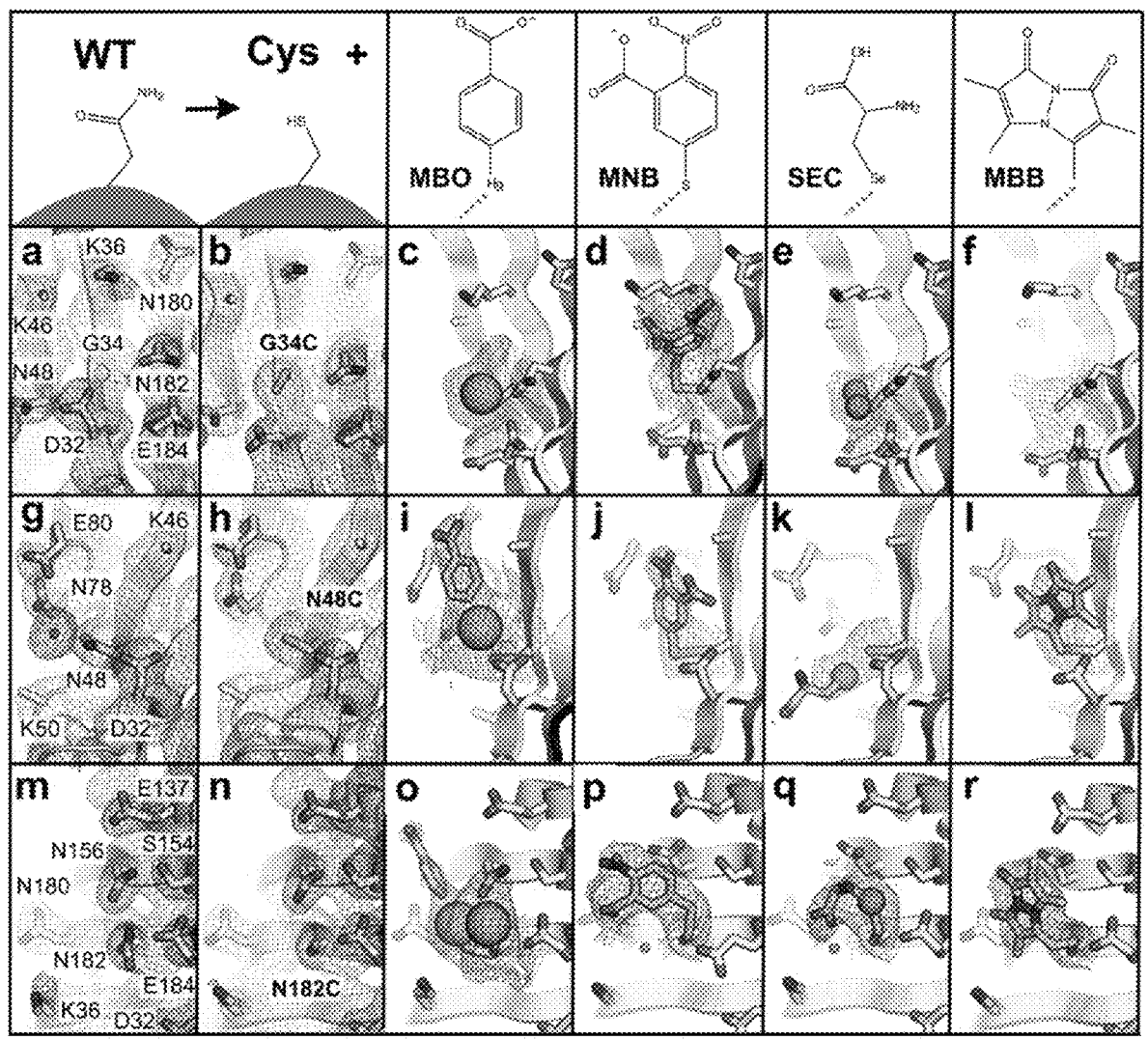

FIG. 15 depicts $2mF_o-DF_c$ maps contoured to 0.8 σ centered at G34 for (panel a) CJ wild-type (G34 alpha carbon marked with a sphere) and (panel b) G34C. (panel c) A single mercury position for 5-mercapto-2-nitro-benzoic acid (panel d) MNB at 100% occupancy was modeled after addition of Ellman's reagent to G34C. (panel e) Two 50%-occupancy selenium positions for selenocysteine (SEC) were modeled. (panel f) Despite hints in the electron density, we did not place mBBr; $2mF_o-F_c$ maps contoured to 0.8 σ centered at N48 for (panel g) CJ wild-type and (panel h) N48C. (panel i) A single 85%-occupancy conformation was modeled for 2-hydroxymercuribenzoic acid (MBO). (panel j) A single conformation for 5-mercapto-2-nitro-benzoic acid (MNB) at 100% occupancy was modeled. (panel k) A single conformation at 90% occupancy for selenocysteine (SEC) was modeled though part of the SEC adduct was not resolved. (panel l) A single conformation at 90% for a bimane ligand (MBB) was modeled; $2mF_o-DF_c$ maps contoured to 0.8 a centered at N182 for (panel m) CJ wild-type and (panel n) N182C. (panel o) Two 50%-occupancy conformations were modeled for 2-hydroxymercuribenzoic acid (MBO). (panel p) A single 100%-occupancy conformation for 5-mercapto-2-nitro-benzoic acid (MNB) was modeled. (panel q) A single conformation at 100% occupancy for selenocysteine (SEC) was resolved. (panel r) A single conformation at 100% for the bimane adduct (MBB) was modeled.

Figure 16:
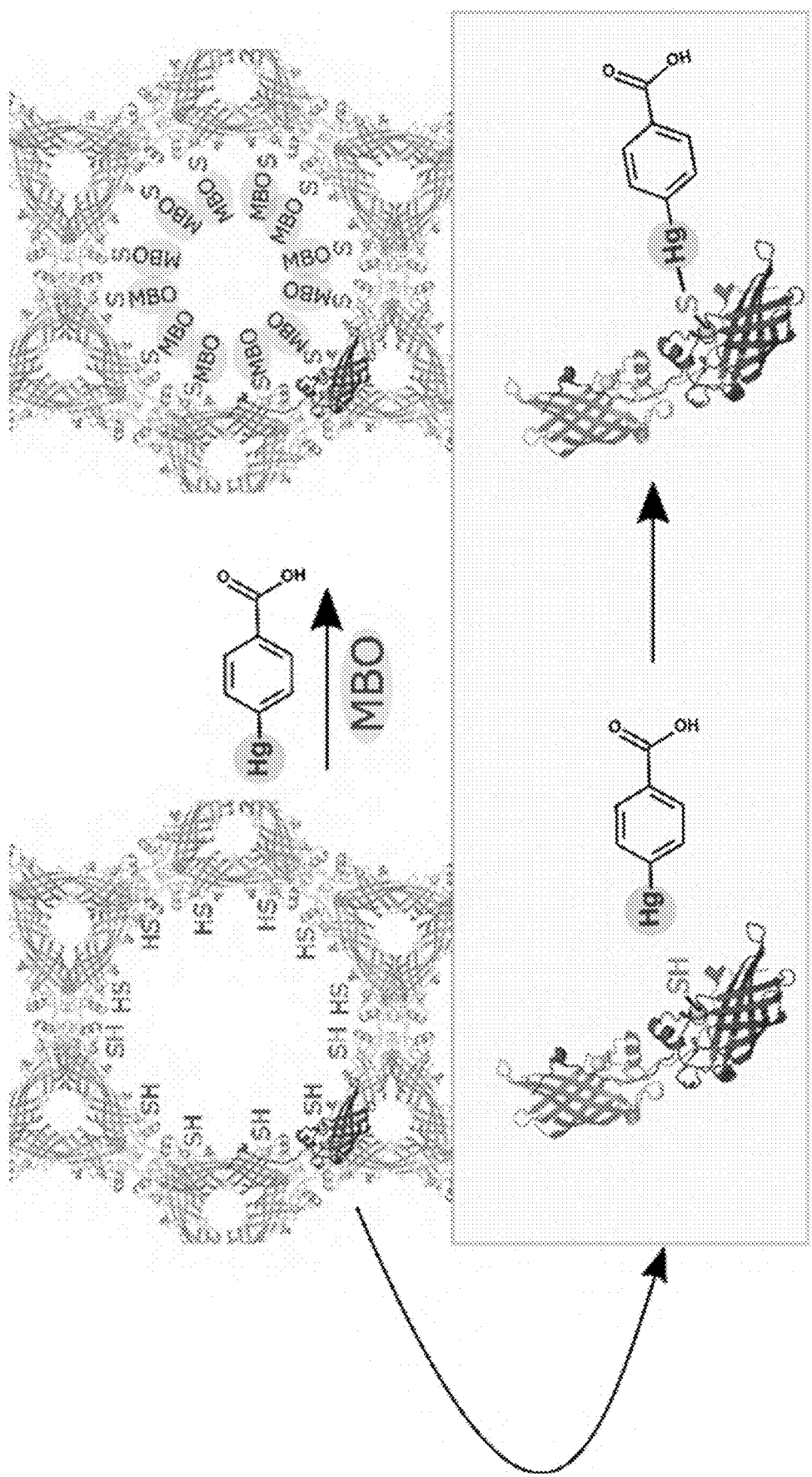

FIG. 16 illustrates a reaction between mercuribenzoic acid (MBO) and CJ cysteine residues to demonstrate the accessibility of the engineered cysteines to the solvent channels and ability to be derivatized with heavy atoms.

Figure 17:
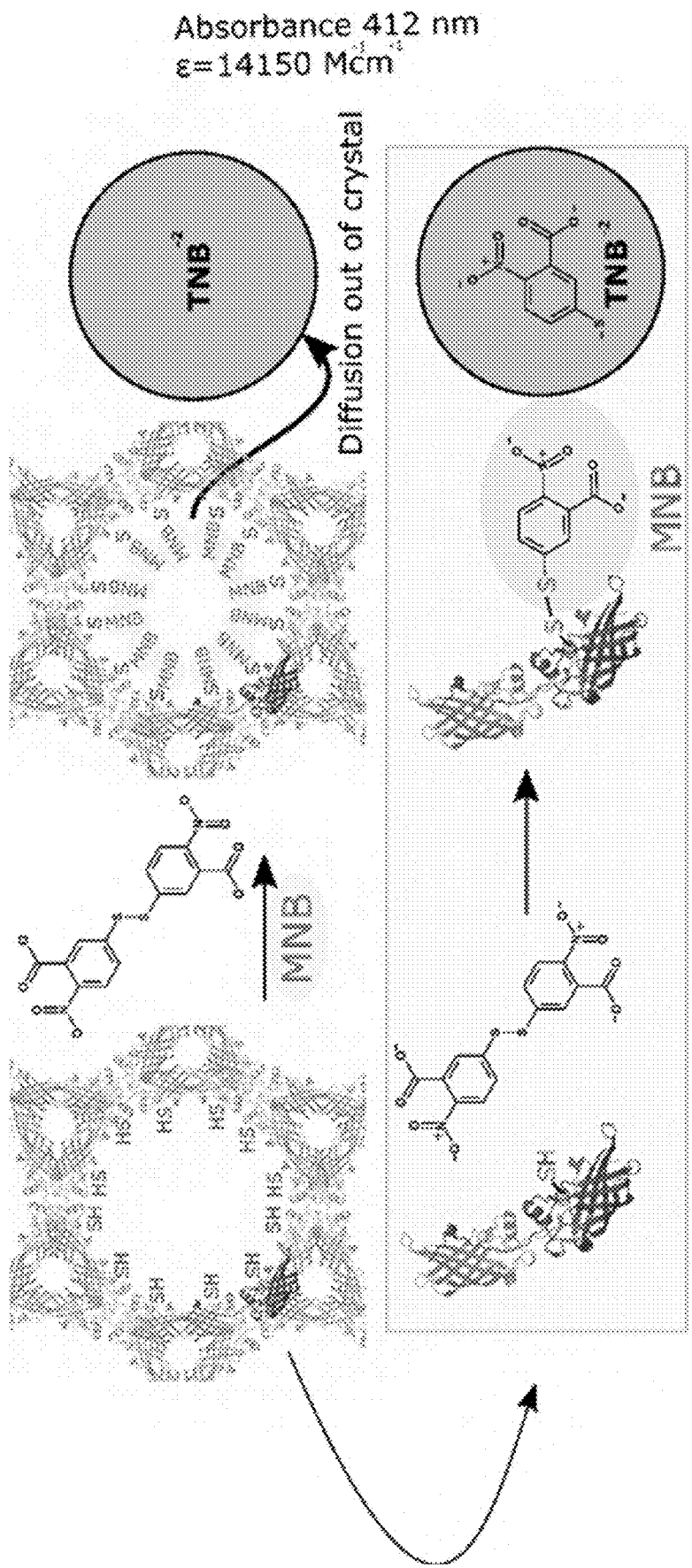

FIG. 17 illustrates an SN2 reaction between Ellman's reagent (5,5'-dithio-bis-[2-nitrobenzoic acid]) and thiols that forms a mixed disulfide product with the addition of 5-mercapto-2-nitro-benzoic acid (MNB) to reduced thiols. The reaction can be monitored by measuring the release of 2-nitro-5-thiobenzoate anion ($TNB^{-2}$) which absorbs strongly at 412 nm. These properties made Ellman's reagent an attractive choice for demonstrating disulfide exchange in CJ cysteine mutant crystals.

Figure 18A:
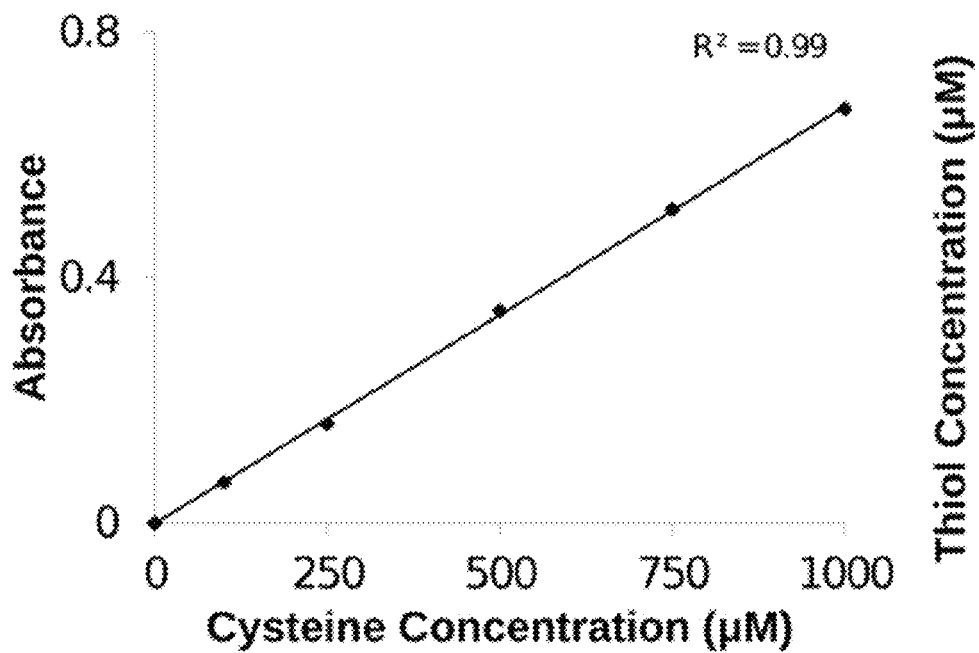
Figure 18B:
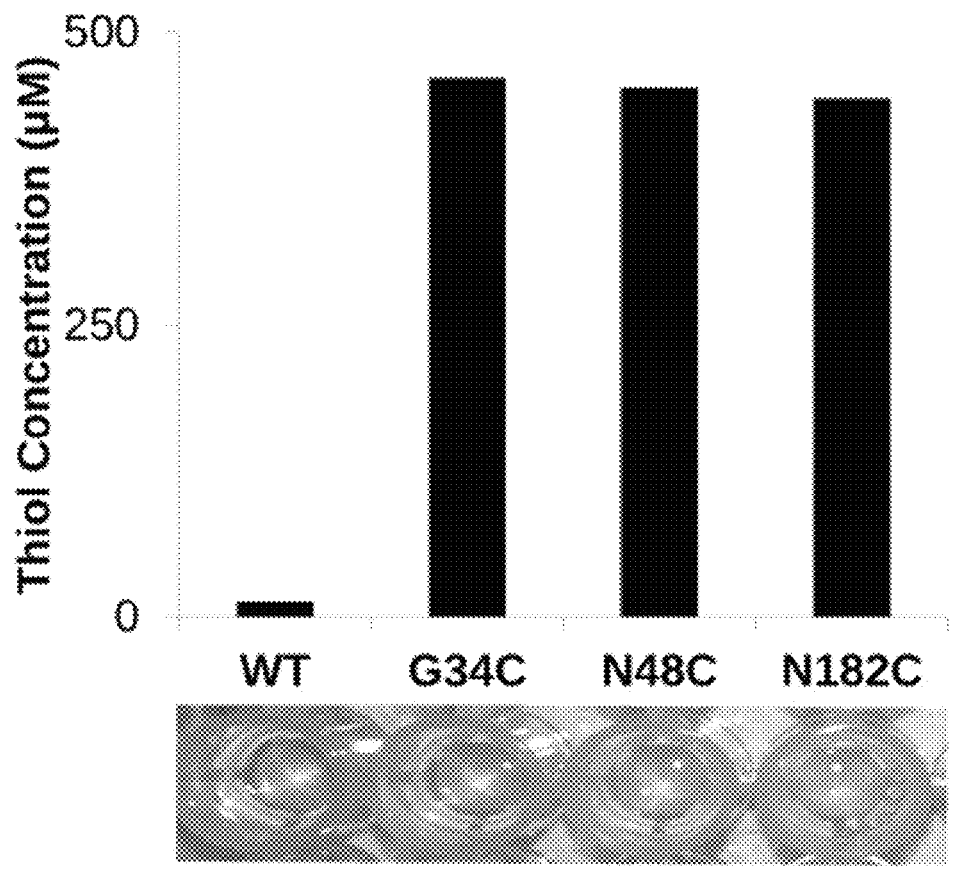

FIG. 18A and FIG. 18B illustrate that thiol concentration in solution can be measured by addition of Ellman's reagent and measuring absorbance 412 nm. (FIG. 18A) An in vitro Ellman's Reagent standard curve was prepared for reduced L-cysteine from 0-1000 μM. (FIG. 18B) Purified CJ-variants were diluted to ~10 mg/mL (~500 μM) and Ellman's reagent was added to confirm the presence and accessibility of thiols in solution. Only CJ-variants with engineered cysteines produced a signal at 412 nm.

Figure 19:
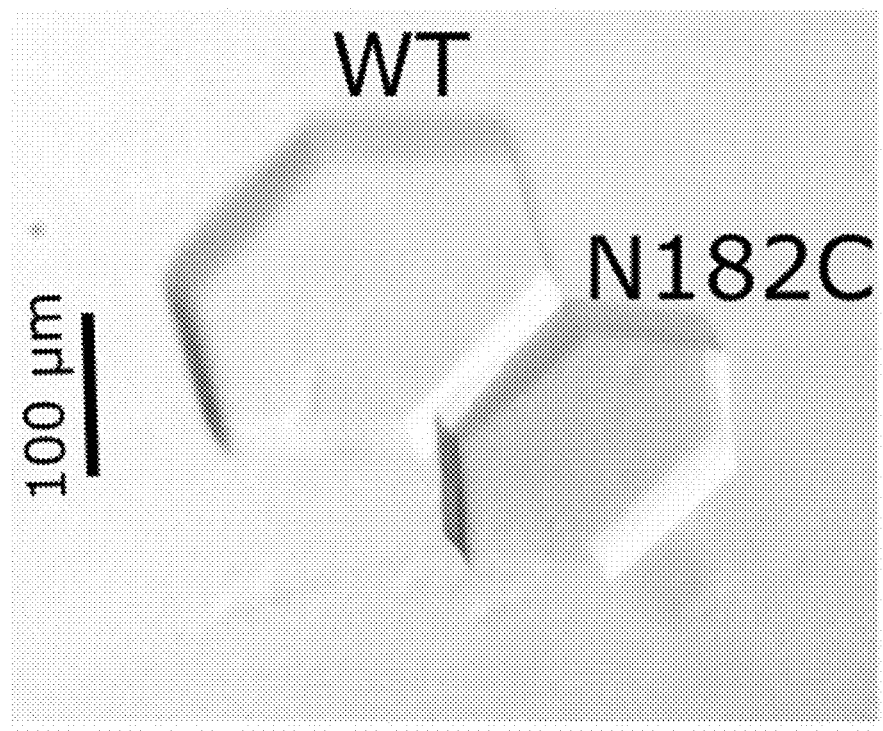

FIG. 19 depicts images of wild-type and CJ cysteine mutant crystals exposed to Ellman's reagent and extensively washed to remove unreacted Ellman's reagent. Addition of 2-mercaptoethanol (BME) produced an intense yellow signal only on CJ cysteine mutant crystals, indicating installation of 5-mercapto-2-nitro-benzioc benzoic acid (MNB) on the engineered cysteines.

Figure 20:
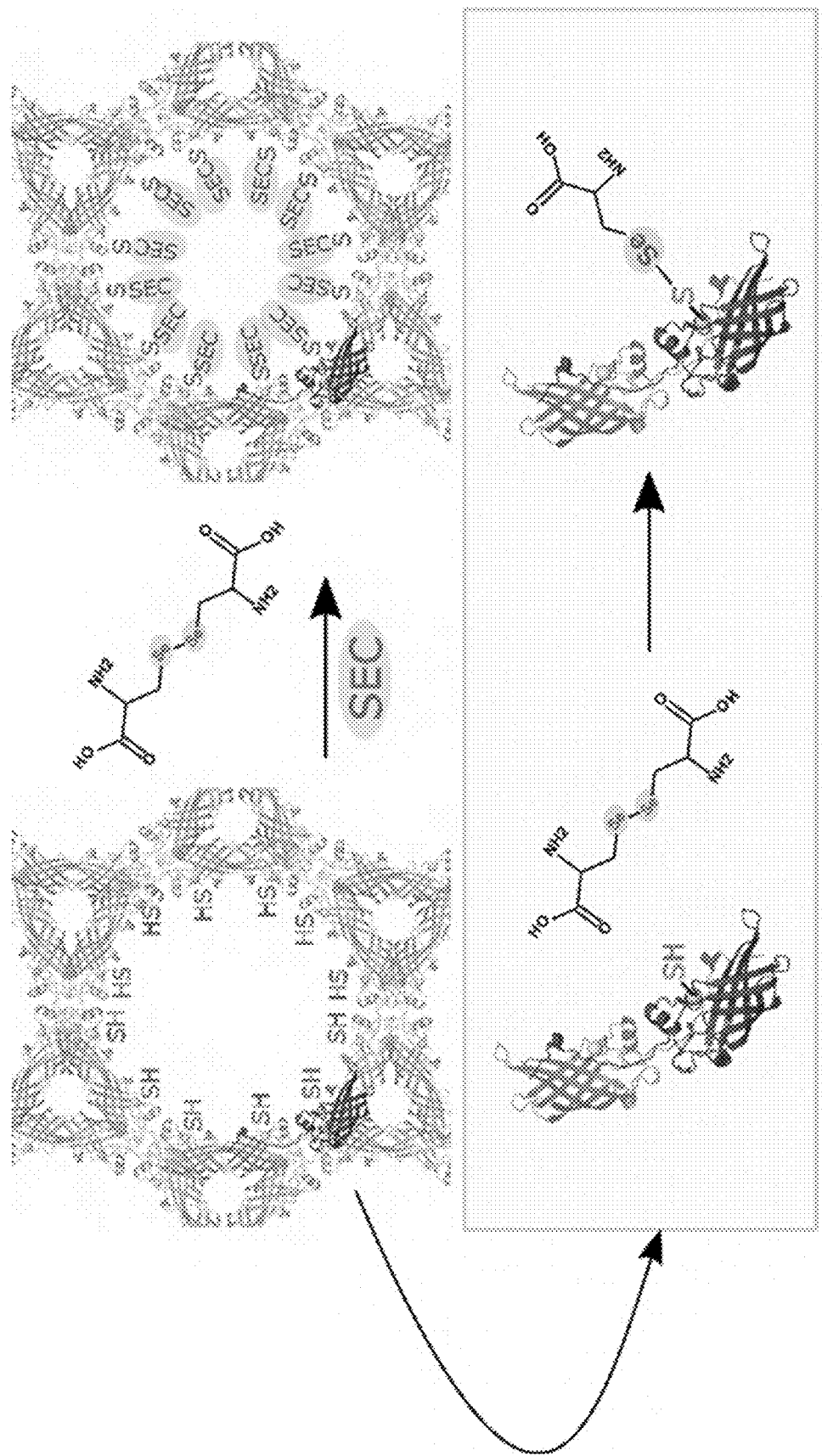

FIG. 20 illustrates a reaction analogous to disulfide exchange, thiols can form mixed oxidized products with diselenide compounds. The reaction of thiols with diselenides has the benefit of addition a heavy atom at the attachment point, useful for derivatization. More specifically, selenocystine is reacted with cysteine residues in the CJ crystals to produce selenocysteine (SEC).

Figure 21:
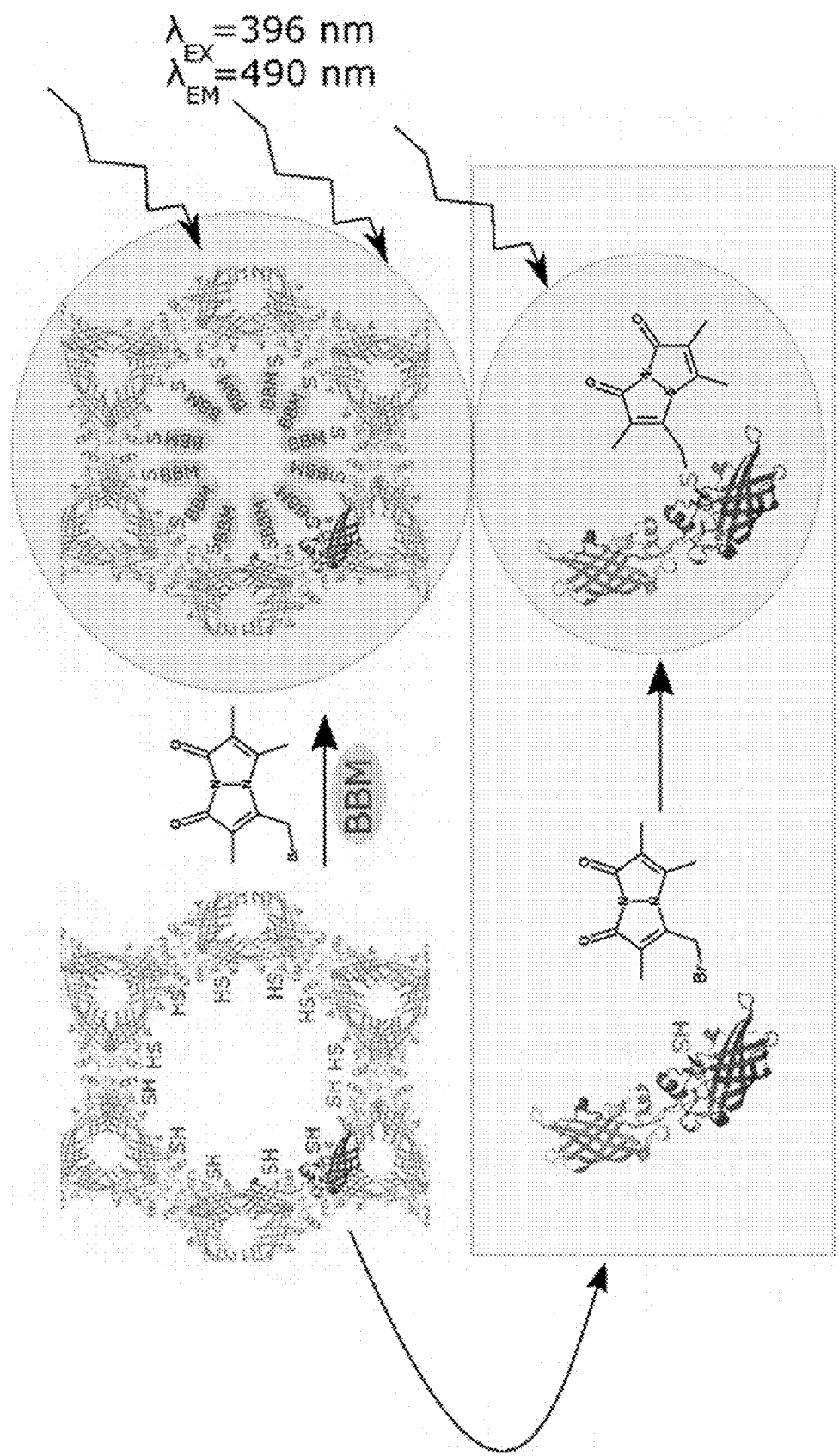

FIG. 21 illustrates an SN2 reaction between a haloalkyl and a thiol that forms a stable thioether linkage. More specifically, monobromobimane (mBBr) is reacted with cysteine residues in the CJ crystals. mBBr is essentially non-fluorescent until forming the resulting bimane (BBM) conjugate.

Figure 22A:
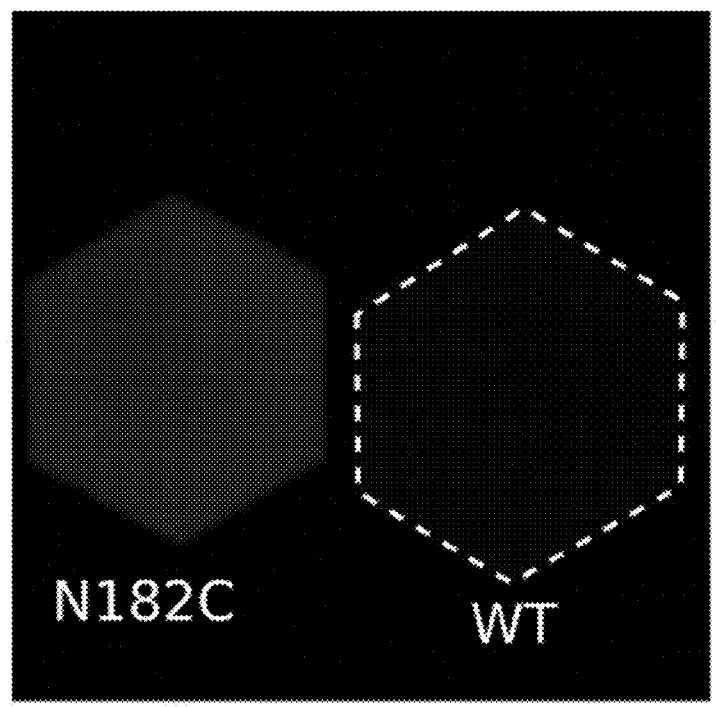
Figure 22B:
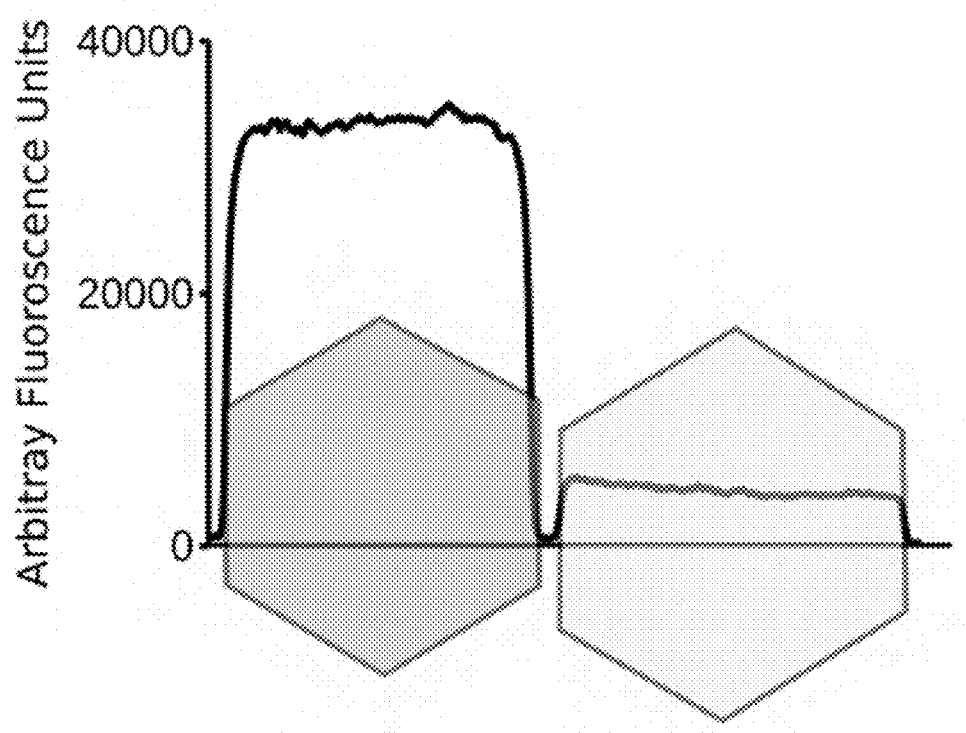

FIG. 22A depicts confocal microscopy images ($\lambda_{EX}$=405 nm) of CJ wild-type (WT) and N48C after exposure to monobromobimane. N48C is fluorescent indicative of monobromobimane installation and FIG. 22B depicts raw pixel values for N48C and WT show that monobromobimane was selectively installed on the engineered cysteine.

Figure 23A:
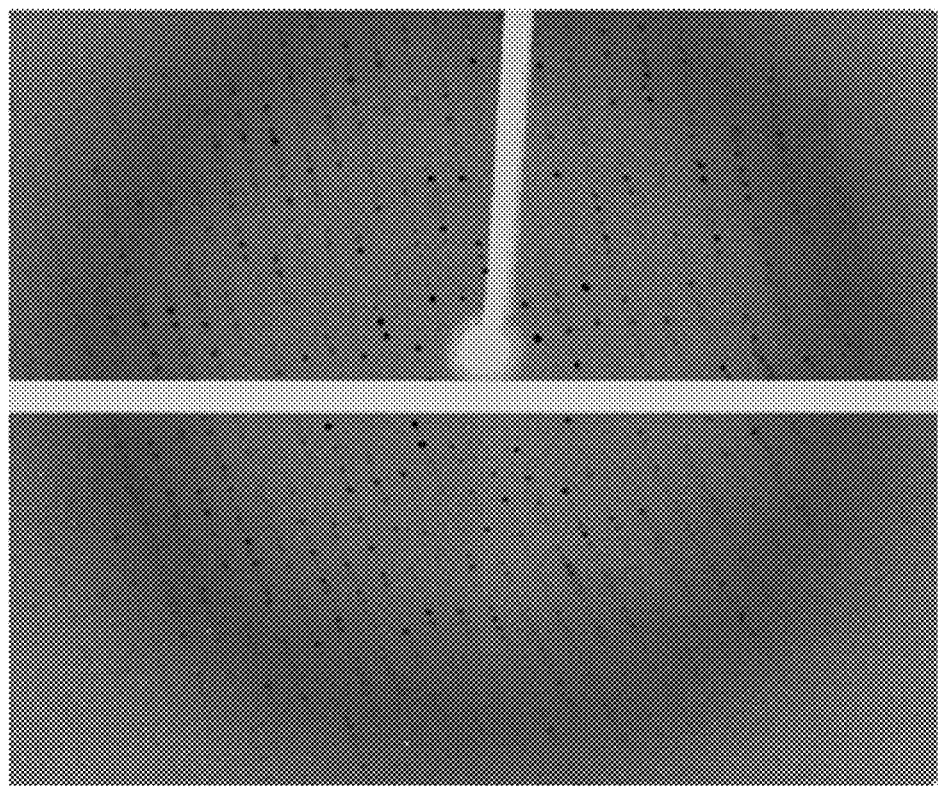
Figure 23B:
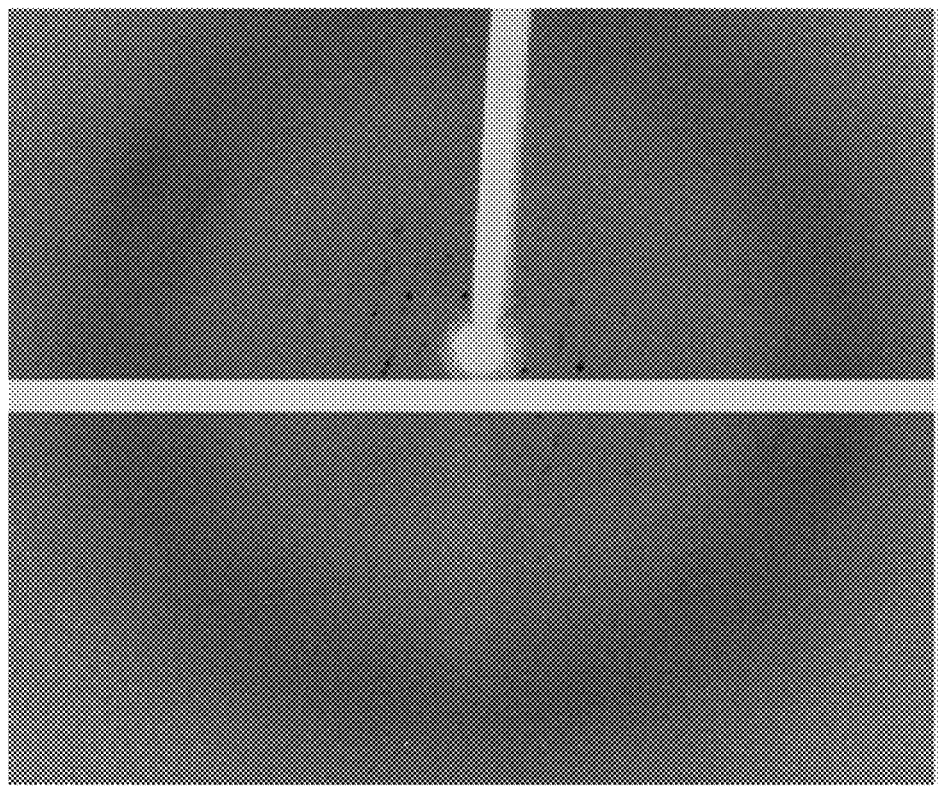

FIG. 23A and FIG. 23B depict XRD patterns, illustrating the best diffraction for (FIG. 23A) formaldehyde/urea at 0.5 hours and (FIG. 23B) the poorest diffraction for glutaraldehyde at 0.5 hours. In both cases, the crystal was transferred from the high-salt mother liquor to the challenging condition: 50% aqueous glycerol.

Figure 24A:
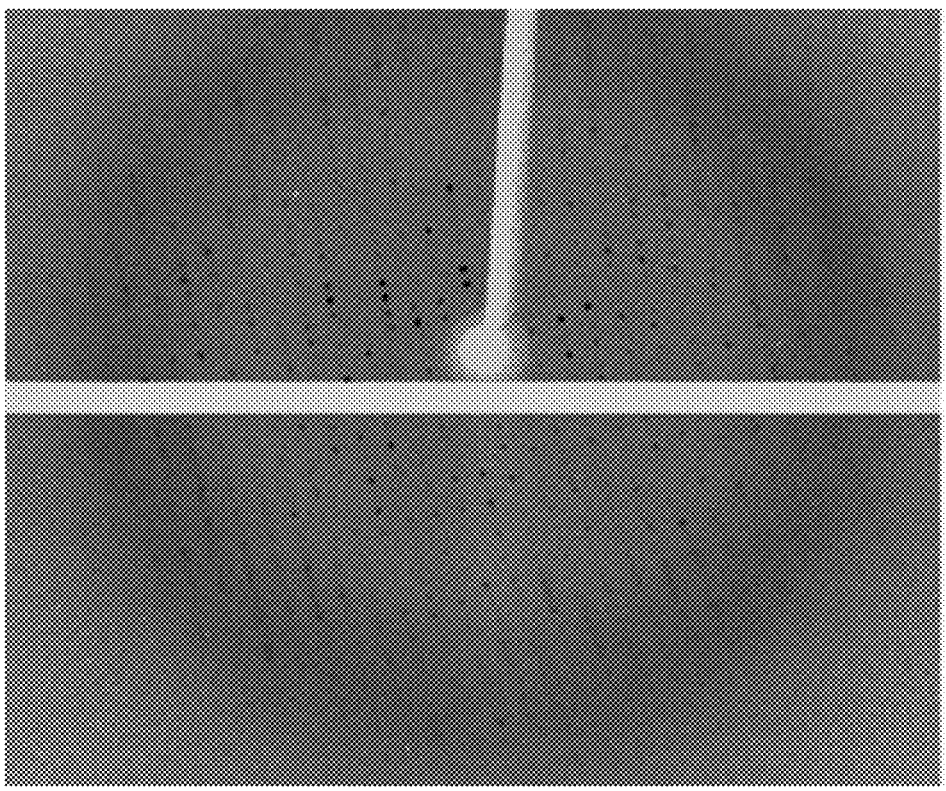
Figure 24B:
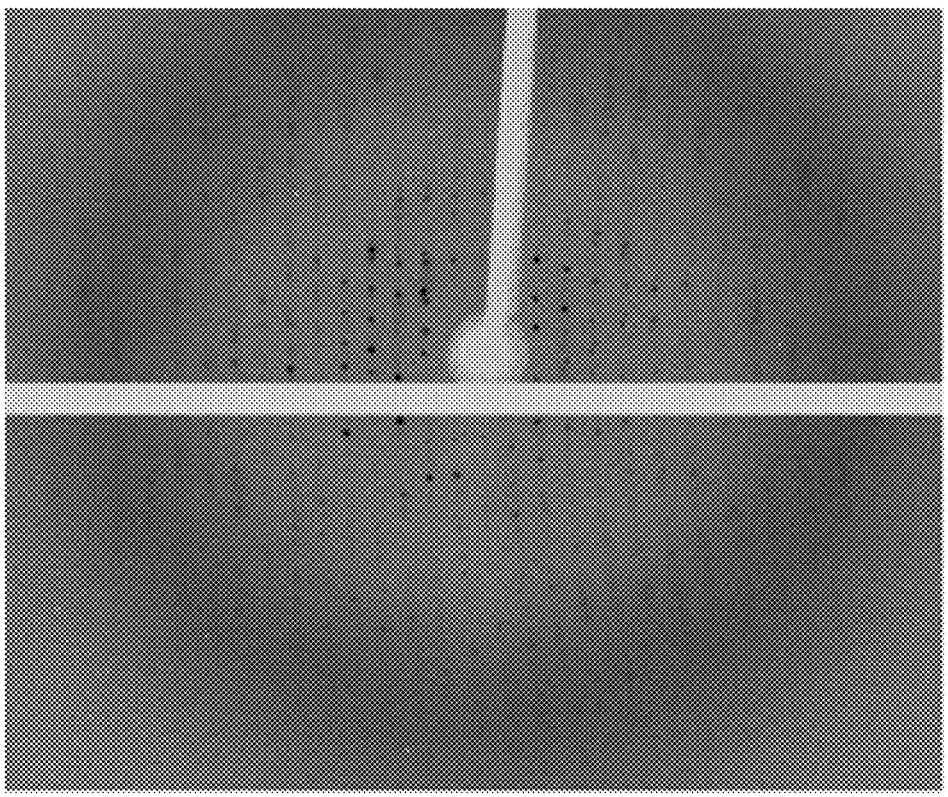

FIG. 24A and FIG. 24B depict XRD patterns, illustrating the best diffraction for (FIG. 24A) EDC-imidazole at 2 hours and (FIG. 24B) the poorest diffraction for EDC-imidazole at 2 hours. In both cases, the crystal was transferred from the high-salt mother liquor to the challenging condition: 50% aqueous glycerol.

DETAILED DESCRIPTION OF THE INVENTION

Provided herein are compositions and methods for preparing a porous protein crystal guest molecule conjugate. Suitable compositions and methods for preparing a porous protein crystal guest molecule conjugates are detailed below.

(I) Porous Protein Crystal

One aspect of the present disclosure encompasses a 3-dimensional porous protein crystal. In general, the porous protein crystal comprises at least one protein monomer that assembles to form multiple unit cells, with each unit cell capable of hosting at least one guest molecule.

(a) Protein Identity

In general, the porous protein crystal comprises a protein. Proteins that are able to crystalize into a protein scaffold with an appropriate pore size are known by those of skill in the art. A person skilled in the art would be able to inspect the known crystal packing arrangement for proteins deposited in the Research Collaboratory for Structural Bioinformatics Protein Data Bank (RCSB PDB) (Berman H M, Westbrook J, Feng Z, Gilliland G, Bhat T, Weissig H, et al. The protein data bank. *Nucleic Acids Research,* 2000; 28(1): 235-242, herein incorporated by reference in its entirety). A person skilled in the art could then select a protein crystal known to crystallize into a protein scaffold with an appropriate pore size.

In some embodiments, the protein may be the NHR2 domain of the fusion protein AML1-ETO from *Homo sapiens*, chloramphenicol phosphotransferase from *Streptomyes venezuelae*, gastric lipase from *Homo sapiens*, a Bro1 domain containing protein Brox from *Homo sapiens*, a putative cell adhesion protein (BACOVA_04980) from *Bacteroides ovatus*, glycoprotein 1 b from *Homo sapiens*, an arginine decarboxylase SpeA from *Campylobacter jejuni*, a cystathionine beta-synthase from *Homo sapiens*, a (+)-bornyl diphosphate synthase from *Salvia officinalis*, a measles virus hemagglutinin bound to its cellular receptor SLAM (form I) from *Saguinus oedipus*, an invertase 2 from *Saccharomyces cerevisiae*, a putative periplasmic YCEI-like protein from *Campylobacter jejuni*, an atrial natriuretic peptide clearance receptor from *Homo sapiens*, a catalytic domain of transaminase PigE from *Serratia sp. fs14*, a putative glycosidase from *Thermotoga maritima*, a sorting nexin 10 from *Homo sapiens*, photosystem I from *Synechococcus elongatus*, lysostaphin from *Staphlococcus simulans*, Pyk2 (proline-rich tyrosine kinase 2) in complex with paxillin from *Gallus gallus*, an Insulin degrading enzyme from *Homo sapiens*, an artocarpin from *Artocarpus integer*, a neuropilin-1 extracellular domains from *Mus musculus*, a tryptophanyl-tRNA synthetase from *Saccharomyces cerevisiae*, DNA topoisomerase II from *Escherichia coli*, a V delta 1 T Cell Receptor in complex with antigen-presenting glycoprotein CD1d from *Homo sapiens*, a *Mus musculus* antibody-bound *Homo sapiens* Prolactin receptor, a fructose 1-6-bisphosphate aldolase from *Homo sapiens*, a core fragment from unphosphorylated STAT3 (signal transducer and activator of transcription 3) from *Mus musculus*, a fusion glycoprotein F0 from Human metapneumovirus and neutralizing antibody DS7 from *Homo sapiens*, a growth-arrest-specific protein 6 precursor and tyrosine-protein kinase receptor UFO from *Homo sapiens*, a Sas-6 cartwheel hub from *Leishmania major*, a neuraminidase from Influenza a virus, a molybdopterin-guanine dinucleotide biosynthesis protein B from *Escherichia coli*, an apical membrane antigen AMA1 and putative Rhoptry neck protein 2 from *Eimeria tenella*, a complex between NADPH-cytochrome P450 reductase and heme oxygenase 1 from *Rattus norvegicus*, a proprotein convertase subtilisin/kexin type 9 in complex with low-density lipoprotein receptor from *Homo sapiens*, a major tropism determinant P1 in complex with pertactin extracellular domain from *Bordetella bronchiseptica* and *Bordetella* virus bpp1.

In an embodiment, the protein may be a constituent of the following Protein Data Bank entries: 3FOQ, 4JOL, 4O9X, 1QHN, 1R5U, 1S49, 3S4Z, 3AL8, 2BDM, 3C3E, 3EN1, 1 IVI, 1 MHP, 3RIP, 1 EA0, 4FHM, 3GB8, 1HLG, 4O5I, 3R9M, 3ZXU, 3ABS, 1S4F, 3UF1, 1V3D, 1WCM, 4CNI, 3Q17, 3RZI, 2BE5, 1GWB, 4MNA, 3NZP, 1OGP, 3FCU, 3K7A, 4L3V, 1N21, 4U7P, 3ALZ, 1RLR, 4EQV, 2FGS, 1JDN, 4MQ9, 4PPM, 3QZ2, 3WOD, 2AAM, 4AY5, 4IW0, 3K1F, 4PZG, 3PCQ, 2QUK, 3RJ1, 3W3A, 3ALW, 4AY6, 4LXC, 4O5J, 4R32, 2WBY, 1ZBU, 3A5C, 4J23, 4AVT, 1TYE, 1VBP, 4GZ9, 4WJW, 4C8Q, 2YHB, 3DQQ, 3KT8, 1 D6M, 4MNG, 2TMA, 4I18, 1QO5, 3CWG, 4DAG, 3D38, 2C5D, 4CKP, 3CL2, 1P9N, 4YIZ, 3WKT, 3P5C, and 2IOU.

In an exemplified embodiment, the protein may be a YCEI protein from *Campylobacter jejuni*, a pyridine nucleotide-disulfide family oxidoreductase from *Enterococcus faecalis*, a major tropism determinant P1 in complex with pertactin extracellular domain from *Bordetella bronchiseptica* and *Bordetella* virus bpp1, a putative cell adhesion protein (BACOVA_04980) from *Bacteroides ovatus*, Pyk2 (proline-rich tyrosine kinase 2) in complex with paxillin from *Gallus gallus*, and the NHR2 domain of the fusion protein AML1-ETO from *Homo sapiens*.

(b) Protein Crystallization

In general, the protein is crystallized to form a porous protein crystal. The porous protein crystal comprises multiple unit cells.

In general, the protein may be crystallized using standard techniques in the field. Further, the method can and will vary depending on the identity of the protein. Suitable methods include, without limit, vapor diffusion, sitting drop, hanging drop, counter-diffusion, batch, microbatch, microdialysis, free-interface diffusion, and seeding (Weber P. C., Overview of protein crystallization methods. *Methods Enzymology,* 1997; 276:13-22, herein incorporated by reference in its entirety).

Briefly, protein crystallization is influenced by purities and concentrations of the protein, the types and concentrations of protein crystallization agents, pH conditions, temperature conditions, etc. Therefore, protein crystallization conditions are determined according to a combination of these parameters. Specifically, screening of protein crystallization conditions refers to selecting, from the multiple combinations of the parameters above, the combination of parameters suitable for crystallization of a target protein. Protein crystallization conditions are reported for structures present in the PDB. Thus, a person skilled in the art would be able to recapitulate known protein crystal forms by conducting crystallization experiments that emulate the published conditions.

(c) Protein Crystal Pore Diameter

In general, the porous protein crystal comprises a plurality of pores or solvent channels. These pores or solvent channels allow for entry of the guest molecule into the porous protein crystal. Once the guest molecule has entered the porous protein crystal it may then bind to at least one binding site within the pore of the porous protein crystal. The pores should be an appropriate size to allow entry of the guest molecule.

In an embodiment, the porous protein crystal may have a pore diameter of from about 3 nm to about 50 nm. In some embodiments, the pore diameter may be about 3 nm, about 4 nm, about 5 nm, about 6 nm, about 7 nm, about 8 nm, about 9 nm, about 10 nm, about 15 nm, about 20 nm, about 25 nm, about 30 nm, about 35 nm, about 40 nm, about 45 nm, or about 50 nm. In additional embodiments, the pore diameter may be equal to or greater than about 4 nm, equal to or greater than about 5 nm, equal to or greater than about 6 nm, equal to or greater than about 7 nm, equal to or greater than about 8 nm, equal to or greater than about 9 nm, equal to or greater than about 10 nm, equal to or greater than about 11 nm, equal to or greater than about 12 nm, equal to or greater than about 13 nm, equal to or greater than about 14 nm, equal to or greater than about 15 nm, equal to or greater than about 16 nm, equal to or greater than about 17 nm, equal to or greater than about 18 nm, equal to or greater than about 19 nm, equal to or greater than about 20 nm, equal to or greater than about 21 nm, equal to or greater than about 22 nm, equal to or greater than about 23 nm, equal to or greater than about 24 nm, equal to or greater than about 25 nm, equal to or greater than about 26 nm, equal to or greater than about 27 nm, equal to or greater than about 28 nm, equal to or greater than about 29 nm, or equal to or greater than about 30 nm.

In an embodiment, the plurality of pores may have an average diameter of from about 3 nm to about 50 nm. In some embodiments, the plurality of pores may have an average diameter of about 3 nm, about 4 nm, about 5 nm, about 6 nm, about 7 nm, about 8 nm, about 9 nm, about 10 nm, about 15 nm, about 20 nm, about 25 nm, about 30 nm, about 35 nm, about 40 nm, about 45 nm, or about 50 nm. In additional embodiments, the plurality of pores may have an average diameter equal to or greater than about 4 nm, equal to or greater than about 5 nm, equal to or greater than about 6 nm, equal to or greater than about 7 nm, equal to or greater than about 8 nm, equal to or greater than about 9 nm, equal to or greater than about 10 nm, equal to or greater than about 11 nm, equal to or greater than about 12 nm, equal to or greater than 13 nm, equal to or greater than about 14 nm, equal to or greater than about 15 nm, equal to or greater than about 16 nm, equal to or greater than about 17 nm, equal to or greater than about 18 nm, equal to or greater than about 19 nm, equal to or greater than about 20 nm, equal to or greater than about 21 nm, equal to or greater than about 22 nm, equal to or greater than about 23 nm, equal to or greater than about 24 nm, equal to or greater than about 25 nm, equal to or greater than about 26 nm, equal to or greater than about 27 nm, equal to or greater than about 28 nm, equal to or greater than about 29 nm, or equal to or greater than about 30 nm.

(d) Protein Binding Site

In general, the porous protein crystal comprises at least one binding site within a pore to allow at least one guest molecule to bind. In an embodiment, the at least one binding site may be an amino acid, a chemically modified amino acid, a proximal collection of amino acids, a peptide sequence, or combinations thereof.

In some embodiments, the protein binding site may be designed so the binding between it and the guest molecule is reversible. In other words, the guest molecule may be released from the binding site. Release from the binding site may result when the porous protein crystal guest molecule conjugate is exposed to a specific condition (i.e., solvent, temperature, light, electric field, magnetic field, etc.). By way of a non-limiting example, the guest molecule may be a nanoparticle that may be released from the porous protein crystal by exposure to a solvent, which breaks the specific porous protein/nanoparticle interaction.

(i) Naturally Occurring Amino Acids

In an embodiment, the at least one binding site may be an amino acid. In a preferred embodiment, the amino acid may be histidine and cysteine. Other canonical amino acids may be selectively modified by a variety of reagents. Modifying agents are provided in Hermanson, G. T. *Bioconjugate Techniques*. (Academic Press, 2013), herein incorporated by reference in its entirety. The at least one binding site may be engineered or modified (i.e., substitution mutation) to be at a specific location within the pore to direct the guest molecule to occupy a specific location with the pore.

(ii) Non-Canonical Amino Acids

In an embodiment, the at least one binding site may be a non-canonical amino acid. In some embodiments, the non-canonical amino acids would be capable of "click chemistry." Suitable non-canonical amino acids may comprise akynes, azides, or tetrazines.

(iii) Chemically Modified Amino Acids

In an embodiment, the at least one binding site may be a chemically modified amino acid. Suitable amino acids for chemical modification may include cysteine, lysine, histidine, tyrosine, serine, arginine, aspartic acid, glutamic acid, and tryptophan. In an embodiment, the amino acid may be modified by a modifying agent.

Suitable modifying agents may include, without limit, Ellman's reagent (i.e., 5,5'-Disulfanediylbis(2-nitrobenzoic acid)), tetrathionate, selenocystine, hydroxymercuribenzoate (MBO), monobromobimane (mBBr), dibromobimane (dBBr), dibromomaleimide (dBM), N-subsituted dibromomaleimides (R-dBM, wherein R may be any functionalization of the dibromomaleimide), p-toluenesulfonyl chloride (TosCI), succinimidyl iodoacetate (SIA), N-succinimidyl S-acetylthioacetate (SATA), (succinimidyl 3-(2-pyridyldithio)propionate (SPDP), N-α-maleimidoacetoxysuccinimide ester (AMAS), or 1-Ethyl-3-[3-dimethylaminopropyl] carbodiimide hydrochloride (EDC). Additional modifying agents are provided in Hermanson, G. T. *Bioconjugate Techniques*. (Academic Press, 2013), herein incorporated by reference in its entirety.

(iv) Peptide Sequence

In an embodiment, the at least one binding site may be a peptide sequence with known affinity for another biological polymer. In some embodiments, the peptide sequence may comprise one portion of a split protein, one member of an oligomeric complex, a sequence with binding affinity for DNA, or a sequence with a binding affinity for a nanoparticle.

In an embodiment, the at least one binding site may be a metal-affinity peptide sequence. In an exemplary embodiment, the metal-affinity peptide sequence may be a histidine tag. In an additional exemplary embodiment, the histidine tag may be a C-terminal histidine tag or an N-terminal histidine tag. In some embodiments, the histidine tag may comprise from 2 histidine residues to about 10 histidine residues. In an exemplary embodiment, the histidine tag may comprise 6 histidine residues.

In an embodiment, the metal-affinity peptide sequence may bind a metal ion. Suitable metal ions include, without limit, Ni, Cu, Zu, Fe, and Co. In an exemplary embodiment, the metal ion may be Ni. In another exemplary embodiment, the metal ion may be Zn.

(v) Location of the Binding Site

In general, the position of the at least one binding site within the porous protein crystal pore can and will vary depending on the desired location of the at least one guest molecule within the porous protein crystal pore. A person skilled in the art would be able to select the appropriate location of the at least one binding site within the porous protein crystal pore to direct the at least one guest molecule to be at a specific location within the porous protein crystal pore.

(e) Protein Stability

In general, the porous protein crystal may be stabilized by forming covalent bonds, non-covalent bonds, or combinations thereof between amino acids present in adjacent monomers. A stabilized porous protein crystal will be more stable than an un-stabilized porous protein crystal if transferred to solution conditions that differ from the crystal growth mother liquour. For example, a stabilized protein crystal grown in high salt conditions, may persist when transferred to low salt conditions. Some benefits associated with increased stability include allowing for a high quality of diffraction, providing macroscopic crystal stability, and rendering the porous protein crystal competent for guest loading and release.

(i) Covalent Bonds

In an embodiment, covalent bonds may be formed by reacting amino acids present in adjacent monomers with a crosslinking agent. In a further embodiment, covalent bonds may be formed by reacting homogenous or heterogeneous amino acids present in adjacent monomers with a crosslinking agent. In an exemplary embodiment, covalent bonds may be formed between two sulfhydryl containing amino acids. In an exemplary embodiment, covalent bonds may be formed between two amine containing amino acids. In an exemplary embodiment, covalent bonds may be formed between an amine containing amino acid and a sulfhydryl containing amino acid. In an exemplary embodiment, covalent bonds may be formed between an amine containing amino acid and a carboxylate containing amino acid.

Suitable crosslinking agents may include, without limit, aldehydes, bis-NHS esters, bis-imidoesters, bis-maleimides, bis-haloalkyls, or carbodiimide reactive compounds; and combinations thereof.

Suitable aldehyde crosslinking agents may include, without limit, glutaraldehyde, formaldehyde, glyoxal, and combinations thereof.

Suitable NHS ester crosslinking agents will include 2 or more NHS ester groups, separated by linkers that may include 1-13 atoms, which may include, without limit, N,N'-Disuccinimidyl carbonate; N,N'-Disuccinimidyl oxalate; sulfodisuccinimidyl tartrate (Sulfo-DST); 3,3'-dithiobis[sulfosuccinimidylpropionate] (DTSSP); bis(sulfosuccinimidyl)suberate (BS3); ethylene glycol bis[sulfosuccinimidylsuccinate] (Sulfo-EGS); and combinations thereof.

Suitable bis-imidoesters crosslinking agents may include, without limit, dithiobispropionimidate (DTBP), dimethyl adipimidate (DMA), and combinations thereof.

Suitable bis-maleimide crosslinking agents may include, without limit, 1,4-bismaleimidobutane; 1,8-bismaleimidodiethyleneglycol; 1,11-bismaleimido-triethyleneglycol; bis-maleimidohexane; bismaleimidoethane; dithiobismaleimidoethane; and combinations thereof.

Suitable bis-haloalkyl crosslilnking agents may include, without limit, dibromobimane; dibromomaleimide; N-subsituted dibromomaleimides; dibromoxylene; phosgene; dichloroethane; and combinations thereof.

Suitable carbodiimide crosslinking agents may include, without limit, 1-Ethyl-3-[3-dimethylaminopropyl] carbodiimide hydrochloride (EDC); N',N'-dicyclohexyl carbodiimide (DCC); N,N'-diisopropylcarbodiimide (DIC); and combinations thereof.

In exemplary embodiments, the crosslinking agent may be 1-Ethyl-3-[3-dimethylaminopropyl] carbodiimide hydrochloride (EDC); formaldehyde; formaldehyde and urea; formaldehyde and guanidinium hydrochloride; glyoxal; glyoxal and dimethylamine borane (DMAB); glutaraldehyde; glutaraldehyde and dimethylamine borane complex; 1-Ethyl-3-[3-dimethylaminopropyl] carbodiimide hydrochloride (EDC); 1-Ethyl-3-[3-dimethylaminopropyl] carbodiimide hydrochloride (EDC) and imidazole; 1-Ethyl-3-[3-dimethylaminopropyl] carbodiimide hydrochloride (EDC) and sulfo N-hydroxysulfosuccinimide (sulfo-NHS); 1-Ethyl-3-[3-dimethylaminopropyl] carbodiimide hydrochloride (EDC), sodium malonate, and hydroxysulfosuccinimide (sulfo-NHS).

In an embodiment, the crosslinking agent may be contacted with the porous protein crystal from about 5 minutes to about 24 hours. In some embodiments, the crosslinking agents may be contacted with the porous protein crystal for about 5 minutes, about 10 minutes, about 20 minutes, about 30 minutes, about 40 minutes, about 50 minutes, about 60 minutes, 1.5 hours, about 2 hours, about 2.5 hours, about 3 hours, about 3.5 hours, about 4 hours, about 4.5 hours, or about 5 hours, about 5.5 hours, about 6 hours, about 6.5 hours, about 7 hours, about 7.5 hours, about 8.5 hours, about 9 hours, about 9.5 hours, about 10 hours, about 10.5 hours, about 11 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or about 24 hours.

In an embodiment, the crosslinking agent may be contacted with the porous protein crystal from about 5 minutes to about 24 hours. In some embodiments, the crosslinking agents are contacted with the porous protein crystal about 5 minutes, about 10 minutes, about 20 minutes, about 30 minutes, about 40 minutes, about 50 minutes, about 60 minutes, 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours.

In some embodiments, the crosslinking may be reversible. In other embodiments the crosslinking may be irreversible.

The amount of crosslinking agent may and will depend upon the concentration of the porous protein crystal and the identity of the protein. A person of ordinary skill in the art would be able to select the appropriate amount and concentration of the crosslinking agent to produce a crosslinked porous protein crystal.

(ii) Non-Covalent Bonds

In an embodiment, non-covalent bonds may be formed between amino acids present in adjacent monomers. In an embodiment, the non-covalent bonds include electrostatic and hydrophobic interactions.

In an exemplary embodiment, electrostatic interactions may be between charged amino acids. In a further embodiment, electrostatic interactions may be between positively and negatively charged amino acids. Charged amino acids include aspartic acid, glutamic acid, lysine, arginine, and histidine. A person skilled in the art would be able to estimate the charge of the aforementioned amino acids based on the pH of the solvent or buffer.

In an exemplary embodiment, hydrophobic interactions may be between at least two hydrophobic amino acids. Hydrophobic amino acids include alanine, isoleucine, leucine, phenylalanine, valine, proline, and glycine.

(II) Guest Molecule

Another aspect of the present disclosure encompasses at least one guest molecule that may bind to at least one binding side in the porous protein crystal pore.

(a) Identity

In general, the at least one guest molecule may comprise a nanoparticle or a macromolecule.

(i) Nanoparticle

In an embodiment, the at least one guest molecule may comprise a nanoparticle. Suitable nanoparticles may include transition metals, noble metals, or lanthanides. In some embodiments, the nanoparticle may comprise Au, Ag, Cu, Pt, Pd, Ru, Fe, Ni, C, Si, Cd, Se, or Zn. In preferred embodiments, the nanoparticle may comprise Au, Ag, or Fe. In an exemplary embodiment, the nanoparticle may comprise Au.

In an embodiment, the nanoparticle may have a diameter of about 3 nm to about 40 nm. In some embodiments, the nanoparticle may have a diameter of about 3 nm, about 4 nm, about 5 nm, about 6 nm, about 7 nm, about 8 nm, about 9 nm, about 10 nm, about 15 nm, about 20 nm, about 25 nm, about 30 nm, about 35 nm, or about 40 nm.

In another embodiment, the nanoparticle may comprise more than about 25 metal atoms. In some embodiments, the nanoparticle may comprise about 25, about 30, about 35, about 40, about 45, about 50, about 55, about 60, about 65, about 70, about 75, about 80, about 85, about 90, about 95, about 100, about 125, about 150, about 175, about 200, about 225, about 250, about 275, about 300, about 325, about 350, about 375, or about 400 metal atoms.

(ii) Macromolecule

In an embodiment, the at least one guest molecule may comprise a macromolecule. In some embodiments, the guest molecules may comprise synthetic or biological polymers. In some embodiments, the polymers may be ordered or disordered. In some embodiments, the polymers may be homogeneous or heterogeneous.

In some embodiments, the at least one guest molecule may comprise a biomacromolecule. Suitable biomacromolecules may include, without limit, an oligonucleotide (e.g., DNA or RNA) sequence, a polypeptide, a polysaccharide, or a polyphenol.

In an embodiment, the biomacromolecule may be an oligonucleotide. In some embodiments, the oligonucleotide may be from about 3 nucleotides to about 150 nucleotides in length. In other embodiments, the oligonucleotide may be single or double stranded. In some embodiments, the maximum spatial extent of the oligonucleotide may exceed 3 nm when in its respective folded conformation.

In another embodiment, the biomacromolecule may be a protein. In some embodiments, the protein may be from about 3 amino acids to about 1000 amino acids in length. In an embodiment, the biomacromolecule may be an enzyme. In some embodiments, the protein may be greater than 3 nm in diameter when in its respective folded conformation.

(b) Modifications—Binding Sites

In general, the at least one guest molecule may be modified to bind to the porous protein crystal to produce a porous protein crystal guest molecule conjugate through non-covalent capture or covalent capture.

(i) Non-Covalent Capture

In an embodiment, the at least one guest molecule may be modified to bind to the porous protein crystal to produce a porous protein crystal guest molecule conjugate through non-covalent capture.

In some embodiments, the at least one guest molecule may be modified with a shared metal affinity linker. In some embodiments, the shared metal affinity linker may comprise one or more carboxylic acid moieties, imidazole moieties, or thiol moieties, or any combination thereof.

Suitable shared metal affinity linkers may include, without limit, nitrilotriacetic acid (NTA), polyhistidine tags, dihistidine motifs, dithiol motifs, mixed histidine/cysteine motifs, and individual amino acids with significant metal affinity such as histidine or cysteine. In preferred embodiments, the shared metal affinity linker may comprise glutathione (GSH), nitrilotriacetic acid (NTA), a pair of proximal histidine sidechains, and a histidine tag. In an exemplary embodiment, the shared metal affinity linker may comprise glutathione (GSH) and nitrilotriacetic acid (NTA). In another exemplary embodiment, the shared metal affinity motif comprises a pair of proximal histidine sidechains. In still another exemplary embodiment, the shared metal affinity linker may be a histidine tag.

(ii) Covalent Capture

In an embodiment, the at least one guest molecule may be modified to bind to the porous protein crystal to produce a porous protein crystal guest molecule conjugate through covalent capture.

In some embodiments, the at least one guest molecule may, without modification, have an amino acid or a nucleic acid sequence motif suitable for covalent capture by the porous protein crystal. In some embodiments, the at least one guest molecule may form one or more covalent bonds to one or more residues within the porous protein crystal. In some embodiments, there may be a zero-length crosslink between the porous protein crystal and the at least one guest molecule, with no additional atoms derived from crosslinking agents. In an exemplary embodiment, a guest molecule thiol may be directly linked to a porous protein crystal thiol via a disulfide bond. In other embodiments, the at least one guest molecule may comprise one or more covalent bonds to one or more atoms derived from a crosslinking agent, and the atoms derived from the crosslinking agent may comprise one or more covalent bonds to the porous protein crystal.

Suitable crosslinking reagents may include, without limit, homo-bifunctional crosslinkers containing more than one sulfhydryl-specific functional group such as maleimide or pyridyldithiol moieties. Suitable maleimides may include, without limit, 1,8-bismaleimido-diethyleneglycol; 1,11-bis-maleimido-triethyleneglycol); 1,4-bismaleimidobutane); dithiobismaleimidoethane; bismaleimidohexane; bismaleimidoethane; and tris(2-maleimidoethyl)amine. Alternately, some embodiments may include heterobifunctional protein crosslinking reagents containing at least one sulfhydryl-specific functional group and at least one amine-specific functional group. Suitable amine-specific functional groups include, without limit, Succinimidyl 3-(2-Pryridyldithio)Propionate; Succinimidyl trans-4-(maleimidylmethyl)cyclohexane-1-Carboxylate; succinimidyl iodoacetate; succinimidyl 3-(bromoacetamido)propionate; succinimidyl (4-iodoacetyl)aminobenzoate; sulfosuccinimidyl (4-iodoacety)aminobenzoate; N-α-maleimidoacet-oxysuccinimide ester; N-β-maleimidopropyl-oxysuccinimide ester; N-γ-maleimidobutyryl-oxysuccinimide ester; N-γ-maleimidobutyryl-oxysulfosuccinimide ester; m-maleimidobenzoyl-N-hydroxysuccinimide ester; m-maleimidobenzoyl-N-hydroxysulfosuccinimide ester; succinimidyl 4-(N-maleimidomethyl)cyclohexane-1-carboxylate; sulfosuccinimidyl 4-(N-maleimidomethyl)cyclohexane-1-carboxylate; N-ε-malemidocaproyl-oxysuccinimide ester; N-ε-maleimidocaproyl-oxysulfosuccinimide ester; succinimidyl 4-(p-maleimidophenyl)butryrate; sulfosuccinimidyl 4-(N-maleimidophenyl)butyrate; Succinimidyl 6-((beta-maleimidopropionamido)hexanoate); succinimidyl 4-(N-maleimidomethyl)cyclohexane-1-carboxy-(6-amidocaproate); N-κ-maleimidoundecanoyl-oxysulfosuccinimide ester; succinimidyl 3-(2-pyridyldithio)propionate; succinimidyl 6-(3 (2-pyridyldithio)propionamido)hexanoatel sulfosuccinimidyl 6-(3'-(2-pyridyldithio)propionamido)hexanoate; and 4-succinimidyloxycarbonyl-alpha-methyl-α(2-pyridyldithio)toluene. In additional embodiments will include heterobifunctional protein crosslinking reagents capable of conjugating a carboxyl group on either the porous protein crystal or guest molecule to an amine group on the other molecule. Suitable crosslinking agents may include, without limit, dicyclohexylcarbodiimide; 1-ethyl-3-(3-dimethylaminopropyl)carbodiimide hydrochloride; 1-Ethyl-3-(3-Dimethylaminopropyl)carbodiimide, Hydrochloride; N-hydroxysuccinimide; N-hydroxysulfosuccinimide; N-hydroxysulfosuccinimide; N-hydroxysulfdosuccinimide; and N-hydroxysulfosuccinimide. In exemplary embodiments, the remaining atoms from the crosslinking adaptor will be fluorescent.

Adaptor groups may include, without limit, maleimide rings derived from dibromomaleimide and bimane rings derived from dibromobimane. In another exemplary embodiment, a guest molecule thiol may be bonded to a maleimide group which is also bonded to a porous protein crystal scaffold. In yet another exemplary embodiment, a guest molecule thiol may be bonded to a bimane group which is also bonded to a porous protein crystal scaffold.

In an embodiment, the at least one binding site may be a chemically modified amino acid. Suitable amino acids for chemical modification may include cysteine, lysine, glutamic acid, aspartic acid, or serine. In an embodiment, the amino acid may be modified by a modifying agent.

Suitable modifying agents for cysteine may include, without limit, Ellman's reagent (i.e., 5,5'-Disulfanediylbis(2-nitrobenzoic acid)), tetrathionate, hydroxymercuribenzoate (MBO), monobromobimane (mBBr), dibromobimane (dBBr), dibromomaleimide (dBM), or N-subsituted dibromomaleimides (R-dBM, wherein R may be any functionalization of the dibromomaleimide). Additional modifying agents are provided in Hermanson, G. T. *Bioconjugate Techniques*. (Academic Press, 2013), herein incorporated by reference in its entirety.

Suitable modifying agents for lysine may include, without limit, (succinimidyl iodoacetate) SIA, N-succinimidyl S-acetylthioacetate (SATA), (succinimidyl 3-(2-pyridyldithio)propionate (SPDP), or N-α-maleimidoacet-oxysuccinimide ester (AMAS). Additional modifying agents are provided in Hermanson, G. T. *Bioconjugate Techniques*. (Academic Press, 2013), herein incorporated by reference in its entirety.

Suitable modifying agents for glutamic acid or aspartic acid may include, without limit, 1-Ethyl-3-[3-dimethylaminopropyl] carbodiimide hydrochloride (EDC); N',N'-dicyclohexyl carbodiimide (DCC); N,N'-diisopropylcarbodiimide (DIC), or Carbonyldiimidazol (CDI). Additional modifying agents are provided in Hermanson, G. T. *Bioconjugate Techniques*. (Academic Press, 2013), herein incorporated by reference in its entirety.

Suitable modifying agents for serine may include, without limit, Carbonyldiimidazol (CDI) or p-toluenesulfonyl chloride (TosCI). Additional modifying agents are provided in Hermanson, G. T. *Bioconjugate Techniques*. (Academic Press, 2013), herein incorporated by reference in its entirety.

(c) Binding

In general, the at least one guest molecule binds to the porous protein crystal through a metal coordination site or covalent bond to produce a stable porous protein crystal guest molecule conjugate.

(i) Incubation

In an embodiment, the at least one guest molecule may be incubated with the porous protein crystal to produce a porous protein crystal guest molecule conjugate from about 1 minutes to about 48 hours. In some embodiments, the incubation period may be about 1 minute, about 5 minutes, about 10 minutes, about 20 minutes, about 30 minutes, about 40 minutes, about 50 minutes, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8.5 hours, about 9 hours, about 9.5 hours, about 10 hours, about 10.5 hours, about 11 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, about 24 hours, about 24.5 hours, about 25 hours, about 25.5 hours, about 26 hours, about 26.5 hours, about 27 hours, about 28.5 hours, about 29 hours, about 29.5 hours, about 30 hours, about 30.5 hours, about 31 hours, about 31.5 hours, about 32 hours, about 32.5 hours, about 33 hours, about 33.5 hours, about 34 hours, about 34.5 hours, about 35 hours, about 35.5 hours, about 36 hours, about 36.5 hours, about 37 hours, about 37.5 hours, about 38 hours, about 38.5 hours, about 39 hours, about 39.5 hours, about 40 hours, about 40.5 hours, about 41 hours, about 41.5 hour, about 42 hours, about 42.5 hours, about 43 hours, about 43.5 hours, about 44 hours, about 44.5 hours, about 45 hours, about 45.5 hours, about 46 hours, about 46.5 hours, about 47 hours, about 47.5 hours, or about 48 hours.

In an embodiment, the amount of the at least one guest molecule incubated with the protein scaffold to produce a porous protein crystal guest molecule conjugate may and will depend on the identity of the porous protein crystal and the at least one guest molecule.

(ii) Metal Coordination Site

In an embodiment, the at least one guest molecule binds to the porous protein crystal through a metal coordination site. Suitable metals for the metal coordination site include, without limit, Ni, Cu, Zu, Fe, Co, Ca, Mg, Mn, Ru, Rh, Cd, Ag, Hg, Au, Pt, and Ir. In a preferred embodiment, the metal in the metal coordination site may include Ni, Cu, Zu, Fe, Cd, Ca, Mg, Mn, and Co. In exemplary embodiment, the metal in the metal coordination site may be Ni. In another exemplary embodiment, the metal in the metal coordination site may be Zn.

In an embodiment, the porous protein crystal guest molecule conjugate is incubated with at least one metal ion from about 10 minutes to about 10 days to produce a stable porous protein crystal guest molecule conjugate. In some embodiments, the incubation period may be about 10 minutes, about 20 minutes, about 30 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hour, about 20 hours, about 21 hours, about 22 hours, about 23 hours, about 1 day, about 1.5 days, about 2 days, about 2.5 days, about 3 days, about 3.5 days, about 4 days, about 4.5 days, about 5 days, about 5.5 days, about 6 days, about 6.5 days, about 7 days, about 7.5 days, about 8 days, about 8.5 days, about 9 days, about 9.5 days, or about 10 days. In an exemplary embodiment, the incubation period may be about 1 day. In a further embodiment, the incubation period may be about 1 hour.

(iii) Covalent Bond

In an embodiment, the at least one guest molecule binds to the porous protein crystal through one or more covalent bonds.

(III) Methods

An additional aspect of the present disclosure encompasses a method for preparing a porous protein crystal guest molecule conjugate. The method may comprise: (a) crystallizing a protein in appropriate crystal growth conditions to produce a porous protein crystal; (b) reacting the porous protein crystal with a crosslinking agent to produce a crosslinked porous protein crystal, wherein the crosslinking agent crosslinks adjacent monomers of the porous protein crystal; and (c) incubating the crosslinked porous protein crystal with at least one guest molecule to produce a porous protein crystal guest molecule conjugate.

In some embodiments, the method may comprise pre-treating the soluble protein with chemical agents to enhance crystallization or to protect functional groups including without limit cysteine sidechains. In some embodiments, the method may comprise a washing step where crystals are exposed to a new solution or transferred into a new solution. In some embodiments, the method may comprise a separate quenching step to stop or enhance the crosslinking reaction. In some embodiments, the method may comprise a post-crosslinking crystal washing step. In some embodiments, the method may comprise incubating the host-guest protein crystal with an additional solution to form alternative or additional bonds between the guest molecule and the host crystal.

In other aspects, the present disclosure provides a method for preparing a porous protein crystal guest molecule conjugate. The method may comprise: obtaining a porous protein crystal, wherein the porous protein crystal has been reacted with a crosslinking agent to produce a crosslinked porous protein crystal and the crosslinking agent crosslinks adjacent monomers of the porous protein crystal; and incubating the crosslinked porous protein crystal with at least one guest molecule to produce a porous protein crystal guest molecule conjugate.

In a further aspect, the methods disclosed herein, may further comprise reversing the binding of the guest molecule to the porous protein crystal. In some embodiments, guest molecules bound to the porous protein crystal may be released using acidic or basic solutions. In some embodiments, guest molecules bound to the porous protein crystal may be released using reducing conditions.

Suitable reducing conditions may be incurred by reducing agents may include, without limit, beta mercaptoethanol (BME), tris(2-carboxyethyl)phosphine (TCEP), dithiothreitol (DTT), dimethylamine borane (DMAB), sodium borohydride (Na $BH_4$), sodium cyanoborohydride (Na $BH_3CN$), or iodide. In some embodiments, the guest molecule bound to the crystal may be released via the addition of nucleophiles. In an exemplary embodiment, the nucleophile comprises hydroxylamine.

In some embodiments, the crosslinking chemistry may compromise the function of the amino acids incorporated within the porous protein crystal, requiring the use of protecting groups to preserve function. Therefore, in some embodiments, the soluble protein that comprises the porous protein crystal may be pre-treated with chemical reagents to provide protecting groups. In other embodiments, the protecting groups may be installed after crystallization. In exemplary embodiments, scaffold protein cysteines may be protected via disulfide exchange, reaction with thiosulfonates, or other reversible conjugation chemistries. In preferred embodiments, scaffold protein crystals are protected with Ellman's reagent (5,5'-Dithiobis(2-nitrobenzoic acid)), tetrathionate, or methanethiosulfonates. In an exemplary embodiment, scaffold protein crystals are protected with Ellman's reagent (5,5'-Dithiobis(2-nitrobenzoic acid)). In another exemplary embodiment, scaffold protein crystals are protected with tetrathionate. In yet another exemplary embodiment, scaffold protein crystals are protected with methanethiosulfonates.

In some embodiments, the crosslinking solutions will be optimized for rapid function, and the preservation of protein crystal diffraction over time. Different protein crystals have significantly varying composition of their growth solution ("mother liquour"). Therefore, it may be necessary to select a protein crosslinking solution with the best performance in that mother liquor. Table 5 provides a set of different crosslinking solution recipes. In some embodiments, these will be further tuned by adjusting pH, solute concentrations, temperature, and incubation times. In some embodiments, the crosslinking protocol may be further optimized by incubation at more than one temperature or pH. In some embodiments, the crosslinking protocol will benefit from separate wash steps. In some embodiments, the crosslinking protocol will benefit from distinct quenching stages. In some embodiments, quenching stages will rely on the use of reducing agents. In an exemplary embodiment, a quenching stage may rely on the use of dimethylamineborane (DMAB). In another exemplary embodiment, a quenching stage may rely on the use of dilute acidic conditions. In yet another exemplary embodiment, a quenching stage may rely on the use of hydroxylamine.

(i) Crystallization

In general, the method may comprise crystallizing a protein to produce a porous protein crystal. In some embodiments, the protein may be crystallized by known methods in the art as described in Section (I)(b).

In some embodiments the crystallization protocol may make use of crystal seeds to enhance crystal growth. In some additional embodiments, the crystallization protocol may make use of crystal seeds that are stabilized by crosslinking protocols as described in Section (I)(e).

(ii) Crosslinking a Porous Protein Crystal

In general, the method may comprise reacting the porous protein crystal with a crosslinking agent to produce a crosslinked porous protein crystal. In a further embodiment, the crosslinking agent crosslinks adjacent monomers of the porous protein crystal. In some embodiments, the crosslinking agent may be as described in Section (I)(e).

(iii) Forming a Porous Protein Crystal Guest Molecule Conjugate

In general, the method comprises incubating the crosslinked porous protein crystal with at least one guest molecule to produce a porous protein crystal guest molecule conjugate. In some embodiments, the at least one guest molecule may be a described in Section (II)(a). In some embodiments, the at least one guest molecule may be modified as described in Section (II)(b). In other embodiments, the at least one guest molecule may not be modified. In some embodiments, the at least one guest molecule may bind to the at least one binding site in the porous protein crystal pore as described in Section (II)(c).

(iv) Forming a Stable Porous Protein Crystal Guest Molecule Conjugate

In an additional embodiment, the porous protein crystal guest molecule conjugate may be incubated with at least one metal ion to produce a stable porous protein crystal guest molecule conjugate. In some embodiments, the at least one metal ion may be as described in Section (II)(c).

(IV) Applications

The compositions and methods described herein may be used as a platform for elucidating the atomic structure of guest molecules using X-ray diffraction (XRD) techniques. The addition of a guest molecule (e.g., nanoparticle) may increase the electron density in specific areas of the electron density map derived from the XRD experiments.

In some aspects, the method for determining the structure of the guest molecule may comprise obtaining a porous protein crystal guest molecule conjugate, wherein the porous protein crystal guest molecule conjugate comprises a guest molecule and a porous protein crystal, wherein the porous protein crystal has been reacted with a crosslinking agent to produce a crosslinked porous protein crystal and the crosslinking agent crosslinks adjacent monomers of the porous protein crystal; and imaging the porous protein crystal guest molecule conjugate to determine the molecular structure of the at least one guest molecule. As discussed above, in some aspects, XRD may be used to image the porous protein crystal guest molecule conjugate.

The compositions and methods described herein may also be used in diagnostics. For example, the transport of guest molecules (crystal uptake and release) may be coupled to the presence of analyte molecules. In some embodiments, fluorescent guest molecules are selectively released from porous protein crystal hosts depending on the solution conditions. In some embodiments, fluorescent guest molecules are selectively released when the crystal is exposed to an altered pH, temperature, or redox state. In an exemplary embodiment, covalently bound guest molecules are released when the crystal is exposed to a reducing environment. Without limitation, such a reducing environment may be caused by environmental cues or reducing reagents such as the ones described in Section III. In another exemplary embodiment, guest molecules bound via shared metal affinity are released when the crystal is exposed to a lower pH or in the presence of metal chelators (e.g., EDTA). In some embodiments, the host-guest crystal may comprise multiple different fluorescent guest molecules, where solution conditions effect a change in the transport or release of a subset of the guest molecules. In an exemplary embodiment, a change in solution conditions will effect a change in the net fluorescence signal of a crystal by releasing one or more fluorescent guest molecules and therefore changing the ratio of fluorescent guest molecules.

The compositions and methods described herein may also be used for biohybrid materials. Guest molecules localized to specific sites within the crystal can have myriad functions, including the ability to nucleate the growth of further structures. In one embodiment, guest nanoparticles may be used to nucleate the growth of subsequent inorganic nanostructures. In another embodiment, guest molecules may be used to nucleate or otherwise support the subsequent growth of polymers. In an exemplary embodiment, guest molecules may be used to nucleate or otherwise support the growth of conductive polymers including, without limitation, polypyrrole, polythiophene, polyaniline, and poly(3,4-ethylenedioxythiophene) polystyrene sulfonate.

The compositions and methods described herein may also be used for therapeutic materials. In this case, the guest molecules protected within the crystals may have therapeutic functions. Therapeutic functional guest molecules may include, without limit, growth factors, enzymes, inhibitors, and transport proteins. In some embodiments, the host protein crystals may have sub-micron diameter to enable the delivery of therapeutic guest molecules. In some embodiments, the host protein crystals may penetrate cells to provide guest molecules as therapeutic cargo. In some embodiments, host protein crystals may constitute a large immobile depot suitable for providing the controlled release of therapeutic molecules. Suitable guest molecules for controlled release may include, without limit, subunit vaccines and growth factors. In some embodiments, the host-guest crystals may provide for the selective release of the guest molecules when encountering specific pH values (e.g., acidic tumor microenvironments or in specific regions of the gastrointestinal tract) or when encountering a reducing environment (e.g., if a guest-laden porous protein crystal reaches the reducing environment inside of a host cell cytosol.

In further aspects, the present disclosure also provides a kit for binding at least one guest molecule to a porous crystal protein. A kit may comprise, for example, a porous protein crystal that has been stabilized. The porous protein crystal may have a plurality of crystal pores with an average diameter of from about 3 nm to about 50 nm. The kit may further comprise a guest molecule. In other embodiments, the kit may further comprise materials and/or reagents for modifying a guest molecule so that it binds to the porous protein crystal. The kit may further comprise additional materials and/or reagents for incubating a guest molecule with the porous crystal protein. The kit may further comprise additional materials and/or reagents for reversing the binding of the guest molecule to the porous protein crystal.

DEFINITIONS

When introducing elements of the present disclosure or the preferred aspects(s) thereof, the articles "a," "an," "the" and "said" are intended to mean that there are one or more of the elements. The terms "comprising," "including" and "having" are intended to be inclusive and mean that there may be additional elements other than the listed elements.

The term "conjugate," as used herein refers to guest molecules that are entrapped, non-covalently bound, or covalently bound to a porous protein crystal.

The term "nanoparticle," as used herein refers to a nanostructure that is typically between about 5 nm and 400 nm across the largest dimension of the structure, but in some instances, may be bigger or smaller. A nanoparticle of the invention may be spherical, tubular, cylindrical, cubic, hexagonal, dumbbell, or any other shape that may be envisaged or built in a laboratory setting. In one embodiment, the largest dimension of a nanoparticle may be between about 100 nm and about 300 nm. In another embodiment, the largest dimension of a nanoparticle may be between about 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 nm.

As various changes could be made in the above-described compositions, methods, and kits without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The following abbreviations are used herein: CJ=*Campylobacter jejuni*; CLM=confocal laser scanning microscopy; GA=glutaraldehyde; GSH=glutathione; histag=histidine tag; MOF=metal organic frameworks; rmsd=root mean squared deviation; TEV=tobacco etch virus; and XRD=X-ray diffraction.

Example 1. Gold Nanoparticle Capture with Protein Crystal Scaffolds

Introduction

DNA assemblies have been used to organize inorganic nanoparticles into 3D arrays, with emergent properties arising as a result of nanoparticle spacing and geometry. Described herein is the use of engineered protein crystals as an approach to biologically mediated assembly of inorganic nanoparticles. The protein crystal's 13 nm diameter pores result in an 80% solvent content and display hexahistidine sequences on their interior. The hexahistidine sequence captures $Au_{25}$(glutathione)$_{~17}$ (nitrilotriacetic acid)$_{~1}$ nanoclusters throughout a chemically crosslinked crystal via the coordination of Ni(II) to both the cluster and the protein. Nanoparticle loading was validated by confocal microscopy and elemental analysis. The nanoparticles may be released from the crystal by exposure to EDTA, which chelates the Ni(II) and breaks the specific protein/nanoparticle interaction. The integrity of the protein crystals after crosslinking and nanoparticle capture was confirmed by single crystal x-ray crystallography.

The optical and magnetic properties of inorganic nanoparticles, which are already quite different than their corresponding bulk-phase counterparts, are further modified in ordered assemblies. These changes depend on the distance between particles, and in the case of anisotropic particles, the orientation of particles relative to each other. The application of nanoparticle assemblies is realized in biomedicine, for instance in diagnostics.

The use of biological scaffolds to enforce particle assembly has been used for DNA oligonucleotides. Both DNA origami and cDNA based approaches have been used to control the assembly of gold nanoclusters. Also, both viruses and multimeric proteins have been used for protein organization of nanoparticles. Binary superlattices by co-assembling protein cages with nanoparticles have also been prepared. In contrast, the use of proteins to organize nanoparticles is not well established, because protein oligomer assembly structures are harder to predict than DNA nanostructure.

In this disclosure metallic nanoparticles are organized in three dimensions within pre-existing crosslinked crystals. Compared to other scaffold materials, crosslinked protein crystals offer advantages in terms of stability and precision in the face of changing solvent conditions. However, uptake of the guest particles into the crystal, depends on the size of the particles with respect to the solvent channels of the crystal. These pores are sometimes used to facilitate diffusion of cofactors, drugs, and substrates into crystals, in order to observe the biological effects of these molecules in single crystal x-ray structural studies. Diffusion of metals into crystals is also used in metal based phasing methods such as multiple anomalous dispersion and multiple isomorphous replacement. Indeed, small metal clusters were used for phasing the largest biomacromolecules solved by single-crystal x-ray methods.

This disclosure is the first example of successful, controlled adsorption of larger nanoparticles into a pre-existing protein crystal. Moreover the conventional 'soaking' of metal coordination complexes and clusters into crystals for phasing relies on serendipitous binding; the metals do not adsorb to pre-determined sites. In contrast, presented herein is the first example of nanoparticles captured inside a pre-existing protein crystal via a specific metal-mediated interaction. One benefit of metal-based capture motifs is the relative ease of generalizing the capture motif to other guest molecules.

Figure 1A:
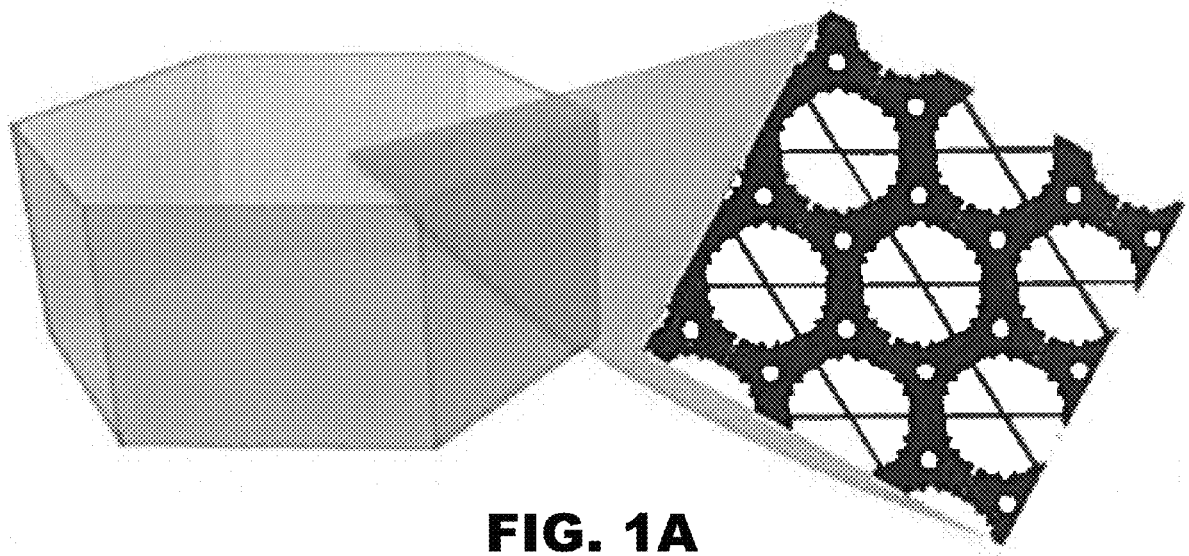
FIG. 1A, FIG. 1B, FIG. 1C, and FIG. 1D depict images of a putative periplasmic polyisoprenoid-binding protein from *Campylobacter jejuni* (CJ).
Figure 1B:
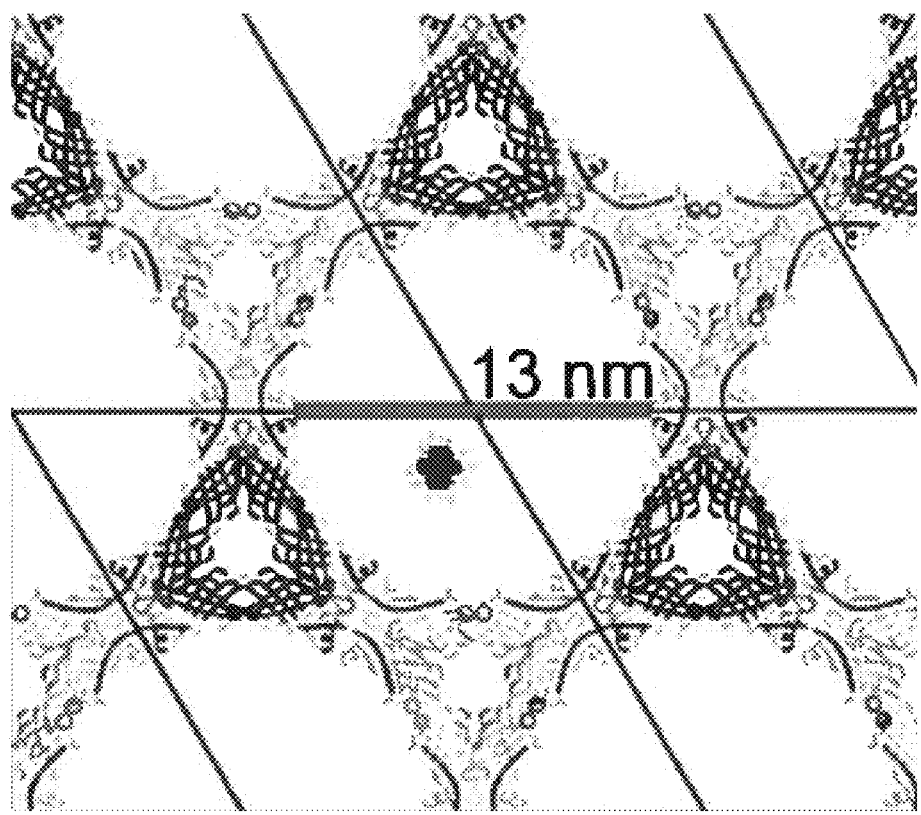
Figure 1C:
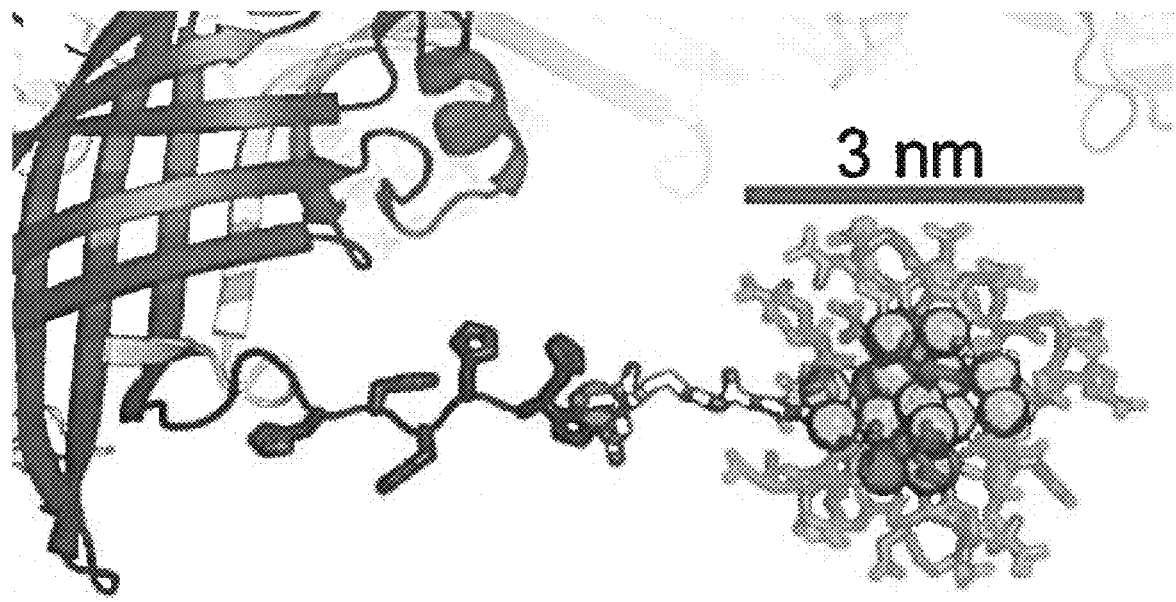
Figure 1D:
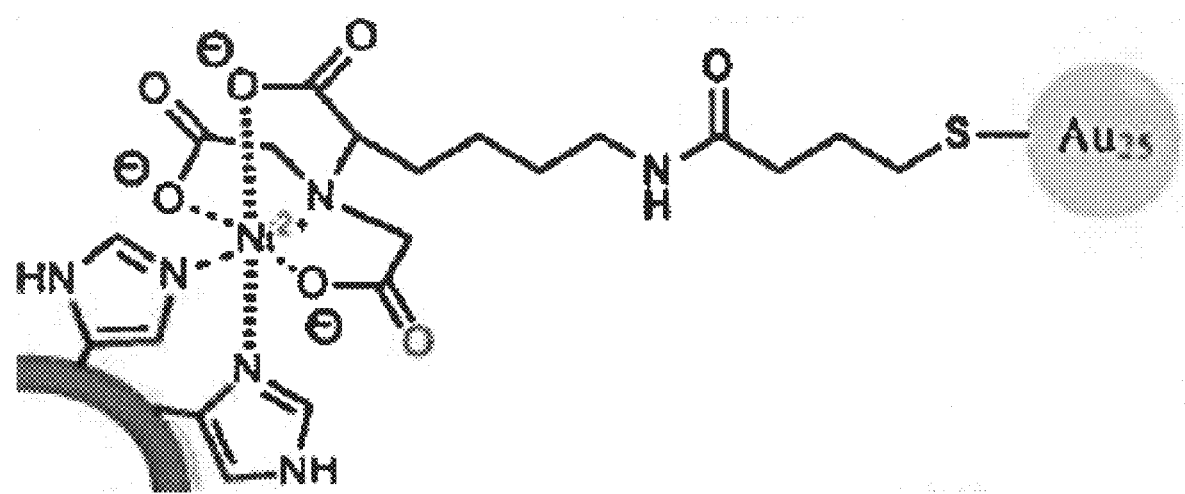

To accomplish the uptake of nanoparticles (specifically $Au_{25}$(GSH)$_{17}$(NTA) clusters), a host crystal with large pores were employed (FIG. 1A). Control experiments (below) suggested that the guest particles are tethered to the host crystal via surface NTA groups that bind Ni(II) atoms that are also coordinated by hexahistidine metal affinity tag (histag) presented at specific locations within the host crystal (FIG. 1B). The interaction is specific and reversible. With the availability of increasingly powerful algorithms for protein design, porous protein crystal scaffolding may approach, or even surpass, the ability of DNA to spatially localize inorganic nanoparticles.

Figure 5:
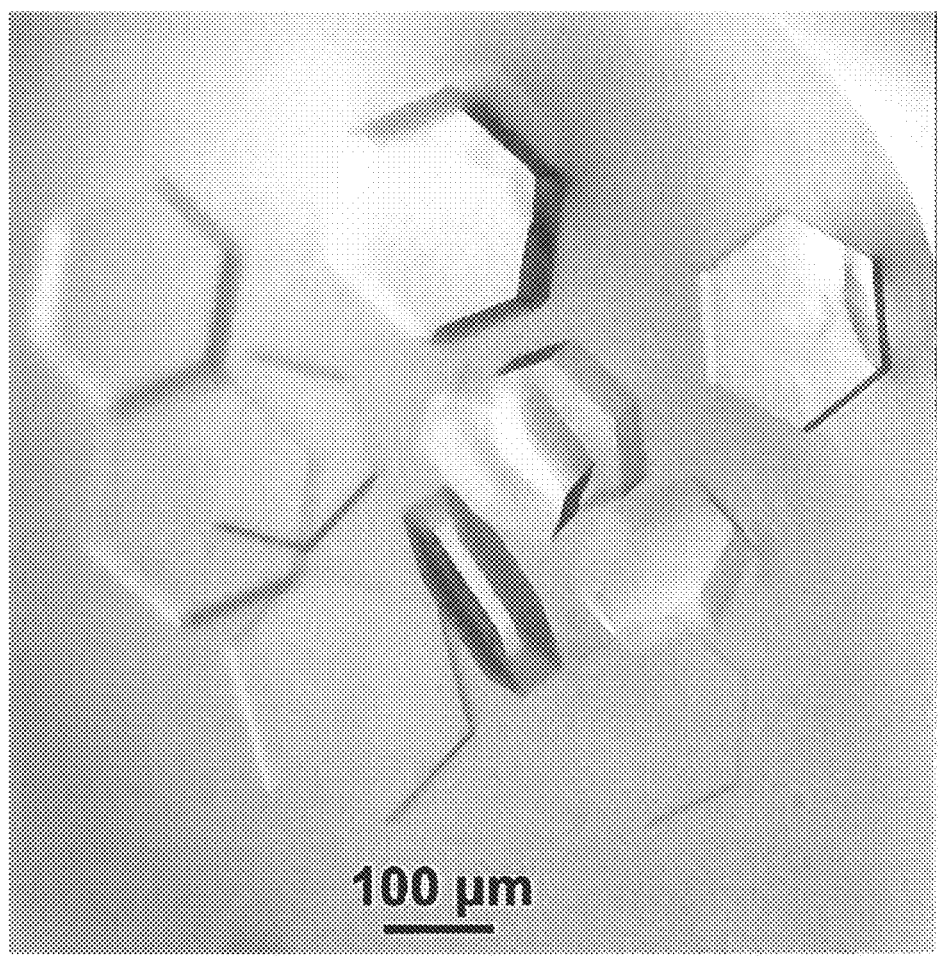
FIG. 5 depicts a representative growth well of CJ crystals in MTACSIMATE.

The host protein crystal was selected in a systematic, automated screen of the Protein Data Bank for protein crystals with large solvent channels (FIG. 1A). The crystal selected from the database is composed of a single protein, CJ0 (Genebank ID: cj0420, Protein Data Bank (PDB) code: 2FGS). CJ0 is a putative periplasmic polyisoprenoid-binding protein from *Campylobacter jejuni*. The vector encoding CJ0 (SEQ ID NO. 1) was obtained from the Protein Structure Initiative: Biology-Materials Repository. For ease of uniform expression and purification, the periplasmic signaling peptide was deleted, yielding the target gene, CJ. CJ has a C-terminal histag and was encoded in expression vector pSB3 (DNASU Plasmid I Detailed Vector Information: pSB3. DNASU Plasmids at <http://dnasu.org/DNASU/GetVectorDetail.do?vectorid=383>, which is herein incorporated by reference). CJ crystals were grown in MTACSI-MATE buffer (FIG. 5) at pH 7.5 and crosslinked by direct addition of 1% glyoxal and 25 mM dimethyl amine borane complex (DMAB). The crosslinking reaction was quenched after two hours via addition of 0.3 M hydroxylamine and 25 mM DMAB at pH 5.0.

Figure 2:
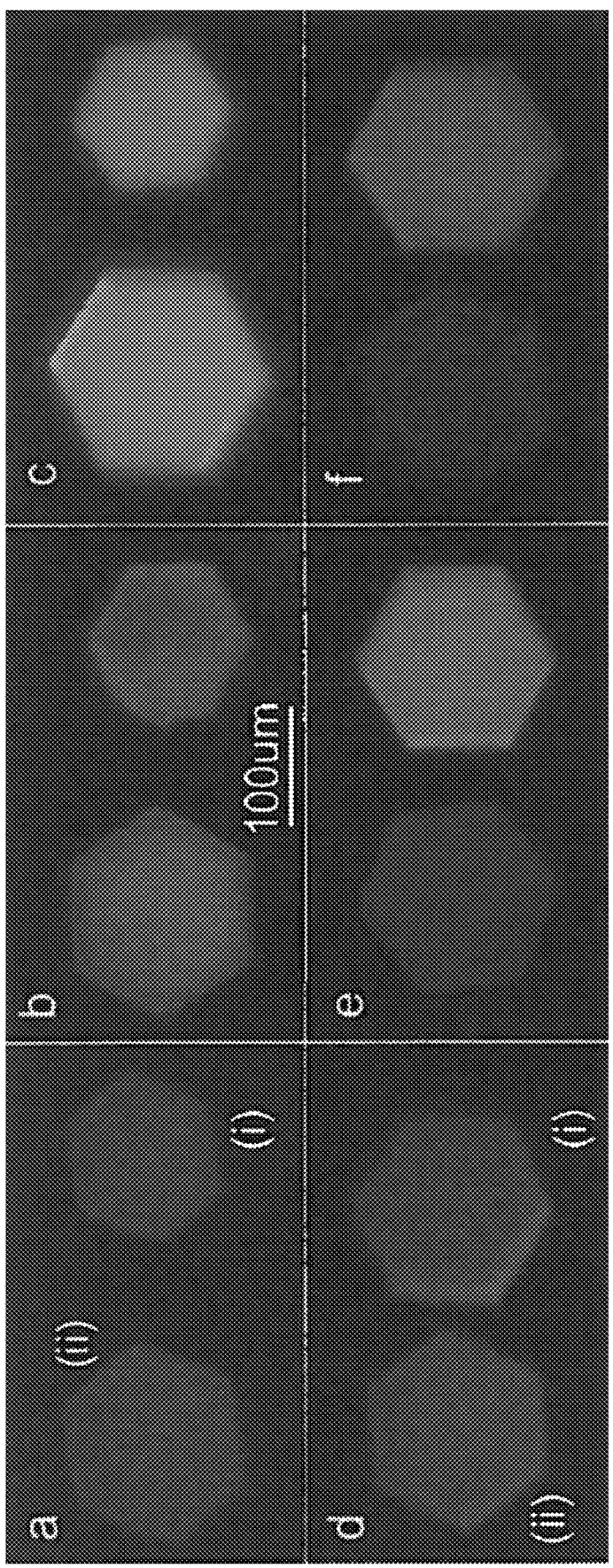
FIG. 2 depicts images of the CJ (ii) and CJΔH6 crystals (i). (Panel A) At t=30 minutes in 1 mg/mL $Au_{25}$(GSH)$_{17}$NTA. (Panel B and Panel E) at t=4 days in 1 mM $NiSO_4$ at pH 7. (Panel C and Panel F) At t=1 hour in 0.1 M EDTA at pH 7. (Panel D) At t=30 minutes in 1 mg/mL $Au_{25}$(GSH)$_{18}$. Imaged with 405 nm laser and 450 nm longpass filter.
Figure 3A:
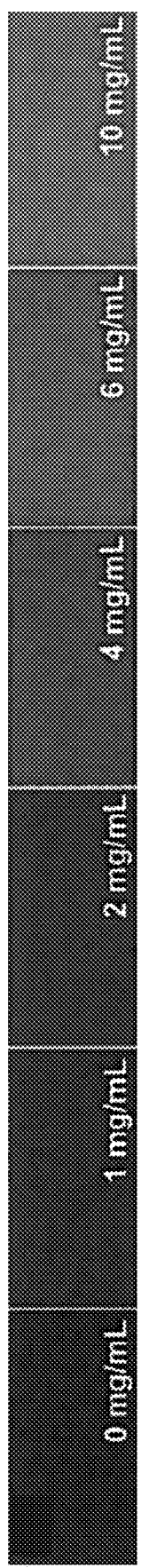
FIG. 3A depicts confocal laser microscopy (CLM) images of $Au_{25}$(GSH)$_{17}$(NTA) fluorescence standards: 0, 1, 2, 4, 6, and 10 mg/mL (left to right).
Figure 3B:
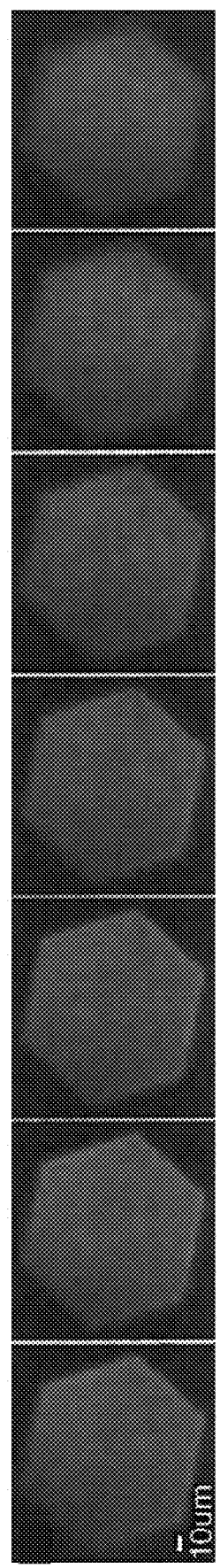
FIG. 3B depicts CLM z-stack showing $Au_{25}$(GSH)$_{17}$(NTA) full loaded into a CJ protein crystal. The crystal was soaked in 1 mg/mL $Au_{25}$(GSH)$_{17}$(NTA) for 30 minutes, then incubated in 1 mM $NiSO_4$ for five days prior to imaging. The 30 μm z-stack was taken through the crystal from the top surface (left) to the bottom surface (right) at 5 μm intervals.
Figure 3C:
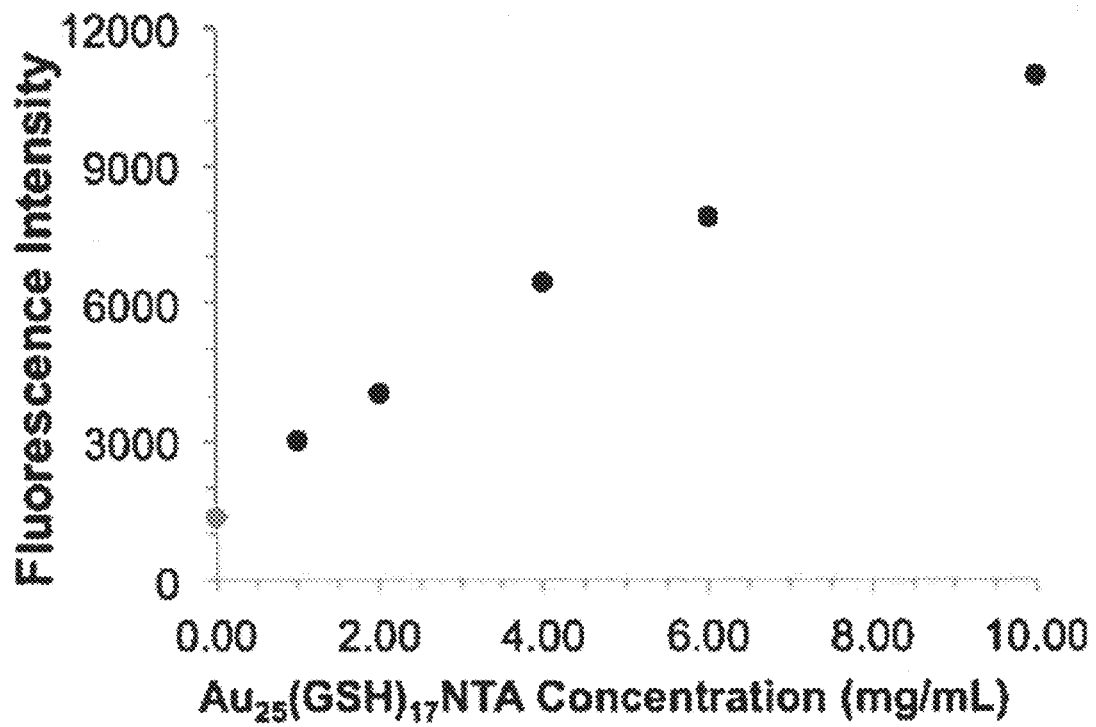
(FIG. 3C) Fluorescence intensity standard curve created by averaging $Au_{25}$(GSH)$_{17}$(NTA) intensities from (FIG. 3A).
Figure 3D:
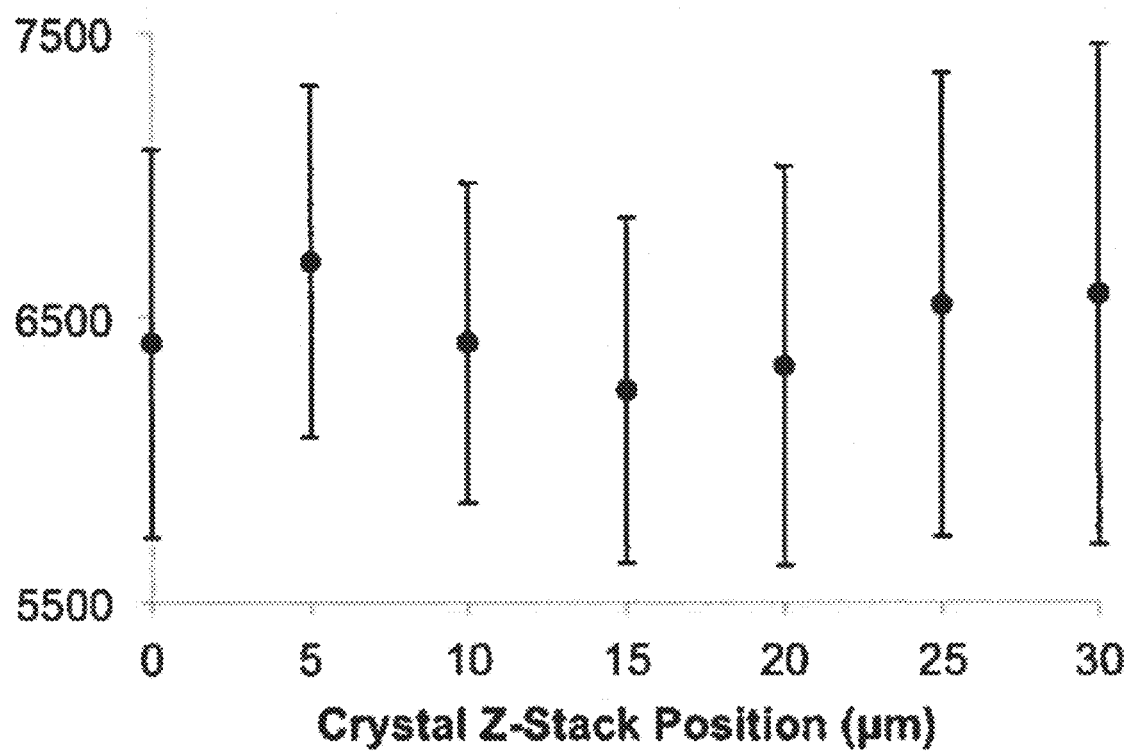
(FIG. 3D) Average fluorescence intensity of crystal cross-sections from (FIG. 3B). When compared to the fluorescence intensity standard curve in (FIG. 3C), the crystal is shown to retain an average $Au_{25}$(GSH)$_{17}$(NTA) concentration of 4.7±0.7 mg/mL. All images were taken under identical optical settings and excited with a 561 nm diode laser, chosen for lower background fluorescence.

Crosslinked CJ crystals readily absorbed $Au_{25}$(GSH)$_{17}$(NTA) and $Au_{25}$(GSH)$_{18}$, as judged by intrinsic nanoparticle fluorescence (FIG. 2 and FIG. 3B). FIG. 2 shows typical crystals at the end of a 30 minute incubation in each gold nanoparticle solution. The time it takes for the solution to completely penetrate the crystal varies with solution concentration and crystal thickness. However, the nanoparticles generally "load" the crystals within about 30 minutes, as judged by confocal cross-section (FIG. 3A). FIG. 2 demonstrates that the nanoparticle NTA, the scaffold histag, and Ni(II) all appear necessary to retain the nanoparticle within the crystal pore. For example, crystals lacking a histag (CJAH6) lost $Au_{25}$(GSH)$_{17}$(NTA) within 4 days (FIG. 2, panels a-c), even in the presence of Ni(II). In the absence of Ni(II), release of $Au_{25}$(GSH)$_{17}$(NTA) from CJ crystals does not require EDTA (FIG. 7).

Confocal laser microscopy (CLM) and elemental analysis were used to quantify loading of the crystals. A CJ crystal was incubated for 30 minutes with $Au_{25}(GSH)_{17}(NTA)$, then transferred to a 50 µl reservoir containing 1 mM Ni(II) and incubated for a further five days. CLM shows retention of gold nanoparticles throughout the entire thickness of the crystal (FIG. 3B). A CLM fluorescence intensity standard curve was created and used to interpolate an estimated concentration of $Au_{25}(GSH)_{17}(NTA)$ within the crystal. The fluorescence intensity of gold nanoparticle solutions ranging from 0 mg/mL to 10 mg/mL was measured. Comparing these values to the fluorescence intensity inside the crystal z-stack, it was found that after 30 minutes of loading and a five day incubation in $NiSO_4$, gold nanoparticles adsorbed to an average of 4.7±0.7 mg/mL within the crystal pores. This concentration is roughly equivalent to one $Au_{25}(GSH)_{17}$ (NTA) cluster per two unit cells. Elemental analysis confirmed the adsorption of gold nanoparticles per unit cell of the crystal at various timepoints during loading and unloading (FIG. 12). At the most concentrated timepoints (t=48 hours), elemental analysis suggested an average of 12 nanoparticles per unit cell in the crystal, a 118.5 mg/mL concentration in crystallo.

Figure 9A:
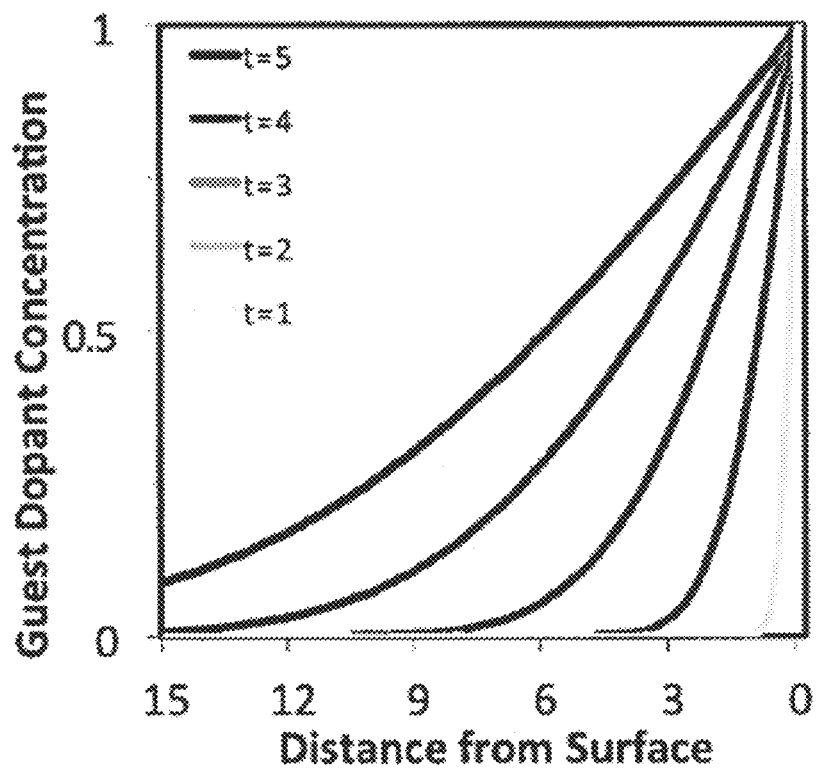
FIG. 9A and FIG. 9B depict graphs showing the concentration gradient just inside the host material.
Figure 9B:
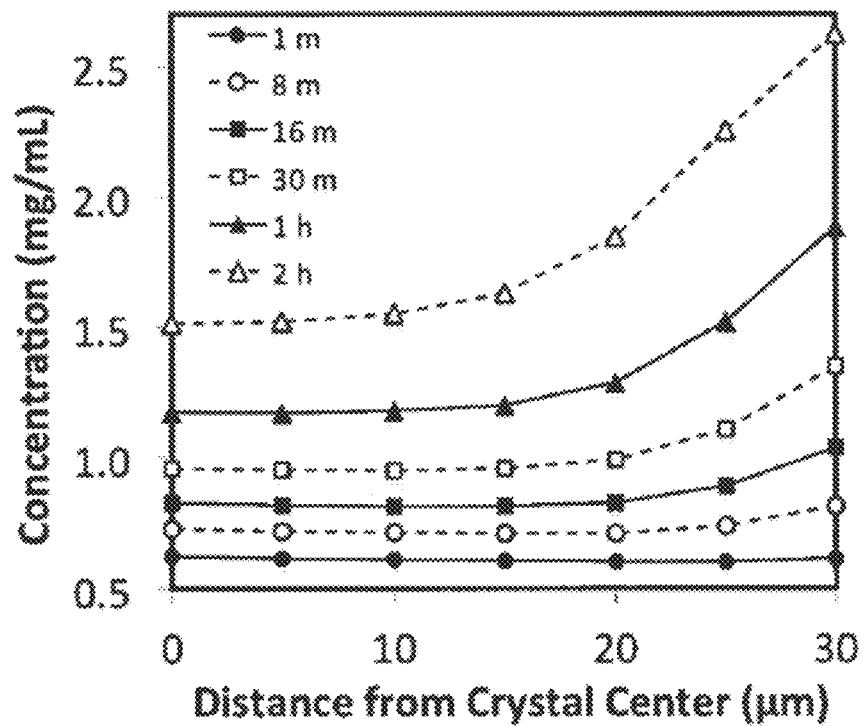

Time lapse confocal loading data suggests that strong adsorption is complicating guest diffusion (FIG. 9A and FIG. 9B). Simple concentration-independent diffusion models with a fixed surface concentration boundary condition predict a guest concentration gradient that decreases with time as the concentration in the crystal center catches up with the layers that are closer to the external solution. In stark contrast, it was observed that the guest nanoparticle concentration gradient increases over the first hour of loading.

Crystal quality after crosslinking and $Au_{25}(GSH)_{17}(NTA)$ loading and unloading was assessed by single crystal x-ray diffraction (FIG. 10A and FIG. 10B). Crystal diffraction was retained to 4.2 Å resolution with 1.2° mosaicity. Retention of crystal integrity after full loading of gold nanoparticles indicated that the C1 protein crystal nanopores remained intact and provided a robust scaffold for reversible, site-specific gold nanoparticle capture. However, $Au_{25}(GSH)_{17}$ (NTA) was not visible in the XRD electron density map (FIG. 11). This result is consistent with the nanoparticles adopting heterogeneous positions within the crystal.

In sum, gold nanoparticles were immobilized using precisely spaced motifs within a robust array of 13 nm nanopores delimited by a highly porous (80% solvent) protein crystal (FIG. 11). Scaffold formation was robust, and crystals could be grown and crosslinked with and without histags. Confocal microscopy indicated long-term (>5 days), Ni(II) dependent capture throughout the entire thickness of the crystal. Elemental analysis confirmed increasing adsorption of gold nanoparticles within the protein crystal pores over time, as well as removal upon addition of EDTA. Both elemental analysis and fluorescence intensity from confocal microscopy show that gold nanoparticles are absorbed into the crystal beyond concentrations expected through pure diffusion. The attachment is specific and reversible, the same crystal scaffold can be repeatedly loaded and unloaded with $Au_{25}(GSH)_{17}(NTA)$, (FIG. 8) and the crystal retains x-ray diffraction quality throughout loading and unloading of nanoparticles.

Methods

Reagents:

The following chemicals were purchased from Sigma-Aldrich and used without further purification: Gold (III) chloride trihydrate ($HAuCl_4$, ≥49.0% Au basis), L-glutathione reduced (GSH, 98.0%). The following chemicals were purchased from TCI America and used without further purification: $N^\epsilon$-carbobenzoxy-L-lysine ($N^\epsilon$-Cbz-L-lysine, >98.0%). Other reagents were purchased from Alfa Aesar, Thermo Scientific, and Sigma-Aldrich and used without further purification. Lithium sulfate ($Li_2SO_4$, 98.5%). Trimethylamine N-oxide (TMAO, 98%). Hydroxylamine solution (50 wt. % in $H_2O$). A blend of 1.83 M malonic acid, 0.25 M sodium citrate, 0.12 M succinic acid, 0.3 M D-L malic acid, 0.4 M acetic acid, 0.5 M sodium formate, and 0.16 M sodium tartrate was titrated to pH 7.5 using sodium hydroxide, and was used in crystallization and crosslinking. This is a modified blend of TACSIMATE from Hampton Research and is referred to as MTACSIMATE. The modification removes ammonium from the solution, which contains primary amines that interfere with protein crystal crosslinking.

Protein Crystal Preparation:

Periplasmic protein (Genebank ID: cj0420, Protein Data Bank code: 2FGS) from *Campylobacter jejuni* was selected from a scan of the Protein Data Bank for proteins that crystallize with large pores (SEQ ID NO. 2). It was expressed in pSB3 in *E. coli* BL21 (DE3) pLySs using a glucose/lactose induction system at 17° C. for 36 hours (Studier, F. W. Protein production by auto-induction in high density shaking cultures. Protein Expr. Purif. 41, 207-234 (2005), herein incorporated by reference in its entirety). The cells were lysed by sonication and purified via immobilized metal affinity chromatography. Purified protein was buffer exchanged into 150 mM NaCl, 10 mM HEPES, and 10% glycerol at pH 7.5. A variant of CJ was cloned to insert a tobacco etch virus (TEV) protease cleavage site between the protein and an N-terminal hexahistidine tag. After initial purification and buffer exchange, this protein was incubated with TEV protease (1:100 OD280) overnight at 4° C. Following TEV cleavage, the protein was reverse purified by immobilized metal affinity chromatography to remove TEV and uncleaved protein.

Figure 4A:
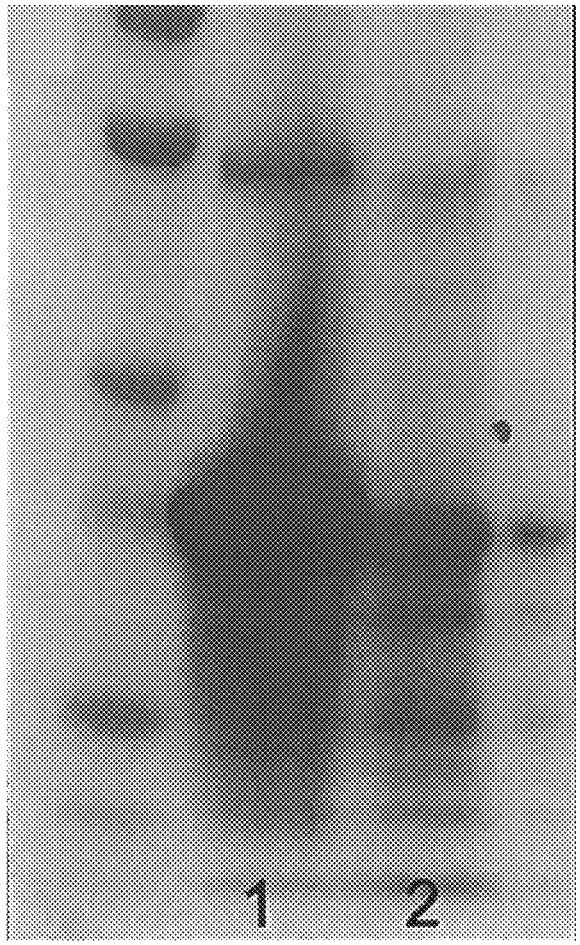
FIG. 4A and FIG. 4B depict SDS-page images of purified protein samples (1) CJ and (2) CJΔH6 after (FIG. 4A) total protein staining by Coomassie and (FIG. 4B) INVISION His-tag staining and UV transillumination.
Figure 4B:

The purified protein was characterized with SDS-Page (FIG. 4A and FIG. 4B) and crystallized overnight by sitting drop vapor diffusion at 20° C. in 20% TMAO and 65-80% MTACSIMATE at pH 7.5. Crystals were 20-50 µm in height×100-200 µm in diameter. Prior to crosslinking, crystals were washed with a 90% MLACSIMATE, 10% glycerol mixture at pH 7.5 for 30 minutes. Crystals were then transferred to a mixture of 90% MLACSIMATE and 10% glycerol at pH 7.5, and crosslinked for 2 hours by the direct addition of 1% glyoxal and 25 mM borane dimethylamine complex (DMAB). The crosslinking reaction was quenched by transfer into a solution of 0.3 M hydroxylamine and 25 mM DMAB in 0.1 M citric acid and 0.15 M NaCl at pH 5.0. After crosslinking and washing, crystals retained smooth, hexagonal morphology and clear color.

Gold Nanoparticle Synthesis:

$Au_{25}(GSH)_{18}$ was synthesized with a modified procedure briefly described in Wu, Z., Chen, J. & Jin, R. One-Pot Synthesis of Au25(SG)18 2- and 4-nm Gold Nanoparticles and Comparison of Their Size-Dependent Properties. Adv. Funct. Mater. 21, 177-183 (2011), herein incorporated by reference in its entirety. Glutathione (308.1 mg, $1 \times 10^{-3}$ mol) was added to a solution of $HAuCl_4$ (98.7 mg, $2.5 \times 10^{-4}$ mol) in 50 mL methanol. The solution was stirred to combine. The solution was initially a cloudy, yellow suspension, which after approximately five minutes of magnetic stirring turned to a clear and colorless solution. This solution was cooled at 0° C. while stirring for 30 minutes. To this, a solution of $NaBH_4$ (94.3 mg, $2.5 \times 10^{-3}$ mol) in 12.5 mL ice $H_2O$ was added rapidly with stirring. The reaction was allowed to stir for one hour at room temperature before the precipitate was spun down in 200 μL of 5 M NH$_4$OAc and MeOH at 4000 rpm. The supernatant was discarded and the precipitate was washed twice more in the same conditions and then dried. Gel purification was performed on Au$_{25}$(GS)$_{18}$ on a 24% polyacrylamide gel (Negishi, Y., Nobusada, K. & Tsukuda, T. Glutathione-Protected Gold Clusters Revisited: Bridging the Gap between Gold(I)—Thiolate Complexes and Thiolate-Protected Gold Nanocrystals. J. Am. Chem. Soc. 127, 5261-5270 (2005), herein incorporated by reference in its entirety]. Au$_{25}$(GS)$_{18}$ was extracted from the gel in H2O and precipitated in MeOH and 200 μL of 5 M NH$_4$OAc and dried.

(1.5)-N-(5-Carbobenzyloxyamino-1-carboxypentyl) iminodiacetic Acid (2)

Ligand was synthesized using a previously published synthesis protocol (Sexton, J. Z. & Ackerson, C. J. Determination of Rigidity of Protein Bound Au(144) Clusters by Electron Cryomicroscopy. J. Phys. Chem. C Nanomater. Interfaces 114, 16037-16042 (2010), herein incorporated by reference in its entirety). Briefly, bromoacetic acid (4.17 g, 0.03 mol) was dissolved in 15 mL of 2 M NaOH. This solution was cooled to 0° C. To this a solution of N$^\varepsilon$-Cbz-L-lysine (4.2 g, 0.015 mol) in 22.5 mL of 2 M NaOH was added drop by drop and stirred for two hours at 0° C. Stirring was continued overnight at room temperature. This solution was then heated to 50° C. for two hours, after which, 1 N HCl (45 mL) was added to the cooled solution. The precipitate was filtered and dried, to afford 1.5776 g of a crude white solid (2, triacid).

(1S)—N-(5-Amino-1-carboxypentyl)iminodiacetic Acid (3)

A solution of 2 (6.8 g, 0.017 mol) in 95 mL MeOH/5 mL H$_2$O and a spatula tip full of 5% Pd/C catalyst was stirred with H$_2$ at 25° C. for 24 hours. Product was filtered through celite to remove the catalyst. The solvents were evaporated to give a colorless white paste.

(1S)—N-[5-[(4-Mercaptobutanoyl)amino]-1-carboxypentyl] iminodiacetic Acid (HSNTA)

The amino derivative (3, 1 g, 0.0038 mol) was dissolved in 10 mL H$_2$O with NaHCO$_3$ (1 g, 0.0119 mol) and 4-butyrothiolactone (0.6 g, 0.0059 mol) and stirred for 15 hours at 72° C. The resultant mixture was acidified to pH 3 with acetic acid and concentrated under reduced pressure. The crude product was crystallized in absolute ethanol, filtered and washed in absolute ethanol followed by pentane, and dried under vacuum to give a light beige solid (Scheme 1, below).

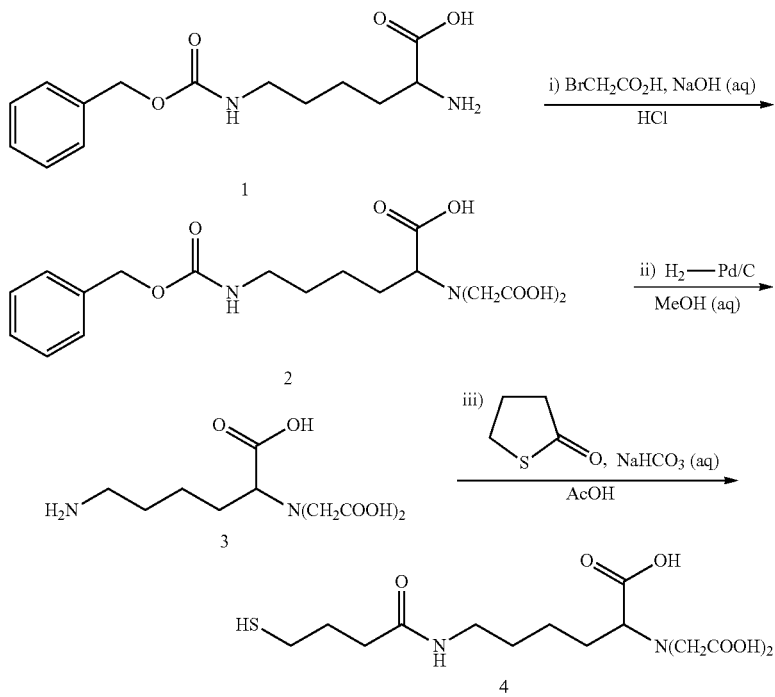

Ligand Exchange of Au$_{25}$(GS)$_{18}$:

To dried and purified Au$_{25}$(GS)$_{18}$, five equivalents of HS-NTA was added and was dissolved in H$_2$O. The reaction was allowed to shake for 7.5 minutes (Heinecke, C. L. et al. Structural and Theoretical Basis for Ligand Exchange on Thiolate Monolayer Protected Gold Nanoclusters. J. Am. Chem. Soc. 134, 13316-13322 (2012), herein incorporated by reference in its entirety). The product was then precipitated out in methanol and 200 μL 5 M NH$_4$OAc. Post centrifugation, the precipitate was dried under reduced pressure.

Imaging:

All nanoparticle uptake and release was carried out at room temperature with 10 μL samples of 1 mg/mL Au$_{25}$ solution (with or without ligand exchange) in 50 mM MES at pH 5.0. Diffusion images were captured by exciting the particles with a low power 405 nm laser pointer and imaging the emission through a 450 nm longpass filter from Edmund Optics. Images of the $Au_{25}(GSH)_{17}(NTA)$ fluorescence standards and crystal z-stack in FIG. 5 were taken using an OLYMPUS IX81 spinning-disk confocal microscope with PHOTOMETRICS Cascade II camera, a 20×0.5 numerical aperture objective with a Ix magnification changer, and Phasor holographic photoactivation system (Intelligent Imaging Innovations [3i], Denver, Colo.). Excitation was performed with a 561 nm diode laser and 692±12.5 nm single bandpass emission filter to eliminate spectral crossover. Images were acquired and analyzed with SlideBook 6.0 software [3i]. To repudiate intrinsic crystal fluorescence, an empty crosslinked 0 crystal was imaged under the optical conditions used in FIG. 5 and found to exhibit average fluorescent intensity comparable to the 0 mg/mL $Au_{25}(GSH)_{17}(NTA)$ standard. For x-ray diffraction, crystals were protected in 50% MTACSIMATE and 22% TMAO at pH 7.5. A COMPACT HOMELAB RIGAKU with a microfocus X-ray generator and a Pilatus 200K detector was used at 60 second exposure and 93 mm detector distance.

X-Ray Diffraction and Data Processing:

CJ crystals were prepared using standard protocol and loaded with 1 mg/mL gold nanoparticles for 30 minutes. After loading, a similar crystal was unloaded in the presence of 0.1 M EDTA pH 7.0 for 30 minutes. Both crystals were briefly swished through a cryoprotectant solution containing 100% MTACSIMATE and 10% glycerol at pH 7.5 prior to flash freezing in a liquid nitrogen stream (T=100 K). Crystal integrity was determined via a 10 frame (0.5°/frame, 60 second exposure) data collection strategy on a local RIGAKU COMPACT HOMELAB with a micro-focus X-ray generator and a Pilatus 200K detector. Data was integrated and scaled using HKL3000 program suite and resolution estimated to 4.26 Å after loading in gold nanoparticles and 4.27 Å after unloading in EDTA.

To attempt to resolve a CJ gold nanoparticle co-structure, a more robust crosslinking method was performed. CJ crystals were grown at concentration of 10 mg/mL in 3.4 M $(NH_4)_2SO_4$, 0.1 M Bis-Tris at pH 7.0. Crystals were transferred to a well containing 3.2 M $(NH_4)_2SO_4$, 1 mM EDTA, 10% glycerol, 50 mM Bis-Tris at pH 6.5 and allowed to wash for 30 minutes. Crystals were then transferred to an amine free crosslinking solution containing 5 M TMAO, 0.5 M $LiSO_4$, pH 7.5 (5T05L) and allowed to wash for 30 minutes. Crystals were crosslinked by transferring to 5T05L containing 1% glyoxal and incubating for 4 hours. Reductive stabilization of crosslinks was performed by a 30 minute incubation in 5T05L supplemented with 100 mM DMAB. After reduction, free aldehydes were quenched and reduced by addition of 50% hydroxylamine solution to 100 mM and incubating for 30 minutes. Crystals were loaded for 2 hours with gold nanoparticles under standard conditions. Visually, the resulting crystals appeared to have significant uptake of the gold nanoparticles (i.e., they turned red). Loaded crystals were swished through a cryoprotectant solution containing 5T05L prior to flash freezing in a liquid nitrogen stream. A full data collection set (360 frames, 0.5°/frame, 60 second exposure) was collected on the local RIGAKU HOMELAB. The data was reduced and integrated using iMosflm (Leslie, A. G. W. & Powell, H. R. in Evolving Methods for Macromolecular Crystallography (eds. Read, R. J. & Sussman, J. L.) 41-51 (Springer Netherlands, 2007), the disclosures of which are herein explicitly incorporated in their entirety) scaled using Pointless (Evans, P. Scaling and assessment of data quality. Acta Crystallographica Section D Biological Crystallography 62, 72-82 (2006), the disclosures of which are herein explicitly incorporated in their entirety). Molecular replacement was performed using Refmac (see Skubak, P., Murshudov, G. N. & Pannu, N. S. Direct incorporation of experimental phase information in model refinement. Acta Crystallographica Section D Biological Crystallography 60, 2196-2201 (2004), the disclosures of which are herein explicitly incorporated in their entirety) with 2FGS from the Protein Data Bank as a starting model. Scala output logs on a CJ crystal incubated with $Au_{25}(GSH)_{17}(NTA)$ are provide in Table 1 and Table 2. X-ray diffraction data and refinement statistics are provided in Table 3.

TABLE 1

Scala output log for 10 frame diffraction check on a CJ crystal incubated with 1 mg/mL $Au_{25}(GSH)_{17}(NTA)$ for 30 minutes.

| Lower Resolution (Å) | High Resolution (Å) | Average I | Average Error | CC½ | CC' |
|---|---|---|---|---|---|
| 50 | 10.47 | 36.8 | 1.7 | 0.999 | 1 |
| 10.47 | 8.33 | 12.6 | 1.2 | 0.989 | 0.997 |
| 8.33 | 7.28 | 4.9 | 1 | 0.911 | 0.976 |
| 7.28 | 6.61 | 5 | 1.1 | 0.995 | 0.999 |
| 6.61 | 6.14 | 2.9 | 1.2 | 0.857 | 0.961 |
| 6.14 | 5.78 | 4.1 | 1.3 | 0.816 | 0.948 |
| 5.78 | 5.49 | 2.8 | 1.3 | 0.863 | 0.963 |
| 5.49 | 5.25 | 3.1 | 1.4 | 0.786 | 0.938 |
| 5.25 | 5.05 | 3.6 | 1.6 | 0.867 | 0.964 |
| 5.05 | 4.88 | 3.4 | 1.6 | 0.671 | 0.896 |
| 4.88 | 4.72 | 3.7 | 1.7 | 0.562 | 0.848 |
| 4.72 | 4.59 | 3.9 | 1.8 | 0.866 | 0.963 |
| 4.59 | 4.47 | 4.6 | 1.8 | 0.481 | 0.806 |
| 4.47 | 4.36 | 5.7 | 1.9 | 0.061 | 0.338 |
| 4.36 | 4.26 | 5.2 | 2.1 | 0.5 | 0.823 |
| 4.26 | 4.17 | 2.6 | 2.1 | 0.25 | 0.633 |
| 4.17 | 4.09 | 2.6 | 2.2 | 0.756 | 0.928 |
| 4.09 | 4.01 | 2.2 | 2.2 | 0.424 | 0.772 |
| 4.01 | 3.94 | 1.4 | 2.3 | 0.424 | 0.772 |

TABLE 2

Scala output log for 10 frame diffraction check on a CJ crystal incubated with 1 mg/mL $Au_{25}(GSH)_{17}(NTA)$ for 30 minutes.

| Lower Resolution (Å) | High Resolution (Å) | Average I | Average Error | CC½ | CC* |
|---|---|---|---|---|---|
| 50 | 11.36 | 34.8 | 1.5 | 1 | 1 |
| 11.36 | 9.03 | 21.7 | 1.2 | 0.988 | 0.997 |
| 9.03 | 7.9 | 11.2 | 1 | 0.996 | 0.999 |
| 7.9 | 7.18 | 7 | 1 | 0.984 | 0.996 |
| 7.18 | 6.66 | 5.7 | 1.1 | 0.942 | 0.985 |
| 6.66 | 6.27 | 4.7 | 1.1 | 0.733 | 0.92 |
| 6.27 | 5.96 | 3.8 | 1.1 | 0.94 | 0.985 |
| 5.96 | 5.7 | 4.4 | 1.2 | 0.915 | 0.978 |
| 5.7 | 5.48 | 3 | 1.2 | 0.864 | 0.963 |
| 5.48 | 5.29 | 3.3 | 1.4 | 0.922 | 0.979 |
| 5.29 | 5.13 | 3.9 | 1.3 | 0.665 | 0.894 |
| 5.13 | 4.98 | 5.1 | 1.5 | 0.851 | 0.959 |
| 4.98 | 4.85 | 5.1 | 1.6 | 0.838 | 0.955 |
| 4.85 | 4.73 | 6.5 | 1.5 | 0.962 | 0.99 |
| 4.73 | 4.62 | 5.3 | 1.7 | 0.94 | 0.984 |
| 4.62 | 4.52 | 6.9 | 1.7 | 0.752 | 0.927 |
| 4.52 | 4.43 | 3.5 | 1.8 | 0.482 | 0.807 |
| 4.43 | 4.35 | 4.7 | 1.7 | 0.541 | 0.838 |
| 4.35 | 4.27 | 6.8 | 2.3 | 0.81 | 0.946 |
| 4.27 | 4.2 | 6.5 | 2 | 0.342 | 0.714 |

TABLE 3

| X-ray diffraction data and refinement statistics | |
| --- | --- |
| CC* | 0.999 (0.862) |
| Refinement | |
| Reflections used in refinement | 8207 (750) |
| Reflections used for R-free | 398 (33) |
| Rwork | 0.2349 (0.3236) |
| Rfree | 0.2625 (0.3277) |
| CC(work) | 0.943 (0.584) |
| CC(free) | 0.886 (0.789) |
| RMS(bonds) | 0.012 |
| RMS(angles) | 1.65 |
| Average B-factor | 55.12 |
| macromolecules | 55.47 |
| ligands | 48.46 |
| solvent | 30.58 |

Elemental Analysis:

The elemental analysis samples each consisted of three replicates, each containing three crystals loaded with gold nanoparticles and dissolved in 2 mL of aqua regia. Volumes were calculated by measuring side lengths and heights of the crystals. The first seven samples consisted of loading CJ crystals with $Au_{25}(GSH)_{17}(NTA)$ for the described length of time. For the eighth sample, CJ crystals were loaded with $Au_{25}(GSH)_{17}(NTA)$ for 30 minutes, then moved to a drop of 1 mM $NiSO_4$ in 20 mM HEPES pH 8.0. In the ninth sample, CJ crystals were loaded with $Au_{25}(GSH)_{17}(NTA)$ for 30 minutes, then moved to a drop of 0.1 M EDTA in 20 mM HEPES at pH 8.0. Elemental Analysis was performed at Midwest Laboratories, Inc.

REFERENCES

1. Wang, L., Xu, L., Kuang, H., Xu, C. & Kotov, N. A. Acc. Chem. Res., 2012, 45, 1916-1926.
2. Mirkin, C. A., Letsinger, R. L., Mucic, R. C. & Storhoff, J. J. Nature, 1996, 382, 607-609.
3. Funston, A. M., Novo, C., Davis, T. J. & Mulvaney, P. Nano Lett., 2009 9, 1651-1658.
4. Slaughter, L. S. et al. Nano Lett., 2012, 12, 3967-3972.
5. Nam, J.-M., Stoeva, S. I. & Mirkin, C. A. J. Am. Chem. Soc., 2004, 126, 5932-5933.
6. Alivisatos, A. P. et al. Nature, 1996, 382, 609-611.
7. Ding, B. et al. J. Am. Chem. Soc., 2010, 132, 3248-3249.
8. Rothemund, P. W. K., Nature 2006, 440, 297-302.
9. Liu, W. et. al. Science., 2016, 351, 582-586.
10. Ackerson, C. J., Sykes, M. T. & Kornberg, R. D. Proc. Natl. Acad. Sci. U.S.A., 2005, 102, 13383-13385.
11. Chen, P.-Y. et al. ACS Nano, 2013.
12. Huang, Y. et al. Nano Lett., 2005, 5, 1429-1434.
13. Szuchmacher, A., Blum, C. M. S., Nano Lett., 2004, 4.
14. Ackerson, C. J., Jadzinsky, P. D., Jensen, G. J. & Kornberg, R. D. J. Am. Chem. Soc., 2006, 128, 2635-2640.
15. Sexton, J. Z. & Ackerson, C. J., J. Phys. Chem. C Nanomater. Interfaces 2010, 114, 16037-16042.
16. Baneyx, F. & Matthaei, J. F., Curr. Opin. Biotechnol., 2014, 28, 39-45.
17. Sarikaya, M., Tamerler, C., Jen, A. K.-Y., Schulten, K. & Baneyx, F., Nat. Mater., 2003, 2, 577-585.
18. Gradigar, H. et al., Nat. Chem. Biol., 2013, 9, 362-366.
19. Kostiainen, M. et al., Nature Nanotechnology., 2013, 8, 52-56.
20. Abe, S. et al. Small Weinh. Bergstr. Ger., 2012, 8, 1314-1319.
21. Koshiyama, T. et al. Bioconjug. Chem., 2010, 21, 264-269.
22. Krauss, I. R., Merlino, A., Vergara, A. & Sica, F. Int., Mol Sci, 2013, 14, 11643-11691.
23. Szöke, A., Szöke, H. & Somoza, J. R. Acta Crystallogr. A, 1997, 53, 291-313.
24. Karle, J. Int. J. Quantum Chem., 1980, 18, 357-367.
25. Kartha, G. & Parthasarathy, R. Acta Crystallogr., 1965, 18, 745-749.
26. Gnatt, A. L., Cramer, P., Fu, J., Bushnell, D. A. & Kornberg, R. D. Science, 2001, 292, 1876-1882.
27. Takeda, Y., Kondow, T. & Mafune, F. Chem. Phys. Lett., 2011, 504, 175-179.
28. Uchinomiya, S. et al. Chem. Commun. Camb. Engl., 2009, 5880-5882 (2009).
29. Hainfeld, J. F., Liu, W., Halsey, C. M., Freimuth, P. & Powell, R. D. J. Struct. Biol., 1999, 127, 185-198.
30. Park, S., Yang, X. & Saven, J. G. Curr. Opin. Struct. Biol., 2004, 14, 487-494.
31. Saven, J. G. Curr. Opin. Colloid Interface Sci., 2010, 15, 13-17.
32. Pokala, N. & Handel, T. M. J. Struct. Biol., 2001, 134, 269-281.
33. DNASU Plasmid I Detailed Vector Information: pSB3. DNASU Plasmids at <http://dnasu.org/DNASU/GetVectorDetail.do?vectorid=383>
34. Wu, Z. & Jin, R. Nano Lett., 2010, 10, 2568-2573.

Example 2. Installing Guest Molecules at Specific Sites within Host Protein Crystals It has been previously reported that the structure of small molecules can be resolved when they are soaked into metal organic frameworks (MOFs). However, this method presented many challenges. Challenges associated with the crystalline sponge method include guest size limitations, the need to reach high occupancy, and the reliance on adventitious non-covalent interactions to drive the guest molecules to adopt a coherent structure. It was hypothesized that site-specific covalent installation would reduce the conformational freedom of guest molecules, facilitating host-guest crystallography. To systematically test this hypothesis, four different conjugation strategies were used to attach guest molecules to three different cysteine sites within an engineered protein crystal. In all but one case, the presence of the adduct was obvious in the electron density. Post-crystallization installation and structure determination of larger guests may be feasible thanks to the large pores of the engineered scaffold crystals (13 nm diameter).

Introduction

Precise position control of functional molecules in 3-dimensions will result in materials with unprecedented performance for diverse applications including biosensing, catalysis, energy conversion, biomedicine, and biotechnology. Previously, researchers have repurposed diverse natural self-assembled architectures including oligomers, fibers, cages, capsids, 2-D S-layers, and protein crystals in pursuit of nanotechnology applications. Protein crystals are an appealing platform for nanotechnology applications because X-ray diffraction (XRD) can elucidate the resulting atomic structure. Furthermore, the individual protein building blocks may be functionalized with non-biological functional groups for biohybrid materials. A major potential barrier is protein crystal plasticity; changes to the constituent monomers can disrupt crystallization. Previous functionalization of protein crystals have relied upon modification of the protein prior to crystallization, which can also alter or abrogate crystallization. Even trace labeling protein monomers with fluorophores (<10 mol %) can disrupt crystal nucleation.

The approach disclosed herein surprisingly overcomes the problems associated with prior functionalization of protein crystals. Specifically, the method disclosed herein decouples crystallization from subsequent modification steps. First, porous scaffold crystal variants are prepared that present cysteine residues proximal to large solvent channels and small molecules are subsequently installed at these sites. The resulting modified crystalline scaffolds can then be validated using XRD. By performing asynchronous crystallization and covalent small molecule installation, unprecedented control over guest molecule position in three-dimensional space was observed.

Methods

CJ Protein Crystal Preparation:

A codon optimized gene encoding a putative periplasmic protein (Genebank ID: cj0420, Protein Data Bank code: 2FGS) from *Campylobacter jejuni* was obtained from Life Technologies and cloned into pSB3 vector at NdeI and XhoI. For cytosolic expression, the gene was truncated to remove the signaling peptide. Thiol variants were generated via single primer mutagenesis with Q5 polymerase (New England Biolabs) and sequenced verified. All variants were expressed in *E. coli* C41 (DE3) (Lucigen) grown in Terrific Broth and induced with 0.4 mM IPTG at 25° C. for 16 hours. The cells were harvested and sonicated into a lysis buffer (50 mM HEPES, 500 mM NaCl, 10% glycerol, 25 mM imidazole, pH 7.4). The lysate was clarified and purified via Ni2+-NTA chromotagraphy (Thermo Fisher Scientific HIS-PUR Ni-NTA). A single chromatography step provided sufficient purity for crystallization. The purified protein was dialyzed into a storage buffer (10 mM HEPES, 500 mM $(NH_4)_2SO_4$, 10% glycerol at pH 7.4), aliquoted, and stored at -20° C. The final concentration was ~20 mg/mL with an average CJ yield of >200 mg per 1 L culture. CJ variants were crystallized overnight by sitting drop vapor diffusion at 20° C. in >3.0 M $(NH_4)_2SO_4$, 0.1 M Bis-Tris pH 6.0.

Prior to installation, crystals were washed via transfer to the installation solution (3.4 M $(NH_4)_2SO_4$, 100 mM HEPES, pH 7.5) for 15 minutes to equilibrate the crystals and remove excess free protein. Crystals were then transferred to the installation solution with 500 μM of the molecule to be conjugated and incubated for 2 hours to allow full equilibration.

Figure 6:
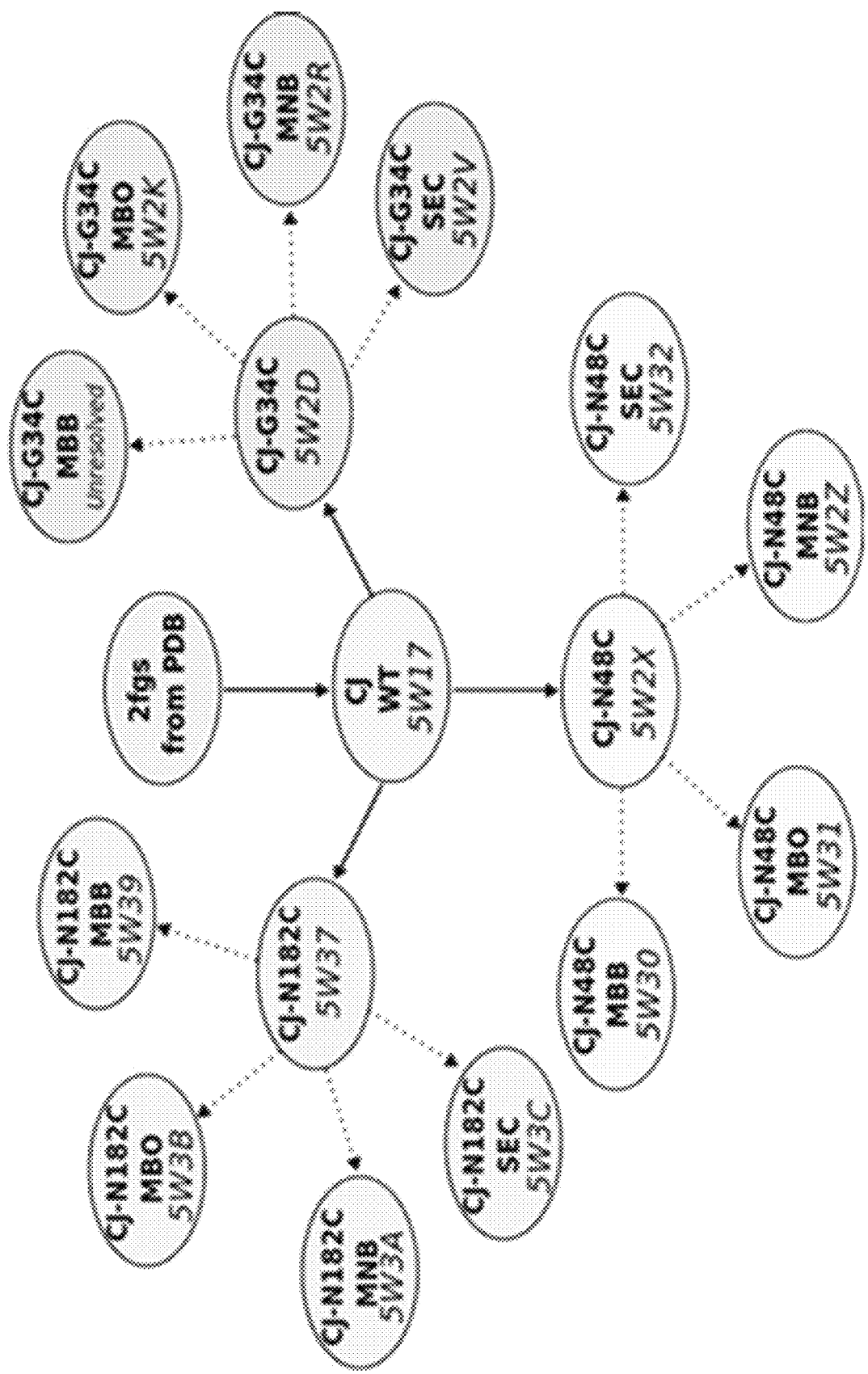
FIG. 6 depicts a diagram of molecular replacement work flow of the previously solved *Campylobacter jejuni* Ycel periplasmic protein at 2.9 Å resolution (PDB 2FGS). An updated model of the CJ Ycel periplasmic protein was obtained at improved resolution (2.58 Å), Improved resolution allowed for further refinement of side chains, modeling of ordered water, and placement of a ligand in the hydrophobic core of the protein. The identity of the hydrophobic ligand remains unknown, but a saturated C18 ligand was modeled as a placeholder. This improved model (CJ WT) served as the molecular replacement model for the reduced CJ thiol mutant crystals: G34C, N48C, and N182C. The new thiol mutant models further served as models for the resulting CJ thiol crystals conjugated with small molecules. Non-trivial changes from the input molecular replacement model were only made if there was strong reason (e.g., improved side chain resolution, disrupted hydrogen bond network, modeling new features, etc.).

X-Ray Diffraction and Data Processing:

In all cases, individual crystals were briefly swished through a cryoprotectant solution containing 3.2 M $(NH_4)_2SO_4$ and either 10% glycerol or 10% ethylene glycol at pH 7.5 and flash frozen in liquid nitrogen. X-ray diffraction data was collected on beamline 4.2.2 at the Advanced Light Source (ALS) or on a local RIGAKU COMPACT HOMELAB with a microfocus X-ray generator and a Pilatus 200K detector. The collected data was processed with XDS (Kabsch, W. XDS. *Acta Crystallogr.* D Biol. *Crystallogr.* 66, 125-132 (2010), the disclosures of which are herein incorporated by reference in their entirety). The wild-type structure was determined by molecular replacement (MR) with the *Campylobacter jejuni* putative periplasmic protein (PDB entry 2FGS) as a search model. Model refinement was performed in COOT using sigma weighted (2Fo-Fc) and (Fo-Fc) electron density maps and REFMAC5 from the CCP4 suite refinement (Emsley, P., Lohkamp, B., Scott, W. G. & Cowtan, K. Features and development of Coot. *Acta Crystallogr. D Biol. Crystallogr.* 66, 486-501 (2010); Winn, M. D. et al. Overview of the CCP4 suite and current developments. *Acta Crystallogr. D Biol. Crystallogr.* 67, 235-242 (2011); and Vagin, A. A. et al. REFMAC5 dictionary: organization of prior chemical knowledge and guidelines for its use. *Acta Crystallogr. D Biol. Crystallogr.* 60, 2184-2195 (2004), the disclosure of each are herein incorporated by reference in their entirety). The resulting wild-type model was used as the starting MR model for G34C, N48C, and N182C with the same refinement scheme. Each cysteine variant model was then used as a MR search model for their corresponding small molecule adducts FIG. 6 summarizes the model refinement scheme.

Results

Solvent exposed residues on the surface of the CJ axial pores were individually mutated to cysteine. These binding sites were selected to maximize the inter-site distance between symmetry copies throughout the crystal (FIG. 14). Chemical conjugation via engineered surface cysteine residues is appealing due to the absence of cysteine residues in wild-type CJ crystals (SEQ ID NO. 3) and the diverse, established chemistry for thiol conjugation.

While the cysteine mutations could have, in principle, altered or abrogated crystallization, P622 crystals for the variants G34C (SEQ ID NO. 4), N48C (SEQ ID NO. 5), and N182C (SEQ ID NO. 6) were obtained.

Solvent channels within protein crystals have been used in classical protein crystallography for diffusion of heavy atoms for protein crystal phasing. Mercury derivatives are particularly useful due the well documented propensity of thiols to covalently bind mercury (FIG. 16) (Sun, D. P., Alber, T., Bell, J. A., Weaver, L. H. & Matthews, B. W. Use of site-directed mutagenesis to obtain isomorphous heavy-atom derivatives for protein crystallography: cysteine-containing mutants of phage T4 lysozyme. *Protein Eng.* 1, 115-123 (1987), herein incorporated by reference in its entirety). To demonstrate engineered thiol accessibility, CJ cysteine mutant crystals were exposed to hydroxymercuribenzoate (MBO), and XRD was subsequently performed. Obvious difference map peaks were observed for all three cysteine-variants (FIG. 15, panels c, i, and o). MBO ligand was fit with 85% occupancy for N48C and 90% occupancy for G34C. The electron density suggested clear directionality for the benzoic acid group for the N48C adduct, but not for G34C. N182C had an extended electron density feature suggesting multiple states and was fit to two 50%-occupancy states (FIG. 15, panel o).

Free thiols can be oxidized to mixed disulfide via disulfide exchange reactions (FIG. 17). Ellman's reagent, 5,5'-dithiobis(2-nitrobenzoic acid) (DTNB), a compound useful for the quantitative determination of sulfhydryls in solution, was selected as the target molecule to demonstrate disulfide exchange on the crystal due to its chromogenic properties. Addition of Ellman's reagent to CJ variants in solution proceeded to near completion as confirmed by absorbance at 412 nm (FIG. 16). When CJ cysteine mutant crystals were exposed to DTNB, the crystals temporarily acquired a faint yellow hue before MNB could diffuse out of the crystals. After washing the crystals to remove excess DTNB, an intense yellow signal could be observed for all three cysteine variants by adding 20 μL of 10 mM 2-mercaptoethanol (BME) (FIG. 19). XRD diffraction elucidated a single conformation for installed 5-mercapto-2-nitro-benzoic acid (MNB) ligand on all three cysteine variants at 100% occupancy (FIG. 15, panels d, j, and p). Thiols can also undergo rapid interchange reactions with diselenide compounds to form mixed thiol-selenide compounds (FIG. 20). After incubation with selenocystine, XRD revealed modifications on all three cysteine variants indicative of selenocysteine (SEC)

installation (FIG. 15, panels e, k, and q). SEC ligand could be fit to two conformations at 50% occupancy for G34C and a single 90%-occupancy conformation for N48C. Beyond the heavy selenium atom, the rest of the conjugate was not obvious for both variants. While the S—Se bond formation appears to have a preferred geometry (±90° dihedral), the rest of the conjugate has free rotatable bonds leading to disorder. The electron density for SEC installation at N182C revealed clearer directionality of the conjugate with a single state at 100% occupancy (FIG. 15, panel q).

Haloalkyl derivatives are some of the most widely used conjugates for modifying thiols. The nucleophilic thiolate of the protein reacts with the halogenated alkyl via an SN2 reaction forming a stable thioether linkage (FIG. 21). Due to its fluorogenic properties, monobromobimane (mBBr), was selected as the target reagent for demonstrating halo-alkyl installation ($\lambda_{exc}/\lambda_{emm}$=394/490). mBBr is essentially non-fluorescent until conjugated to a thiol. CJ cysteine bearing crystals were exposed to mBBr and the fluorescence was monitored via confocal microscopy. Only crystals containing thiol mutations were fluorescent (FIG. 22A and FIG. 22B). XRD was performed on the resulting crystals and installation was observed on N48C and N182C. A bimane adduct (MBB) could be fit to a single conformation for N48C and N182C at 90% and 100% occupancy respectively (FIG. 15, panels l and r).

The results presented herein confirm multiple types of post-crystallization conjugation chemistry at multiple sites on a protein. The XRD results are summarized in Table 4. Of the attempted structure determination attempts, only one cysteine:adduct pair (mBBr installation at G34C) has yet to yield interpretable electron density for the guest molecule. Notably, the G34C crystal became highly fluorescent when incubated with mBBr which suggest that installation was still successful in this case. It is not uncommon for surface sidechain disorder to lead to ambiguous or absent electron density contours (e.g., FIG. 15).

TABLE 4

Summary of XRD Results.

|  |  | MBO | MNB | SEC | MBB |
|---|---|---|---|---|---|
| G34C | Rating | ●●○○○ | ●●●●● | ●●○○○ | ●○○○○ |
|  | Ligand Detail | Hg atom only | Fully resolved | Se atom only multiple states | Small peak unresolved |
|  | PDB Code | 5W2K | 5W2R | 5W2V | — |
| N48C | Rating | ●●●●● | ●●●●○ | ●●●○○ | ●●●●○ |
|  | Ligand Detail | Fully resolved | Mostly resolved | Se atom and alpha carbon only | Mostly resolved |
|  | PDB Code | 5W31 | 5W2Z | 5W32 | 5W30 |
| N182C | Rating | ●●●○○ | ●●●●● | ●●●●● | ●●●●● |
|  | Ligand Detail | Multiple states too complex | Fully resolved | Fully resolved | Fully resolved |
|  | PDB Code | 5W3B | 5W3A | 5W3C | 5W39 |

SUMMARY

The results presented herein demonstrate that several standard thiol conjugation strategies accessible to those with skill in the art are suitable for installing molecules upon engineered cysteine residues in a three-dimensional protein crystal. This strategy will enable diverse nanotechnological applications. The elucidation of atomic level structures of the resulting small molecule conjugates is promising for advancing techniques in host-guest crystallography. The strategies demonstrated here could be used to conjugate small molecules of unknown structure to engineered, high-resolution protein crystal scaffolds. Alternately, in contrast to the MOFs used in the crystalline sponge method, (Inokuma, Y. et al. X-ray analysis on the nanogram to microgram scale using porous complexes. Nature 495, 461-466 (2013), herein incorporated by reference in its entirety) the 13-nm pores of CJ crystals are large enough to accommodate macromolecules such as proteins, inorganic nanoparticles, and DNA. The methods developed herein lay the groundwork for site-specific installation of macromolecules and structure determination of the resulting host-guest complexes.

REFERENCES

1. Seeman, N. C. Nucleic acid junctions and lattices. J. Theor. Biol. 99, 237-247 (1982).
2. Inokuma, Y. et al. X-ray analysis on the nanogram to microgram scale using porous complexes. Nature 495, 461-466 (2013).
3. Ledford, H. Controversial molecular-analysis tool tries for a comeback. Nature (2015). doi:10.1038/nature.2015.17702
4. Pandya, M. J. et al. Sticky-end assembly of a designed peptide fiber provides insight into protein fibrillogenesis. Biochemistry (Mosc.) 39, 8728-8734 (2000).
5. Potekhin, S. A. et al. De novo design of fibrils made of short alpha-helical coiled coil peptides. Chem. Biol. 8, 1025-1032 (2001).
6. Ogihara, N. L. et al. Design of three-dimensional domain-swapped dimers and fibrous oligomers. Proc. Natl. Acad. Sci. U.S.A. 98, 1404-1409 (2001).
7. Padilla, J. E., Colovos, C. & Yeates, T. O. Nanohedra: using symmetry to design self assembling protein cages, layers, crystals, and filaments. Proc. Natl. Acad. Sci. U.S.A. 98, 2217-2221 (2001).
8. Lai, Y.-T., Cascio, D. & Yeates, T. O. Structure of a 16-nm Cage Designed by Using Protein Oligomers. Science 336, 1129-1129 (2012).
9. King, N. P. et al. Computational design of self-assembling protein nanomaterials with atomic level accuracy. Science 336, 1171-1174 (2012).
10. Douglas, T. & Young, M. Viruses: Making Friends with Old Foes. Science 312, 873-875 (2006).
11. Lee, S.-Y., Lim, J.-S. & Harris, M. T. Synthesis and application of virus-based hybrid nanomaterials. Biotechnol. Bioeng. 109, 16-30 (2012).
12. Moll, D. et al. S-layer-streptavidin fusion proteins as template for nanopatterned molecular arrays. Proc. Natl. Acad. Sci. 99, 14646-14651 (2002).
13. Sleytr, U. B., Egelseer, E. M., Ilk, N., Pum, D. & Schuster, B. S-Layers as a basic building block in a molecular construction kit. FEBS J. 274, 323-334 (2007).
14. Baneyx, F. & Matthaei, J. F. Self-assembled two-dimensional protein arrays in bionanotechnology: from S-layers to designed lattices. Curr. Opin. Biotechnol. 28, 39-45 (2014).
15. Wei, H. et al. Time-dependent, protein-directed growth of gold nanoparticles within a single crystal of lysozyme. Nat. Nanotechnol. 6, 93-97 (2011).
16. McElroy, H. E., Sisson, G. W., Schoettlin, W. E., Aust, R. M. & Villafranca, J. E. Studies on engineering crystallizability by mutation of surface residues of human thymidylate synthase. J. Cryst. Growth 122, 265-272 (1992).
17. D'Arcy, Stihle, M., Kostrewa, D. & Dale, G. Crystal engineering: a case study using the 24 kDa fragment of the DNA gyrase B subunit from *Escherichia coli*. Acta Crystallogr. D Biol. Crystallogr. 55, 1623-1625 (1999).
18. Forsythe, E., Achari, A. & Pusey, M. L. Trace fluorescent labeling for high-throughput crystallography. Acta Crystallogr. D Biol. Crystallogr. 62, 339-346 (2006).
19. Koshiyama, T. et al. Modification of porous protein crystals in development of biohybrid materials. Bioconjug. Chem. 21, 264-269 (2010).
20. Huber, T. R., Hartje, L. F., McPherson, E. C., Kowalski, A. E. & Snow, C. D. Programmed Assembly of Host—Guest Protein Crystals. Small 10.1002/smll.201602703 (2016). doi:10.1002/smll.201602703
21. Kowalski, A. E. et al. Gold nanoparticle capture within protein crystal scaffolds. Nanoscale 8, 12693-12696 (2016).
22. Hermanson, G. T. Bioconjugate Techniques. (Academic Press, 2013).
23. Pike, A. C. W., Garman, E. F., Krojer, T., von Delft, F. & Carpenter, E. P. An overview of heavy-atom derivatization of protein crystals. Acta Crystallogr. Sect. Struct. Biol. 72, 303-318 (2016).
24. Sun, D. P., Alber, T., Bell, J. A., Weaver, L. H. & Matthews, B. W. Use of site-directed mutagenesis to obtain isomorphous heavy-atom derivatives for protein crystallography: cysteine-containing mutants of phage T4 lysozyme. Protein Eng. 1, 115-123 (1987).
25. Ellman, G. L. Tissue sulfhydryl groups. Arch. Biochem. Biophys. 82, 70-77 (1959).
26. Riddles, P. W., Blakeley, R. L. & Zerner, B. Reassessment of Ellman's reagent. Methods Enzymol. 91, 49-60 (1983).
27. Winther, J. R. & Thorpe, C. Quantification of Thiols and Disulfides. Biochim. Biophys. Acta 1840, (2014).
28. Beld, J., Woycechowsky, K. J. & Hilvert, D. Diselenides as universal oxidative folding catalysts of diverse proteins. J. Biotechnol. 150, 481-489 (2010).
29. Steinmann, D., Nauser, T. & Koppenol, W. H. Selenium and Sulfur in Exchange Reactions: A Comparative Study. J. Org. Chem. 75, 6696-6699 (2010).
30. Sardi, F. et al. Determination of acidity and nucleophilicity in thiols by reaction with monobromobimane and fluorescence detection. Anal. Biochem. 435, 74-82 (2013).
31. Kabsch, W. XDS. Acta Crystallogr. D Biol. Crystallogr. 66, 125-132 (2010).
32. Emsley, P., Lohkamp, B., Scott, W. G. & Cowtan, K. Features and development of Coot. Acta Crystallogr. D Biol. Crystallogr. 66, 486-501 (2010).
33. Winn, M. D. et al. Overview of the CCP4 suite and current developments. Acta Crystallogr. D Biol. Crystallogr. 67, 235-242 (2011).
34. Vagin, A. A. et al. REFMAC5 dictionary: organization of prior chemical knowledge and guidelines for its use. Acta Crystallogr. D Biol. Crystallogr. 60, 2184-2195 (2004).

Example 3. Crosslinking

Introduction

The disclosure herein compares the crosslinking chemistry of GA, formaldehyde, glyoxal, and 1-ethyl-3-(3-dimethylaminopropyl) carbodiimide hydrochloride (EDC) for their ability to effectively stabilize crystals composed of CJ, a putative periplasmic protein from *Campylobacter jejuni* (cj0420). Alongside these reagents, urea and guanidinium were also tested as additive compounds to facilitate the creation of additional or alternative intermolecular connections. Crosslinking agent performance as a function of time was also quantified.

Methods

Crystal Growth:

Target crystals were composed of CJ1 (*Campylobacter jejuni* YCEI protein, PDB structure: 2FGS) wild type. Sitting drop vapor diffusion was used to crystalize this protein. The reservoir solution contained 3.1 to 3.5M Ammonium Sulfate buffered at pH 6.0 with Bis-Tris (2-[Bis (2-hydroxyethyl)amino]-2-(hydroxymethyl)propane-1,3-diol). Protein samples were concentrated to approximately 8-15 mg/ml. Crystals of usable size were usually formed after about 1-3 days.

Preparation:

0.15-0.30 mm diameter crystals were transferred directly into 4.0 M aqueous $TMAO-SO_4$ (Trimethylamine N-oxide titrated with sulfuric acid to reach desired pH) pH 7.5 and incubated for at least 5 minutes. Next, 200 μL crosslinking solutions were made to contain appropriate concentrations of TMAO, crosslinker and additive if applicable (Table 5). All crosslinkers were taken from stocks that were opened fresh, aliquoted and immediately stored at −30° C. The wells were mixed before the addition of the crystals. Approximately 5 crystals per condition were placed into the crosslinking solution with not more than 1 minute between preparing the well, and transferring the crystal to the well. All experiments were conducted in PYREX borosilicate glass depression well plates, and sealed with VWR glass cover slips and DOW vacuum grease. Each experiment had a separate well allocated for various time points so as to not disrupt the vapor headspace. The time points used were short (30 minutes), medium (2 hours), and long term (24 hours). After exposure to crosslinking solution for the desired amount of time, they were looped immediately into a challenging condition: 50% glycerol in water and let sit for 5 minutes. Crystals were then quickly transferred into liquid nitrogen and cryogenically stored under liquid nitrogen until analyzed with cryogenic X-Ray diffraction (XRD).

X-Ray Diffraction and Data Processing:

CJ crystals were prepared using standard protocols. In all cases, crystals were kept in their cryoprotectant solution (50% glycerol in water) under liquid nitrogen in a cryogenic vial prior to XRD. Loops were then serially transferred to a RIGAKU HOMELAB, exposing the crystal to a liquid nitrogen stream (T=100 K) to prevent the crystal from thawing. Crystal integrity was quantified via a 10 frame (0.5° per frame, 60 second exposure) data collection strategy using a microfocus X-ray generator and a Pilatus 200K detector. Data were integrated and scaled using the HKL3000 program suite.

TABLE 5

| Crosslinking Reagents | | |
|---|---|---|
| Key Reagents | Solution composition | pH |
| Formaldehyde | 4.2M $TMAO-SO_4$<br>0.2M Formaldehyde | 7.5 |
| Formaldehyde + Urea | 4.2M $TMAO-SO_4$<br>0.2M Formaldehyde<br>0.02M Urea | 7.5 |

TABLE 5-continued

Crosslinking Reagents

| Key Reagents | Solution composition | pH |
|---|---|---|
| Formaldehyde + Guanidinium HCL | 4.2M TMAO-SO$_4$<br>0.2M Formaldehyde<br>0.02M Guanidinium HCL | 7.5 |
| Glyoxal | 4.2M TMAO-SO$_4$<br>0.2M Glyoxal | 7.5 |
| Glyoxal + DMAB | 4.2M TMAO-SO$_4$<br>0.2M Glyoxal<br>0.02M DMAB | 7.5 |
| Glutaraldehyde | 4.2M TMAO-SO$_4$<br>0.025M Glutaraldehyde | 7.5 |
| Glutaraldehyde + DMAB | 4.2M TMAO-SO$_4$<br>0.025M Glutaraldehyde<br>0.01M DMAB | 7.5 |
| EDC | 4.2M TMAO-SO$_4$<br>0.2M EDC | 7.5 |
| EDC + Imidazole | 4.2M TMAO-SO$_4$<br>0.2M EDC<br>0.05M Imidazole | 7.5 |

Results

To assess crystal structure quality, resolution was selected as the primary criteria. This is not a perfect quantification method but was chosen as a starting point. In X-ray crystallography, resolution is a statistical parameter which approximately represents the scale of the smallest resolvable features in the resulting electron density map. The better the resolution (the lower the reported resolution number), the more clearly the molecular structural model can be defined. To compare XRD datasets, a fixed resolution estimate was used, placing the cutoff such that the signal to noise of the diffraction pattern was at least 2.

From the collected data (Table 6), it was easy to differentiate crosslinker performance with respect to preserving diffraction despite challenging conditions. The direct addition of glutaraldehyde seemed to universally destroy resolution at the time points chosen. Notably, diffracting CJ crystals using vapor diffusion of glutaraldehyde has been achieved, but repeatability was a challenge. Extended crosslinking for glyoxal also seemed to reduce diffraction quality. On the other end of the spectrum, brief crosslinking with formaldehyde and urea appeared to provide high quality diffraction. With the aforementioned exceptions, the remaining datasets had a fairly uniform quality, diffracting to about 3.4-3.6 Å.

TABLE 6

Resolution Estimates in Angstroms (Last shell sig/I > 2)

| Key Reagent(s) | Time [hr] | 1 | 2 | 3 | AVG | STDEV |
|---|---|---|---|---|---|---|
| Formaldehyde | 0.5 | Dissolved | | | NA | |
| | 2 | | | | | |
| | 24 | 3.4 | 3.33 | 3.25 | 3.33 | 0.08 |
| Formaldehyde + GnHCl | 0.5 | 3.5 | 3.41 | 3.33 | 3.41 | 0.09 |
| | 2 | 3.49 | 3.33 | 3.41 | 3.41 | 0.08 |
| | 24 | 3.71 | 3.59 | 3.46 | 3.59 | 0.13 |
| Formaldehyde + Urea | 0.5 | 3.14 | 3.03 | 3.14 | 3.10 | 0.06 |
| | 2 | 3.15 | 3.26 | 3.41 | 3.27 | 0.13 |
| | 24 | 3.41 | 3.41 | 3.41 | 3.41 | 0.00 |
| Glyoxal | 0.5 | 3.5 | 3.26 | 3.41 | 3.39 | 0.12 |
| | 2 | 3.41 | 3.41 | 3.41 | 3.41 | 0.00 |
| | 24 | 3.58 | 4.06 | 4.28 | 3.97 | 0.36 |
| Glyoxal + DMAB | 0.5 | 3.46 | 3.43 | 3.5 | 3.46 | 0.04 |
| | 2 | 3.63 | 3.59 | 3.5 | 3.57 | 0.07 |
| | 24 | 6.1 | 6 | 4.31 | 5.47 | 1.01 |

TABLE 6-continued

Resolution Estimates in Angstroms (Last shell sig/I > 2)

| Key Reagent(s) | Time [hr] | 1 | 2 | 3 | AVG | STDEV |
|---|---|---|---|---|---|---|
| Glutaraldehyde | 0.5 | 8.14 | 6.6 | * | | NA |
| | 2 | * | * | * | | |
| | 24 | * | * | * | | |
| Glutaraldehyde + DMAB | 0.5 | * | * | * | | |
| | 2 | * | * | * | | |
| | 24 | * | * | * | | |
| EDC | 0.5 | * | * | * | | |
| | 2 | 3.58 | 3.41 | 3.47 | 3.49 | 0.09 |
| | 24 | 3.7 | 3.58 | 3.51 | 3.60 | 0.10 |
| EDC + Imidazole | 0.5 | Dissolved | | | NA | |
| | 2 | 3.41 | 3.41 | 3.5 | 3.44 | 0.05 |
| | 24 | 3.59 | 3.82 | 3.5 | 3.64 | 0.17 |

** = Insufficient diffraction to estimate a resolution.

It is important to note that the modest resolution of these datasets is in keeping with the intrinsic attributes of the crystal. Specifically, the crystal is highly porous, with a solvent fraction of about 80%. Crystals with a high solvent fraction have a marked tendency to diffract more poorly than crystals with a low solvent fraction.

In several cases, our time course revealed insufficient crosslinking. Formaldehyde by itself, required an extended incubation (>2 hours) to stabilize the crystal enough to survive in the absence of salt. Similarly, EDC or EDC-Imidazole required more than 30 minutes to achieve a sufficient crosslinking density to survive challenge. The non-catalyzed EDC 0.5 hours would likely have dissolved in the 50% glycerol solution if given a longer time in the solution. At the present time it is not known to what extent a fully covalent network is required to withstand dramatic changes in the solution condition. Universally, it was also observed that longer crosslinking times correlated with worsening resolution.

Despite the inherent crystal-to-crystal variation in diffraction quality, the XRD experiments appeared to be quite consistent and repeatable. With the exception of GA at 0.5 hours, the standard deviation of all sets for resolution was relatively low. Coincidentally, the estimated resolution values for the three glyoxal-DMAB crystals were identical.

For the experiments described herein, crystals of fairly uniform size (diameter of ~200 µm and height of ~40 µm) were used.

Strikingly, glutaraldehyde was, by far, the worst crosslinking agent with respect to preserving diffraction under challenging conditions. The only GA experiment to produce significant diffraction was on the short time scale, and only some of the crystals diffracted.

To perform XRD, a crystal is exposed to X-ray radiation. Constructive interference of the leads to intense reflections on the detector. A full dataset, diffraction patterns obtained during crystal rotation, can be processed to ultimately resolve the structure of the crystal. To obtain a resolution estimates for each crystal in a reasonable time frame, 10 XRD exposures (30 seconds) were collected on each crystal to obtain the resolution estimates. Example diffraction images for individual frames are shown in FIG. 23A, FIG. 23B, FIG. 24A, and FIG. 24B.

FIG. 23A and FIG. 23B illustrate the high-resolution and low resolution extremes. Exposure to the formaldehyde-urea mixture for 0.5 hours (FIG. 23A) diffractions to 3.03 Å, while a crystal crosslinked for 30 minutes in GA (FIG. 23B) only diffracts to ~8.14 Å. Nonetheless, the presence of the low-resolution reflections nonetheless provide confidence that the larger crystal topology (a hexagonal array of nanopores) is conserved.

However, resolution is not the only pertinent quality metric. Significant crystal mosaicity as a function of crosslinking conditions has also been observed. For example, a crystal crosslinked in EDC-imadazole for 2 hour had low mosaicity (~0.9° FIG. 24A) while a crystal crosslinked in just EDC for 2 hours (FIG. 24B) had a higher mosaicity of ~1.8°.

SUMMARY

One of the more widely reported protein crosslinkers is glutaraldehyde. Despite the popularity of glutaraldehyde as a previous crosslinker the end products are not generally clear. The exception that proves the rule was provided by Wine et al., who were able to model specific species into the crosslinks for HEWL crystals (Wine Y., Cohen-Hadar, N. Freeman A., Frolow, F. *Biotechnol. Bioeng.* 2007, 98(3): 711-8). For a simple mechanistic perspective, the Schiff base formed in glutaraldehyde crosslinking is cleavable by hydroxylamine, in practice this effect is not observed suggesting conjugate structures are likely occurring. Migneault et al. gave insight into some of the more complex structures liable to form at a variety of pHs. Though its reactivity with proteins in a range of conditions can be advantageous, for our purposes that fact is moot due to its propensity to drastically reduce x-ray diffraction quality.

In the case of formaldehyde and urea crosslinking, the ordered structure was well preserved across the time points tested. Formaldehyde and urea may polymerize to form crosslinks not observed in the formaldehyde only solutions. A greater number of conjugate sites that do not perturb the crystalline structure is desirable, but the formaldehyde and urea polymers were liable to hydrolysis as evident by dissolution of the crystal in 50% glycerol after 24 hours.

The glutaraldehyde and formaldehyde cases demonstrated a need for crosslinking protocols that can form non-reversible linkages with extensions that do not degrade crystallinity. It would stand to reason that glyoxal would also fall into this problematic category due to its chemical similarity to the aforementioned molecules. However, under acidic conditions glyoxal linkages were preserved. This result suggests that other mechanisms are present beyond the expected linkage via two Schiff bases. Simethylamine borane (DMAB) should selectively reduce Schiff bases to form permanent linkages, but this proved unnecessary due to the surprising stability of the glyoxal only crosslink.

Following testing aldehyde based crosslinking agents, EDC was investigated next. This zero-length crosslinker predominantly activates carboxylic acids, but may also react with hydroxyls. While the amide bond formation from a carboxylic acid to amine crosslink are known to be stable, end products formed by reactions with hydroxyls are prone to hydrolysis or cleavage with nucleophiles. Interestingly, EDC-crosslinked crystals dissolved in the presence of nucleophiles such as hydroxylamine. Thus, it is hypothesized that hydroxyl based crosslinks with EDC accounted for the enhanced stability observed in the crystal.

It has been demonstrated herein that a protein crystal can be stabilized with a variety of crosslinkers not traditionally used in crystallography. These results merely scratch the surface of the bioconjugation strategies that could be employed to stabilize protein crystalline materials.

REFERENCES

1. Marquië, C. (2001). Chemical Reactions in Cottonseed Protein Cross-Linking by Formaldehyde, Glutaraldehyde, and Glyoxal for the Formation of Protein Films with Enhanced Mechanical Properties. *Journal of Agricultural and Food Chemistry,* 49(10), 4676-4681. doi:10.1021/jf101152
2. Migneault, I., Dartiguenave, C., Bertrand, M., & Waldron, K, (2004), Glutaraldehyde: behavior in aqueous solution, reaction with proteins, and application to enzyme cross-linking, *BioTechniques,* (37), 790-802.
3. Metz, a, Kersten, G. F., Baart, C. J., Jong, A. D., Meiring, H., Hove, J. T., . . . Jiskoot, W. (2006). Identification of Formaldehyde-Induced Modifications in Proteins: Reactions with Insulin. *Bioconjugate Chemistry,* 17(3), 815-822. doi:10.1021/bc050340f
4. Wine, Y., Cohen-Hadar, N., Freeman, A. & Frolow, F. (2007). Elucidation of the mechanism and end products of glutaraldehyde crosslinking reaction by X-ray structure analysis. *Biotechnology and Bioengineering,* 98(3), 711-718, doi:10.1002/bit.21459
5. Thews, J., Rogalski, J. C., Clark, T. J., & Kast, J. (2008). Mass spectrometric identification of formaldehyde-induced peptide modifications under in vivo protein crosslinking conditions. *Analytica Chimica Acta,* 618(2), 168-183. doi:10.1016/j.aca.2008.04.049
6. Yan, E., et al. (2015). Cross-linked protein crystals by glutaraldehyde and their applications. *RSC Adv.,* 5(33), 26163-26174. doi:10.1039/c5ra01722j
7. Nair, B., & Francis, D. (1983). Kinetics and mechanism of urea-formaldehyde reaction, *Polymer,* 24.
8. Salamone, J. C. (1996). *Polymeric materials encyclopedia.* Boca Raton, Fla.: CRC Press.
9. Hermanson, G. T. (1996). *Bioconjugate techniques,* San Diego, Calif.: Acad. Press.
10. Huber, T. R., Hartje, L. F., Mcpherson, E. C., Kowalski, A. E., & Snow, C. D. (2016). Programmed Assembly of Host-Guest Protein Crystals. *Small,* 13(7), 1602703. doi:10.1002/smll.201602703
11. Kowalski, A. E., Huber, T. R., Ni, T. W., Hartje, L. F., Appel, K. L, Yost, J. W., . . . Snow, C. D. (2016). Gold nanoparticle capture within protein crystal scaffolds. *Nanoscale,* 8(25), 12693-12696. doi:10.1039/c6nr03096c All cited references are herein expressly incorporated by reference in their entirety.

Whereas particular embodiments have been described above for purposes of illustration, it will be appreciated by those skilled in the art that numerous variations of the details may be made without departing from the disclosure as described in the appended claims.

What is claimed is:

1. A composition comprising an engineered porous protein crystal and at least one guest molecule,
wherein the engineered porous protein crystal comprises:
at least one pore having a diameter equal to or greater than 3 nm wherein the at least one pore's diameter is large enough to permit entry of the entirety of at least one guest molecule into the pore; and
at least one binding site for the at least one guest molecule within the interior of the at least one pore, and
wherein the at least one guest molecule comprises a metal nanoparticle, a biomacromolecule, or a combination thereof, and is bound to the engineered porous protein crystal at the at least one binding site.

2. The composition of claim 1, wherein the engineered porous protein crystal has a pore diameter equal to or greater than 10 nm.

3. The composition of claim 1, wherein the engineered porous protein crystal comprises covalent bonds between constituent molecules.

4. The composition of claim 3, wherein the covalent bonds are formed between two sulfhydryl containing amino acids.

5. The composition of claim 3, wherein the covalent bonds are the result of applying at least one aldehyde crosslinking agent selected from formaldehyde, glyoxal, and combinations thereof.

6. The composition of claim 3, wherein the covalent bonds are formed between a carboxylate containing amino acid and an amine containing amino acid using at least one cabodiimide crosslinking agent.

7. The composition of claim 1, wherein the at least one guest molecule is a metal nanoparticle.

8. The composition of claim 7, wherein the nanoparticle comprises at least one atom selected from the group consisting of Au, Ag, Cu, Pt, Pd, Ru, Fe, Cd, Se, Si, and Ni.

9. The composition of claim 1, wherein the at least one guest molecule is a biomacromolecule.

10. The composition of claim 9, wherein the biomacromolecule is selected from the group consisting of a DNA sequence, an RNA sequence, a protein, and an enzyme.

11. The composition of claim 1, wherein the at least one guest molecule further comprises a linker.

12. The composition of claim 11, wherein the linker comprises a chemical entity that binds a metal ion.

13. The composition of claim 1, wherein the porous protein crystal is selected from a YCEI protein from *Campylobacter jejuni*, a pyridine nucleotide-disulfide family oxidoreductase from *Enterococcus faecalis*, a major tropism determinant P1 in complex with pertactin extracellular domain from *Bordetella bronchiseptica* and *Bordetella* virus bpp1, a putative cell adhesion protein (BACOVA_04980) from *Bacteroides ovatus*, Pyk2 (proline-rich tyrosine kinase 2) in complex with paxillin from *Gallus gallus*, and the NHR2 domain of the fusion protein AML1-ETO from *Homo sapiens*.

14. The composition of claim 1, wherein the at least one binding site is selected from the group consisting of an amino acid, a peptide sequences, and combinations thereof.

15. The composition of claim 1, wherein the porous protein crystal and the at least one guest molecule are engineered to each have at least one metal-affinity motif.

16. The composition of claim 15, wherein the at least one metal-affinity motif consists of a peptide sequence comprising at least one histidine residue.

17. A kit for determining the molecular structure of at least one guest molecule conjugated to an engineered porous protein crystal, wherein the engineered porous protein crystal is identified in the composition of claim 1.

18. A method for preparing a porous protein crystal guest molecule conjugate, the method comprising:
obtaining a porous protein crystal, wherein the porous protein crystal comprises at least one pore and at least one binding site for the at least one guest molecule within the interior of the at least one pore, wherein the at least one pore's diameter is large enough to permit entry of the entirety of at least one guest molecule into the pore, and wherein the porous protein crystal has been reacted with a crosslinking agent to produce a crosslinked porous protein crystal and the crosslinking agent bonds adjacent monomers of the porous protein crystal, wherein the crosslinking agent comprises at least one functional group selected from N-hydroxysuccinimide (NHS ester), imidoester, maleimide, pyridyldithiol, carbodiimide, aldehyde, and combinations thereof, and wherein the at least one guest molecule comprises a metal nanoparticle, a biomacromolecule, or a combination thereof; and
incubating the crosslinked porous protein crystal with at least one guest molecule to produce a porous protein crystal guest molecule conjugate.

19. The method of claim 18, further comprises incubating the porous protein crystal guest molecule conjugate with at least one metal ion to produce a stable porous protein crystal guest molecule conjugate.

20. The method of claim 19, wherein the at least one metal ion is selected from the group consisting of Ni, Cu, Zn, Fe, and Co.

21. The method of claim 19, wherein the incubation is about 1 hour.

22. The method of claim 18, wherein the porous protein crystal and the at least one guest molecule are engineered to each have at least one metal-affinity motif.

23. The method of claim 22, wherein the at least one metal-affinity motif consists of a peptide sequence comprising at least one histidine residue.

24. The method of claim 18, wherein the crosslinking agent is selected from the group consisting of 1-Ethyl-3-[3-dimethylaminopropyl] carbodiimide hydrochloride (EDC); formaldehyde; formaldehyde and urea formaldehyde and guanidinium hydrochloride; glyoxal; glyoxal and p-dimethylaminobenzaldehyde (DMAB); glutaraldehyde and p-dimethylaminobenzaldehyde (DMAB); 1-Ethyl-3-[3-dimethylaminopropyl] carbodiimide hydrochloride (EDC); 1-Ethyl-3-[3-dimethylaminopropyl] carbodiimide hydrochloride (EDC) and imidazole; 1-Ethyl-3-[3-dimethylaminopropyl] carbodiimide hydrochloride (EDC) and N-hydroxysulfosuccinimide (Sulfo-NHS); 1-Ethyl-3-[3-dimethylaminopropyl] carbodiimide hydrochloride (EDC) and malonic acid; or a crosslinking agent with two or more N-hydroxysuccinimide (NHS ester) functional groups.

25. The method of claim 18, wherein the at least one guest is a metal nanoparticle.

26. The method of claim 25, wherein the metal nanoparticle comprises at least one atom selected from the group consisting of Au, Ag, Cu, Pt, Pd, Ru, Fe, Cd, Zn, and Ni.

27. The method of claim 18, wherein the at least one guest molecule is a biomacromolecule.

28. The method of claim 27, wherein the biomacromolecule is selected from the group consisting of a DNA sequence, an RNA sequence, a protein, and an enzyme.

29. The method of claim 18, wherein the at least one guest molecule comprises a linker.

30. The method of claim 29, wherein the linker is a chemical entity that binds a metal ion.

31. A method for determining the molecular structure of at least one guest molecule conjugated to a porous protein crystal, the method comprising:
- (a) obtaining a porous protein crystal guest molecule conjugate, wherein the porous protein crystal guest molecule conjugate comprises a guest molecule, wherein the guest molecule comprises a metal nanoparticle, biomacromolecule, or a combination thereof, and a porous protein crystal, wherein the porous protein crystal comprises:
  - at least one pore having a diameter equal to or greater than 3 nm wherein the at least one pore's diameter is large enough to permit entry of the entirety of at least one guest molecule into the pore; and
  - at least one binding site for the at least one guest molecule within the interior of the at least one pore,
  wherein the porous protein crystal has been reacted with a crosslinking agent to produce a crosslinked porous protein crystal and the crosslinking agent crosslinks adjacent monomers of the porous protein crystal;
- (b) imaging the porous protein crystal guest molecule conjugate; and
- (c) determining the molecular structure of the at least one guest molecule.

32. The method of claim 31, wherein X-ray diffraction is used to image the porous protein crystal guest molecule conjugate.

33. A method for preparing a porous protein crystal guest molecule conjugate, the method comprising:
- obtaining a porous protein crystal, wherein the porous protein crystal comprises at least one pore and at least one binding site for the at least one guest molecule within the interior of the at least one pore, wherein the at least one pore's diameter is large enough to permit entry of the entirety of at least one guest molecule into the pore;
- reacting the porous protein crystal with a crosslinking agent to produce a crosslinked porous protein crystal, wherein the crosslinking agent bonds adjacent monomers of the porous protein crystal, and wherein the crosslinking agent comprises at least one functional group selected from N-hydroxysuccinimide (NHS ester), imidoester, maleimide, pyridyldithiol, carbodiimide, aldehyde, and combinations thereof, and;
- incubating the crosslinked porous protein crystal with at least one guest molecule to produce a porous protein crystal guest molecule conjugate, wherein the at least one guest molecule comprises a metal nanoparticle, a biomacromolecule, or a combination thereof.

34. The method of claim 33, wherein the crosslinking agent is selected from the group consisting of 1-Ethyl-3-[3-dimethylaminopropyl] carbodiimide hydrochloride (EDC); formaldehyde; formaldehyde, and urea; formaldehyde and guanidinium hydrochloride; glyoxal; glyoxal and p-dimethylaminobenzaldehyde (DMAB); glutaraldehyde and p-dimethylaminobenzaldehyde (DMAB); 1-Ethyl-3-[3-dimethylaminopropyl] carbodiimide hydrochloride (EDC); 1-Ethyl-3-[3-dimethylaminopropyl] carbodiimide hydrochloride (EDC) and imidazole; 1-Ethyl-3-[3-dimethylaminopropyl] carbodiimide hydrochloride (EDC) and N-hydroxysulfo succinimide (Sulfo-NHS); 1-Ethyl-3-[3-dimethylaminopropyl] carbodiimide hydrochloride (EDC) and malonic acid; or a crosslinking agent with two or more N-hydroxysuccinimide (NHS ester) functional groups.

35. The method of claim 33, wherein the porous protein crystal is reacted with a crosslinking agent from about 5 minutes to about 24 hours.

36. The method of claim 33, further comprising quenching the porous protein crystal during or after the crosslinking reaction by changing the solution surrounding the porous protein crystals such that the solution surrounding the porous protein includes new molecules that reduce or eliminate the tendency of reactive groups on the crystal to interact in undesirable ways with subsequently or concurrently introduced guest molecules.

37. The method of claim 36, further comprising quenching the porous protein crystal with a solution comprising at least one sacrificial molecule capable of consuming the reactive groups present in the crosslinked crystal.

38. The method of claim 36, further comprising quenching the porous protein crystal with a solution comprising at least one reducing agent.

39. The method of claim 38, wherein the reducing agent is selected from the group consisting of p-dimethylaminobenzaldehyde (DMAB), dithiothreitol (DTT), tris(2-carboxyethyl)phosphine (TCEP), beta-mercaptoethanol (BME), dithiobutylamine (DTBA), hydroxylamine, or combinations thereof.

40. The method of claim 38, wherein the reducing agent is selected from the class of chemical compounds that include borohydride, cyanoborohydride, or combinations thereof.

41. The method of claim 38, wherein the crosslinking agent includes at least one reactive aldehyde group and wherein the sacrificial reactive molecule contains at least one amine group.

42. The method of claim 41, wherein the crosslinking agent is selected from the group consisting of formaldehyde, glyoxal, or combinations thereof and the sacrificial reactive molecule is a small molecule (molecular weight of less than 1000 Daltons).

43. The method of claim 33, wherein the porous protein crystal comprises one or more protecting group(s) that are installed prior to the crosslinking step.

44. The method of claim 43, wherein the porous protein crystal comprises one or more protected cysteine amino acids.

45. The method of claim 44, wherein the protecting group is derived from a chemical entity that comprises at least one class of functional group selected from the group consisting of disulfide, dithiol, thiosulfonate, tetrathionate, maleimide, bimane.

46. The method of claim 45, wherein the protecting group is derived from a protecting agent selected from the group consisting of 5,5'-dithiobis-(2-nitrobenzoic acid)(Ellman reagent or DTNB), methyl methanethiosulfonate (MMTS), or tetrathionate.

* * * * *

SEQUENCE LISTING

```
<160> NUMBER OF SEQ ID NOS: 6

<210> SEQ ID NO 1
<211> LENGTH: 612
<212> TYPE: DNA
<213> ORGANISM: Artificial Sequence
```

<220> FEATURE:
<223> OTHER INFORMATION: SYNTHESIZED

<400> SEQUENCE: 1

```
atatgtccct taaaaaagtt ttattgagtt cattggttgc ggtgtctttg ttaagcacag      60
gtttgtttgc taaagaatat actttagata aagcacatac agatgtaggt tttaaaatca     120
aacatttaca aattagcaat gtaaaaggaa atttcaaaga ttattctgcg gtgattgatt     180
ttgatcctgc gagtgctgaa tttaaaaagc ttgatgtaac tataaaaatc gcatctgtaa     240
atacagaaaa tcaaacaaga gataatcact acaacaaga tgattttttc aaagcaaaaa      300
aatatcctga tatgactttt acaatgaaaa atatgaaaa aatcgataat gaaaaaggca      360
aaatgacagg aactttaact atagctggag tttctaaaga tatcgtttta gatgctgaaa     420
tcggcggtgt agctaaaggc aaagatgaaa agaaaaaat aggatttctt ttaaatggaa      480
aaatcaaacg ctctgatttt aaatttgcaa caagtacttc aactattact ttaagtgatg     540
atattaattt aaatatcgaa gttaaagcga acgaaaaaga agggggatcc caccaccacc     600
accaccactg ag                                                         612
```

<210> SEQ ID NO 2
<211> LENGTH: 178
<212> TYPE: PRT
<213> ORGANISM: Campylobacter jejuni

<400> SEQUENCE: 2

```
Met Lys Glu Tyr Thr Leu Asp Lys Ala His Thr Asp Val Gly Phe Lys
 1               5                  10                  15

Ile Lys His Leu Gln Ile Ser Asn Val Lys Gly Asn Phe Lys Asp Tyr
                20                  25                  30

Ser Ala Val Ile Asp Phe Asp Pro Ala Ser Ala Glu Phe Lys Lys Leu
            35                  40                  45

Asp Val Thr Ile Lys Ile Ala Ser Val Asn Thr Glu Asn Gln Thr Arg
        50                  55                  60

Asn His Leu Gln Gln Asp Asp Phe Phe Lys Ala Lys Lys Tyr Pro Asp
65                  70                  75                  80

Met Thr Phe Thr Met Lys Lys Tyr Glu Lys Ile Asp Asn Glu Lys Gly
                85                  90                  95

Lys Met Thr Gly Thr Leu Thr Ile Ala Gly Val Ser Lys Asp Ile Val
               100                 105                 110

Leu Asp Ala Glu Ile Gly Gly Val Ala Lys Gly Lys Asp Gly Lys Glu
           115                 120                 125

Ile Gly Phe Ser Leu Asn Gly Lys Ile Lys Arg Ser Asp Phe Lys Phe
       130                 135                 140

Ala Thr Ser Thr Ser Thr Ile Thr Leu Ser Asp Asp Ile Asn Leu Asn
145                 150                 155                 160

Ile Glu Val Lys Ala Asn Glu Lys Glu Gly Gly Ser His His His
               165                 170                 175

His His
```

<210> SEQ ID NO 3
<211> LENGTH: 662
<212> TYPE: DNA
<213> ORGANISM: Campylobacter jejuni

<400> SEQUENCE: 3

```
ttaagaagga gatatacata tgaaaaaagt tctgctgagc agcctggttg cagttagcct      60
```

-continued

```
gctgagtacc ggtctgtttg caaaagaata taccctggat aaagcccata ccgatgttgg    120
ctttaaaatc aaacatctgc agattagcaa tgtgaaaggc aactttaaag attatagcgc    180
agtgatcgat tttgatccgg caagtgcaga attcaaaaaa ctggatgtga ccattaaaat    240
cgccagcgtg aataccgaaa atcagacccg tgataatcat ctgcagcagg atgacttctt    300
caaagccaaa aaatacccgg atatgacctt taccatgaaa aaatacgaga aaatcgataa    360
cgaaaaaggc aaaatgaccg gcaccctgac cattgccggt gttagcaaag atattgttct    420
ggatgcagaa attggtggtg ttgccaaagg taaagatggc aaagaaaaaa ttggctttag    480
cctgaacggc aaaatcaaac gtagcgattt caaatttgca accagcacca gcaccattac    540
cctgagtgat gacattaatc tgaacattga agtgaaagcc aacgagaaag aaggtggtag    600
tcatcaccac caccatcact aataactcga gcaccaccac caccaccact gagatccggc    660
tg                                                                   662
```

```

<210> SEQ ID NO 4
<211> LENGTH: 180
<212> TYPE: PRT
<213> ORGANISM: Campylobacter jejuni

<400> SEQUENCE: 4

Met Lys Glu Tyr Thr Leu Asp Lys Ala His Thr Asp Val Cys Phe Lys
1               5                   10                  15

Ile Lys His Leu Gln Ile Ser Asn Val Lys Gly Asn Phe Lys Asp Tyr
            20                  25                  30

Ser Ala Val Ile Asp Phe Asp Pro Ala Ser Ala Glu Phe Lys Lys Leu
        35                  40                  45

Asp Val Thr Ile Lys Ile Ala Ser Val Asn Thr Glu Asn Gln Thr Arg
    50                  55                  60

Asp Asn His Leu Gln Gln Asp Asp Phe Phe Lys Ala Lys Lys Tyr Pro
65                  70                  75                  80

Asp Met Thr Phe Thr Met Lys Lys Tyr Glu Lys Ile Asp Asn Glu Lys
                85                  90                  95

Gly Lys Met Thr Gly Thr Leu Thr Ile Ala Gly Val Ser Lys Asp Ile
            100                 105                 110

Val Leu Asp Ala Glu Ile Gly Gly Val Ala Lys Gly Lys Asp Gly Lys
        115                 120                 125

Glu Lys Ile Gly Phe Ser Leu Asn Gly Lys Ile Lys Arg Ser Asp Phe
    130                 135                 140

Lys Phe Ala Thr Ser Thr Ser Thr Ile Thr Leu Ser Asp Asp Ile Asn
145                 150                 155                 160

Leu Asn Ile Glu Val Lys Ala Asn Glu Lys Glu Gly Gly Ser His His
                165                 170                 175

His His His His
            180

<210> SEQ ID NO 5
<211> LENGTH: 180
<212> TYPE: PRT
<213> ORGANISM: Campylobacter jejuni

<400> SEQUENCE: 5

Met Lys Glu Tyr Thr Leu Asp Lys Ala His Thr Asp Val Gly Phe Lys
1               5                   10                  15

Ile Lys His Leu Gln Ile Ser Asn Val Lys Gly Cys Phe Lys Asp Tyr
```

```
            20                  25                  30
Ser Ala Val Ile Asp Phe Asp Pro Ala Ser Ala Glu Phe Lys Lys Leu
            35                  40                  45

Asp Val Thr Ile Lys Ile Ala Ser Val Asn Thr Glu Asn Gln Thr Arg
        50                  55                  60

Asp Asn His Leu Gln Gln Asp Asp Phe Phe Lys Ala Lys Lys Tyr Pro
65                  70                  75                  80

Asp Met Thr Phe Thr Met Lys Lys Tyr Glu Lys Ile Asp Asn Glu Lys
                85                  90                  95

Gly Lys Met Thr Gly Thr Leu Thr Ile Ala Gly Val Ser Lys Asp Ile
                100                 105                 110

Val Leu Asp Ala Glu Ile Gly Gly Val Ala Lys Gly Lys Asp Gly Lys
            115                 120                 125

Glu Lys Ile Gly Phe Ser Leu Asn Gly Lys Ile Lys Arg Ser Asp Phe
            130                 135                 140

Lys Phe Ala Thr Ser Thr Ser Thr Ile Thr Leu Ser Asp Asp Ile Asn
145                 150                 155                 160

Leu Asn Ile Glu Val Lys Ala Asn Glu Lys Glu Gly Gly Ser His His
                165                 170                 175

His His His His
        180

<210> SEQ ID NO 6
<211> LENGTH: 180
<212> TYPE: PRT
<213> ORGANISM: Campylobacter jejuni

<400> SEQUENCE: 6

Met Lys Glu Tyr Thr Leu Asp Lys Ala His Thr Asp Val Gly Phe Lys
1               5                   10                  15

Ile Lys His Leu Gln Ile Ser Asn Val Lys Gly Asn Phe Lys Asp Tyr
            20                  25                  30

Ser Ala Val Ile Asp Phe Asp Pro Ala Ser Ala Glu Phe Lys Lys Leu
            35                  40                  45

Asp Val Thr Ile Lys Ile Ala Ser Val Asn Thr Glu Asn Gln Thr Arg
        50                  55                  60

Asp Asn His Leu Gln Gln Asp Asp Phe Phe Lys Ala Lys Lys Tyr Pro
65                  70                  75                  80

Asp Met Thr Phe Thr Met Lys Lys Tyr Glu Lys Ile Asp Asn Glu Lys
                85                  90                  95

Gly Lys Met Thr Gly Thr Leu Thr Ile Ala Gly Val Ser Lys Asp Ile
                100                 105                 110

Val Leu Asp Ala Glu Ile Gly Gly Val Ala Lys Gly Lys Asp Gly Lys
            115                 120                 125

Glu Lys Ile Gly Phe Ser Leu Asn Gly Lys Ile Lys Arg Ser Asp Phe
            130                 135                 140

Lys Phe Ala Thr Ser Thr Ser Thr Ile Thr Leu Ser Asp Asp Ile Asn
145                 150                 155                 160

Leu Cys Ile Glu Val Lys Ala Asn Glu Lys Glu Gly Gly Ser His His
                165                 170                 175

His His His His
        180
```